United States Patent
Moskowitz et al.

(10) Patent No.: US 11,701,388 B2
(45) Date of Patent: *Jul. 18, 2023

(54) THROMBOSOMES AS AN ANTIPLATELET AGENT REVERSAL AGENT

(71) Applicant: Cellphire, Inc., Rockville, MD (US)

(72) Inventors: Keith Andrew Moskowitz, Westfield, IN (US); Braden Carl Ishler, Montgomery Village, MD (US); William Matthew Dickerson, Washington, DC (US); Narendra Nath Tandon, Gaithersburg, MD (US); Amber Nicole Lee, Montgomery Village, MD (US); Glen Michael Fitzpatrick, North Potomac, MD (US)

(73) Assignee: Cellphire, Inc., Rockville, MD (US)

( * ) Notice: Subject to any disclaimer, the term of this patent is extended or adjusted under 35 U.S.C. 154(b) by 121 days.

This patent is subject to a terminal disclaimer.

(21) Appl. No.: 16/994,377

(22) Filed: Aug. 14, 2020

(65) Prior Publication Data

US 2021/0046121 A1 Feb. 18, 2021

Related U.S. Application Data

(60) Provisional application No. 63/065,337, filed on Aug. 13, 2020, provisional application No. 62/887,923, filed on Aug. 16, 2019.

(51) Int. Cl.
| | | |
|---|---|---|
| *A61K 35/19* | (2015.01) | |
| *A61P 7/04* | (2006.01) | |
| *A61K 45/06* | (2006.01) | |
| *A61K 47/26* | (2006.01) | |
| *A61K 47/42* | (2017.01) | |

(52) U.S. Cl.
CPC .............. *A61K 35/19* (2013.01); *A61K 45/06* (2013.01); *A61K 47/26* (2013.01); *A61K 47/42* (2013.01); *A61P 7/04* (2018.01)

(58) Field of Classification Search
CPC ........ A61K 35/19; A61K 45/06; A61K 47/26; A61K 47/42; A61K 31/192; A61K 31/4365; A61K 31/4465; A61K 31/519; A61K 31/616; A61K 31/7076; A61K 38/363; A61K 38/57; A61K 9/0019; A61K 47/02; A61K 2300/00; A61P 7/04; C12N 5/0644
See application file for complete search history.

(56) References Cited

U.S. PATENT DOCUMENTS

| | | |
|---|---|---|
| 3,932,943 A | 1/1976 | Briggs et al. |
| 4,157,383 A | 6/1979 | Sedlacek et al. |
| 4,455,299 A | 6/1984 | Grode |
| 4,865,871 A | 9/1989 | Livesey et al. |
| 4,994,367 A | 2/1991 | Bode |
| 5,059,518 A | 10/1991 | Kortright et al. |
| 5,213,814 A | 5/1993 | Goodrich |
| 5,332,578 A | 7/1994 | Chao |
| 5,364,756 A | 11/1994 | Livesey et al. |
| 5,423,738 A | 6/1995 | Robinson |
| 5,571,801 A | 11/1996 | Segall |
| 5,622,867 A | 4/1997 | Livesy |
| 5,656,498 A | 8/1997 | Iijima |
| 5,656,598 A | 8/1997 | Dunstan et al. |
| 5,723,281 A | 3/1998 | Segall et al. |
| 5,736,313 A | 4/1998 | Spargo |
| 5,759,542 A | 6/1998 | Gurewich |
| 5,800,978 A | 9/1998 | Goodrich |
| 5,817,381 A | 10/1998 | Chen |
| 5,827,741 A | 10/1998 | Beattie |
| 5,919,614 A | 7/1999 | Livesey |
| 5,958,670 A | 9/1999 | Goodrich |
| 5,993,804 A | 11/1999 | Read |
| 6,127,111 A | 10/2000 | Braun |
| 6,211,575 B1 | 4/2001 | Hansford |
| 6,221,575 B1 | 4/2001 | Roser |
| 6,372,423 B1 | 4/2002 | Braun |
| 6,596,296 B1 | 7/2003 | Nelson |
| 6,653,062 B1 | 11/2003 | DePablo |
| 6,723,497 B2 | 4/2004 | Wolkers |
| 6,770,478 B2 | 8/2004 | Crowe |
| 6,833,236 B1 | 12/2004 | Stienstra |
| 6,858,222 B2 | 2/2005 | Nelson |
| 7,033,603 B2 | 4/2006 | Nelson |

(Continued)

FOREIGN PATENT DOCUMENTS

| | | |
|---|---|---|
| CA | 1261259 A | 9/1989 |
| CA | 2097063 C | 6/1992 |

(Continued)

OTHER PUBLICATIONS

Etchill E. et al. Platelet Transfusion in Critical Care and Surgery. Shock 47(5)537-549, May 1, 2017. (Year: 2017).*

(Continued)

*Primary Examiner* — Aaron J Kosar

(74) *Attorney, Agent, or Firm* — Double Helix Law; Emanuel Vacchiano

(57) ABSTRACT

In some embodiments provided herein is a method of treating a coagulopathy in a subject, the method including administering to the subject in need thereof an effective amount of a composition including platelets or platelet derivatives and an incubating agent including one or more salts, a buffer, optionally a cryoprotectant, and optionally an organic solvent, wherein the subject has been treated or is being treated with an antiplatelet agent.

22 Claims, 32 Drawing Sheets

(56) References Cited

U.S. PATENT DOCUMENTS

| | | | |
|---|---|---|---|
| 7,169,606 B2 | 1/2007 | DePablo | |
| 7,514,095 B2 | 4/2009 | Nelson | |
| 7,811,558 B2 | 10/2010 | Ho | |
| 8,097,403 B2 | 1/2012 | Ho | |
| 8,486,617 B2 * | 7/2013 | Ho | A61P 13/12 435/2 |
| 8,486,619 B2 | 7/2013 | Miller | |
| 8,529,961 B2 | 9/2013 | Campbell | |
| 8,877,060 B2 | 11/2014 | Sehal | |
| 8,900,209 B2 | 12/2014 | Rosati | |
| 9,402,866 B2 | 8/2016 | Radwanski et al. | |
| 9,545,379 B2 | 1/2017 | Liu et al. | |
| 9,863,699 B2 | 1/2018 | Corbin et al. | |
| 9,878,011 B2 | 1/2018 | Landrigan et al. | |
| 9,950,035 B2 | 4/2018 | Binder et al. | |
| 10,400,017 B2 | 9/2019 | Higgins et al. | |
| 10,441,634 B2 | 10/2019 | Landrigan et al. | |
| 10,539,367 B2 | 1/2020 | Corbin et al. | |
| 10,793,327 B2 | 10/2020 | Weimer et al. | |
| 10,843,100 B2 | 11/2020 | Khan et al. | |
| 10,969,171 B2 | 4/2021 | Corbin et al. | |
| 10,976,105 B2 | 4/2021 | Corbin et al. | |
| 11,052,045 B2 | 7/2021 | Liu et al. | |
| 2001/0019819 A1 | 9/2001 | Wolkers et al. | |
| 2001/0028880 A1 | 10/2001 | Fisher | |
| 2001/0046487 A1 | 11/2001 | Roser et al. | |
| 2002/0009500 A1 | 1/2002 | Wolkers et al. | |
| 2002/0076445 A1 | 6/2002 | Crowe | |
| 2003/0022333 A1 | 1/2003 | Bronshtein | |
| 2003/0073238 A1 | 4/2003 | Dzekunov et al. | |
| 2003/0148449 A1 | 8/2003 | Kuliopulos et al. | |
| 2003/0157475 A1 | 8/2003 | Schenk | |
| 2004/0136974 A1 | 7/2004 | Crowe | |
| 2004/0147024 A1 | 7/2004 | Crowe | |
| 2004/0152964 A1 | 8/2004 | Crowe | |
| 2004/0185524 A1 | 9/2004 | Crowe | |
| 2004/0265293 A1 | 12/2004 | Crowe et al. | |
| 2005/0028559 A1 | 2/2005 | Hiromatsu | |
| 2005/0048460 A1 | 3/2005 | Crowe | |
| 2005/0074402 A1 | 4/2005 | Cagnolini | |
| 2005/0181978 A1 | 8/2005 | Rojkjaer et al. | |
| 2005/0191286 A1 | 9/2005 | Gandy | |
| 2006/0034809 A1 | 2/2006 | Ho et al. | |
| 2006/0035383 A1 | 2/2006 | Ho | |
| 2006/0051731 A1 | 3/2006 | Ho | |
| 2006/0223050 A1 | 10/2006 | Crowe et al. | |
| 2007/0087061 A1 | 4/2007 | Drake | |
| 2007/0166389 A1 | 7/2007 | Bakaltcheva | |
| 2007/0178104 A1 | 8/2007 | Awdalla | |
| 2007/0243178 A1 | 10/2007 | Ho et al. | |
| 2007/0248612 A1 | 10/2007 | Wilson | |
| 2007/0249047 A1 | 10/2007 | McKenna, Jr. | |
| 2008/0064628 A1 | 3/2008 | Goodall et al. | |
| 2008/0145834 A1 | 6/2008 | Ho et al. | |
| 2008/0286366 A1 | 11/2008 | Fischer et al. | |
| 2008/0299212 A1 | 12/2008 | Kim | |
| 2009/0035289 A1 | 2/2009 | Wagner et al. | |
| 2009/0111118 A1 | 4/2009 | Mylvaganam et al. | |
| 2009/0175905 A1 | 7/2009 | Tseng et al. | |
| 2009/0299212 A1 | 12/2009 | Principe et al. | |
| 2010/0055067 A1 | 3/2010 | Park | |
| 2010/0135969 A1 | 6/2010 | Mishra | |
| 2010/0190717 A1 | 7/2010 | Bevec | |
| 2010/0196461 A1 | 8/2010 | Simpkins | |
| 2010/0267928 A1 | 10/2010 | Heckl | |
| 2011/0008804 A1 | 1/2011 | Kain et al. | |
| 2011/0020107 A1 | 1/2011 | Presz, Jr. et al. | |
| 2011/0027257 A1 | 2/2011 | Burnouf | |
| 2011/0183311 A1 | 7/2011 | Ho | |
| 2011/0189151 A1 | 8/2011 | Stossel et al. | |
| 2012/0009221 A1 | 1/2012 | Hoerr et al. | |
| 2012/0028236 A1 | 2/2012 | Sehgal | |
| 2012/0095085 A1 | 4/2012 | Layzer et al. | |
| 2012/0141434 A1 | 6/2012 | Peled et al. | |
| 2012/0264815 A1 | 10/2012 | Sullenger et al. | |
| 2012/0276581 A1 | 11/2012 | Arav et al. | |
| 2012/0321722 A1 | 12/2012 | Liu | |
| 2013/0059380 A1 | 3/2013 | Ho et al. | |
| 2013/0061849 A1 | 3/2013 | Lemper | |
| 2013/0122107 A1 | 5/2013 | Bakaltcheva | |
| 2013/0195959 A1 | 8/2013 | Patel | |
| 2013/0210903 A1 | 8/2013 | Sullenger et al. | |
| 2014/0065120 A1 | 3/2014 | Nichols | |
| 2014/0329323 A1 | 11/2014 | Nygaard et al. | |
| 2014/0330226 A1 | 11/2014 | Coffey | |
| 2014/0356948 A1 | 12/2014 | Jeon et al. | |
| 2015/0064259 A1 | 3/2015 | Simpkins et al. | |
| 2015/0306212 A1 | 10/2015 | Kahvejian et al. | |
| 2015/0313943 A1 | 11/2015 | Kishikawa et al. | |
| 2015/0361453 A1 | 12/2015 | Gresele et al. | |
| 2016/0082044 A1 | 3/2016 | Liu et al. | |
| 2016/0206783 A1 | 7/2016 | Dietz | |
| 2016/0219870 A1 | 8/2016 | Wang et al. | |
| 2016/0231338 A1 | 8/2016 | Aster et al. | |
| 2016/0235781 A1 | 8/2016 | Emanuele | |
| 2016/0324897 A1 | 11/2016 | Ingber et al. | |
| 2017/0198335 A1 | 7/2017 | Muller | |
| 2017/0333593 A1 | 11/2017 | Willard | |
| 2018/0009874 A1 | 1/2018 | Wilcox et al. | |
| 2018/0070581 A1 | 3/2018 | Tarrand et al. | |
| 2018/0092348 A1 | 4/2018 | She et al. | |
| 2018/0169027 A1 | 6/2018 | Zhang et al. | |
| 2018/0169139 A1 | 6/2018 | Feuerstein | |
| 2018/0235894 A1 | 8/2018 | Gu et al. | |
| 2018/0311176 A1 | 11/2018 | Ozsolak | |
| 2018/0312903 A1 | 11/2018 | Grölz | |
| 2019/0008143 A1 | 1/2019 | Dee | |
| 2019/0076478 A1 | 3/2019 | Hale et al. | |
| 2020/0046771 A1 | 2/2020 | Kuhn et al. | |
| 2020/0060262 A1 | 2/2020 | Stolla | |
| 2020/0076455 A1 | 3/2020 | Sharf | |
| 2020/0078407 A1 | 3/2020 | Bhattacharya et al. | |
| 2020/0093853 A1 | 3/2020 | Feuerstein | |
| 2020/0206143 A1 | 7/2020 | Moskowitz et al. | |
| 2020/0208109 A1 * | 7/2020 | Moskowitz | C12N 15/113 |
| 2020/0208110 A1 | 7/2020 | Lee et al. | |
| 2020/0224164 A1 | 7/2020 | Moskowitz et al. | |
| 2020/0281980 A1 | 9/2020 | Willard et al. | |
| 2020/0291356 A1 | 9/2020 | Jorda et al. | |
| 2020/0346167 A1 | 11/2020 | Montgomery et al. | |
| 2021/0046120 A1 | 2/2021 | Moskowitz et al. | |
| 2021/0069240 A1 | 3/2021 | Jorda et al. | |
| 2021/0100846 A1 | 4/2021 | Lee et al. | |
| 2021/0180016 A1 | 6/2021 | Moskowitz et al. | |
| 2021/0189341 A1 | 6/2021 | Sheik et al. | |
| 2021/0299179 A1 | 9/2021 | Moskowitz et al. | |
| 2021/0308066 A1 | 10/2021 | Moskowitz et al. | |
| 2021/0308185 A1 | 10/2021 | Moskowitz et al. | |
| 2021/0315935 A1 | 10/2021 | Moskowitz et al. | |
| 2021/0353680 A1 | 11/2021 | Bhattacharya et al. | |
| 2021/0368782 A1 | 12/2021 | Dee et al. | |
| 2022/0168353 A1 * | 6/2022 | Moskowitz | A01N 1/0221 |
| 2022/0211029 A1 | 7/2022 | Moskowitz et al. | |
| 2022/0273724 A1 * | 9/2022 | Moskowitz | A61K 9/19 |
| 2022/0279777 A1 | 9/2022 | Moskowitz et al. | |

FOREIGN PATENT DOCUMENTS

| | | |
|---|---|---|
| CA | 2136848 A1 | 12/1993 |
| CA | 2393315 A1 | 6/2001 |
| CA | 2840568 A1 | 1/2013 |
| CA | 3053041 A1 | 2/2020 |
| CN | 103524613 | 1/2014 |
| CN | 103907595 | 7/2014 |
| CN | 108715834 A | 10/2018 |
| EP | 0967862 | 1/2003 |
| EP | 1374890 A2 | 1/2004 |
| EP | 1652538 | 5/2006 |
| EP | 1784639 A2 | 5/2007 |
| EP | 3681518 A1 | 7/2020 |
| EP | 3307283 B1 | 9/2020 |
| EP | 3551198 B1 | 2/2022 |
| JP | H08109136 | 4/1996 |
| JP | 2005053841 | 3/2005 |

(56) References Cited

FOREIGN PATENT DOCUMENTS

| | | | |
|---|---|---|---|
| JP | 2012143554 A | | 8/2012 |
| WO | WO 1990/005461 | | 5/1990 |
| WO | 9012581 | A1 | 11/1990 |
| WO | 1991017655 | A1 | 11/1991 |
| WO | WO 1992008349 | | 5/1992 |
| WO | WO 1993000806 | | 1/1993 |
| WO | 1993023997 | A1 | 12/1993 |
| WO | 9428950 | A1 | 12/1994 |
| WO | 1998034478 | A1 | 8/1998 |
| WO | 1999055346 | A1 | 11/1999 |
| WO | 2001058266 | A1 | 8/2001 |
| WO | 2003014305 | A2 | 2/2003 |
| WO | 2003090839 | A1 | 11/2003 |
| WO | WO 2004050896 | | 6/2004 |
| WO | 2005002499 | A2 | 1/2005 |
| WO | 2005020893 | A2 | 3/2005 |
| WO | 2005021706 | A2 | 3/2005 |
| WO | WO 2005/077299 | | 8/2005 |
| WO | 2005002499 | A3 | 11/2005 |
| WO | WO 2006020773 | | 2/2006 |
| WO | 2006059329 | A1 | 6/2006 |
| WO | 2004050896 | A3 | 12/2006 |
| WO | 2006020773 | A3 | 7/2007 |
| WO | 2010046949 | A1 | 4/2010 |
| WO | WO 2011/020107 | | 2/2011 |
| WO | 2011020107 | A3 | 10/2011 |
| WO | 2012018484 | A2 | 4/2012 |
| WO | 2012074637 | A2 | 6/2012 |
| WO | 2014051537 | A1 | 4/2014 |
| WO | WO 2014055949 | | 4/2014 |
| WO | 2014066142 | A1 | 5/2014 |
| WO | WO 2014118817 | | 8/2014 |
| WO | 2014118817 | A3 | 10/2014 |
| WO | 2015073587 | A2 | 5/2015 |
| WO | 2015191632 | A1 | 12/2015 |
| WO | WO 2016014854 | | 1/2016 |
| WO | WO 2016057041 | | 4/2016 |
| WO | 2016077682 | A1 | 5/2016 |
| WO | 2016141325 | A1 | 9/2016 |
| WO | WO 2016201081 | | 12/2016 |
| WO | WO 2017040238 | | 3/2017 |
| WO | 2017123539 | A1 | 7/2017 |
| WO | WO 2018106250 | | 6/2018 |
| WO | 2019055683 | A1 | 3/2019 |
| WO | WO 2020/023905 | | 1/2020 |
| WO | 2020056009 | A1 | 3/2020 |
| WO | WO 2020112963 | | 6/2020 |
| WO | WO 2020113035 | | 6/2020 |
| WO | WO 2020113090 | | 6/2020 |
| WO | WO 2020113101 | | 6/2020 |
| WO | 2020165152 | A1 | 8/2020 |
| WO | 2020186193 | A1 | 9/2020 |
| WO | 2020227149 | A1 | 11/2020 |
| WO | 2021011857 | A1 | 1/2021 |
| WO | 2021034716 | A1 | 2/2021 |
| WO | 2021034719 | A1 | 2/2021 |
| WO | 2021046409 | A1 | 3/2021 |
| WO | 2021108538 | A1 | 6/2021 |
| WO | 2021108539 | A1 | 6/2021 |
| WO | 2021158622 | A1 | 8/2021 |
| WO | 2021158625 | A1 | 8/2021 |
| WO | 2021158641 | A1 | 8/2021 |
| WO | 2021158645 | A1 | 8/2021 |
| WO | 2021158646 | A1 | 8/2021 |
| WO | 2021232015 | A1 | 11/2021 |
| WO | 2022103861 | A1 | 5/2022 |
| WO | 2022178177 | A1 | 8/2022 |
| WO | 2022178191 | A1 | 8/2022 |
| WO | 2022178177 | A4 | 10/2022 |

OTHER PUBLICATIONS

Marder V. Bleeding Complications of Thrombolytic Treatment. American J of Hospital Pharmacy 47(Suppl 2)S15-19, Sep. 1990. (Year: 1990).*
Sane, D. et al. Bleeding During Thrombolytic Therapy for Acute Myocardial Infarction. Annals Internal Medicine 111(12)1010-22, 1989. (Year: 1989).*
Cap, A. et al. Trauma Induced Coagulopathy, Chapter 22: Platelet Transfusion, pp. 347-376, 2016. (Year: 2016).*
Chen et al., "Modifying murine von Willebrand factor A1 domain for in vivo assessment of human platelet therapies," Nature biotechnology, Jan. 2008, 26(1):114-119.
diapharma.com [online], "DiaPharmaProductList," retrieved on Feb. 18, 2021, retrieved from URL<http://diapharma.com/wp-content/uploads/2016/03/DiaPharmaProductList_ML-00-00002REV7.pdf>, 4 pages.
helena.com [online], "Ristocetin Cofactor Assay," retrieved on Feb. 18, 2021, retrieved from URL <https://www.helena.com/Procedures/Pro064Rev5.pdf>, 2 pages.
Homepage.haemonetics.com [online], "TEG® 5000 Thrombelastograph® Hemostasis Analyzer System," retrieved Feb. 18, 2021, retrieved from URL<http://homepage.haemonetics.com/en/products/devices/surgical-and-diagnostic-devices/teg-5000>, 3 pages.
Luo et al., "Construction and in vitro studies of magnetic-apoferritin nanocages conjugated with KGDS peptide targeted at activated platelets for the MRI diagnosis of thrombus," Journal of Nanoparticle Research, Aug. 2019, 21(8):1-12.
PCT International Preliminary Report on Patentability in International Appln. No. PCT/US2019/043723, dated Feb. 11, 2021, 14 pages.
PCT International Search Report and Written Opinion for International Appln. No. PCT/US2020/62214, dated Mar. 17, 2021, 9 pages.
PCT International Search Report and Written Opinion in International Appln. No. PCT/US2020/049489, dated Feb. 16, 2021, 8 Pages.
PCT International Search Report and Written Opinion in International Appln. No. PCT/US2020/062216, dated Feb. 9, 2021, 9 pages.
thrombinoscope.com [online], "Thrombin Calibrator," retrieved on Feb. 18, 2021, retrieved from URL <https://www.thrombinoscope.com/method-products/products/>, 2 pages.
Whitney et al. "Ratiometric Activatable Cell-Penetrating Peptides Provide Rapid In Vivo Readout of Thrombin Activation," Angewandte Chemie International Edition, 2013, 52:325-330.
2.palomar.edu [online], "The Five Kingdoms Of Life," Feb. 1998, retrieved on May 17, 2021, retrieved from URL <https://www2.palomar.edu/users/warmstrong/trfeb98.htm>; 18 pages.
Appleman et al., "Cryopreservation of canine platelets," Journal of veterinary internal medicine, Jan. 2009, 23(1):138-145.
Clemmons et al., "Acquisition and aggregation of canine blood platelets: basic mechanisms of function and differences because of breed origin," American journal of veterinary research, Jan. 1, 1984, 45(1):137-144.
Extended European Search report in EP Appln. No. 18856149.2, dated May 26, 2021, 9 pages.
Healthline.com [online], "How Many Cells Are in the Human Body? Fast Facts," Jul. 18, 2018, retrieved on May 17, 2021, retrieved from URL<https://www.https://www.healthline.com/health/number-of-cells-in-body>, 11 pages.
Lee et al., "Novel treatment modalities: New platelet preparations and subsititutes," British journal of haematology, Sep. 2001, 114(3):496-505.
microbenotes.com [online], "Types of Plant Cell—Definition, Structure, Functions, Diagrams," Feb. 25, 2020, retrieved May 17, 2021, retrieved from URL<microbenotes.com/types-of-plant-cell/>, 31 pages.
PCT International Preliminary Report on Patentability in PCT Appln. No. PCT/US2019/063549, dated Jun. 10, 2021, 9 pages.
PCT International Preliminary Report on Patentability in PCT Appln. No. PCT/US2019/063650, dated Jun. 10, 2021, 9 pages.
PCT International Preliminary Report on Patentability in PCT Appln. No. PCT/US2019/063750, dated Jun. 10, 2021, 8 pages.
PCT International Preliminary Report on Patentability in PCT Appln. No. PCT/US2019/063736, dated Jun. 10, 2021, 8 pages.

(56) References Cited

OTHER PUBLICATIONS

PCT International Search Report and Written Opinion in PCT Appln. No. PCT/US2021/016390, dated May 18, 2021, 13 pages.
PCT International Search Report and Written Opinion in PCT Appln. No. PCT/US2021/016360, dated May 21, 2021, 13 pages.
PCT International Search Report and Written Opinion in PCT Appln. No. PCT/US2021/016363, dated May 18, 2021, 15 pages.
PCT International Search Report and Written Opinion in PCT Appln. No. PCT/US2021/016389, dated May 18, 2021, 15 pages.
Scheinkönig et al., "Adoption of long-term cultures to evaluate the cryoprotective potential of trehalose for freezing hematopoietic stem cells," Bone marrow transplantation, Sep. 2004, 34(6):531-536.
Abdelgawwad, et al., "Transfusion of plateletes loaded with recombinant ADAMTS13 is efficacious for inhibiting arterial thrombosis in mice and in human," Arterioscler. Thromb. Vas. Biol., 2018, 38(11):2731-2743.
Adams, ed., Ducry, et al., "The principles of freeze-drying," DNA Repair Protocols, Methods in Molecular Biology, Humana Press, US, 2007, Chapter 2, 368:15-38.
Agam et al. "Passive Participation of Fixed Platelets in Aggregation Facilitated by Covalently Bound Fibrinogen" Blood 61:1, pp. 186-191, 1983.
Ahmadzada, et al., "Fundamentals of siRNA and miRNA therapeutics and a review of targeted nanoparticle delivery systems in breast cancer," Biophysical Reviews, 2018, 10:69-86.
Al Ghaithi, "Evaluation of the total Thrombus-Formation System (T-TAS)," Platelets, 2018, 1-8.
Arav, et al., "Freeze drying (lyophilization) of red blood cells," Journal of Trauma, 2011, 70:S61-S64.
Arnold P., et al., "The preparation and clinical administration of lyophilized platelet material to children with acute leukemia and aplastic anemia," The Journal of Pediatrics, 1956, 49(5):517-522.
Bynum, et al., "Evaluation of a lyophilized platelet-derived hemostatic product," Transfusion, 2019, 49:1490-1498.
Cellphire, "Loading Platelets with Biological Agents for Enhanced Local Delivery," 2006, 14 pages.
Chen, et al., "Advance of molecular imaging technology and targeted imaging agent in imaging and therapy," Biomed. Res. Int., 2014, 819324, 12 pages.
Chen, et al., "Stabilizaton of peptides against proteolysis through disulfide-bridged conjugation with synthetic aromatics," Org. Biomol. Chem., 2017, 15(8):1921-1929.
Christenson et al., "Autologous fibrin glue reinforced by platelets in surgery of ascending aorta", Thorac. Cardiovasc. Surg., vol. 52, p. 225-229, 2004.
Christopher, et al., "MicroRNA therapeutics: discovering novel targets and developing specific therapy," Perspect. Clin. Res., 2016, 7(2):68-74.
Cox, et al., "Platelets and the innate immune system: mechanisms of bacterial-induced platelet activation," Journal of Thrombosis and Haemostasis, 2011, 9:1097-1107.
Cryoprotein.The American Heritage® Stedman's Medical Dictionary. Houghton Mifflin Company. Mar. 24, 2010, <Dictionary.com http://dictionary.reference.com/browse/cryoprotein>.
Daidone, "Usefulness of the Total Thrombus-formation Analysis System (T-TAS) in the diagnosis and characterization of von Willebrand disease," Haemophillia, 2016, 22:949-956.
Daly, et al., "Hemostatic regulators of tumor angiogenesis: a source of antiangiogenic agents for cancer treatment?" Journal of the National Cancer Institute, 2003, 95(22):1660-1673.
Dennison, "A simple and universal method for making up buffer solutions," Biochem. Edu., 1988, 16(4):210-211.
Dielis, et al., "Coagulation factors and the protein C system as determinants of thrombin generation in a normal population," J. Thromb. Haemost., 2008, 6:125-131.
Diener, "Antiplatelet agents and randomized trials," Review in Neurological Diseases, 2007, 4(4):177-183.

Dong, et al., "Ristocetin-dependent, but not botrocetin-dependent, binding of von Willebrand factor to the platelet glycoprotein Ib-IX-V complex correlates with shear-dependent interactions," Blood, 2001, 97:162-+168.
European Search Report in EP Appln. No. 05784165.2, dated Mar. 26, 2008.
European Search Report in EP Appln. No. 16808270.9, dated Nov. 22, 2018.
European Search Report in EP Appln. No. 16842662.5, dated Jul. 26, 2019.
Expose, http://dictionary.reference.com/browse/expose, accessed Jul. 18, 2009.
Extended European Search report in EP Appln. No. 16923314.5, dated Jun. 18, 2020, 7 pages.
Extended European Search Report in EP Appln. No. 17738796.6, dated Jul. 23, 2019.
Fijnheer et al., "Platelet activation during preparation of platelet concentrates: a comparison of the platelet-rich plasma and the buffy coat methods," Transfusion, 1990, 30(7):634-638.
Fischer et al., "Primary and secondary hemostatic functionalities of rehydrated, lyophilized platelets," 2006, Transfusion, 46:1943-1950.
Fitzpatrick, et al., "Thrombosomes: a platelet-derived hemostatic agent for control of noncompressible hemorrhage," Transfusion, 2013, 53:100S-106S.
Gaertner et al., "Migrating platelets are mechano-scavengers that collect and bundle bacteria," Cell, Nov. 30, 2017, 171(6):1368-1382.
Gilbert et al., "Platelet-derived microparticles express high affinity receptors for factor VIII.", J.Biol.Chem., 1991, 266:17261-17268.
Giles et al., "A combination of factor Xa and phosphatidylcholine-phosphatidylserine vesicles bypasses factor VIII in vivo", Br. J., Haematol., 1988, 69(4):491-497.
Greene, et al., "Chapter 9: Component Preparation and Manufacturing," Transfusion Medicine and Hemostasis, Elsevier Science, 2009, pp. 45-50.
Heitz, et al., "Twenty years of cell-penetrating peptides: from molecular mechanisms to therapeutics," British Journal of Pharmacology, 2009, 157:195-206.
Hemker, et al., "Calibrated automated thrombin generation measurement in clotting plasma," Pathophysiol. Haemost. Thromb., 2003, 33:4-15.
Hoffman et al., "Coagulation Factor IXa Binding to Activated Platelets and Platelet-Derived Microparticles: A Flow Cytometric Study," Thromb. Haemost., 1992, 68:74-78.
Holcomb, et al., "Optimal fluid therapy for traumatic hemorrhagic shock," Crit. Care Clin., 2017, 33(1):15-36.
Holme et al., "Platelet-derived microvesicles and activated platelets express factor Xa activity," Blood Coagul. Fibrinolysis, 1995, 6:302-310.
Hong, et al., "Transfection of human platelets with short interfering RNA," Clin. Transl. Sci., 2011, 4(3):180-182.
Hrachovinova et al., "Interaction of P-selectin and PSGL-1 generates microparticles that correct hemostasis in a mouse model of hemophilia A," Nat Med., 2003, 9(8): 1020-1025.
Invitation to Pay Additional Fees in PCT Appln. No. PCT/US2020/022705, dated May 18, 2020, 2 pages.
Ishler, "StablePlate RX Canine Promotes in vitro Thromblin Generation and Thrombus Formation Under High Shear," Journal of Veterinary Internal Medicine, 2019 ACVIM Forum Research Abstract Program, p. 2483, Abstract Only.
Ito, et al., "Total Thrombus-formation Analysis System (T-TAS) can predict periprocedural bleeding events in patients undergoing catheter ablation for atrial fibrillation," Journal of American Heart Association, 2015, 5(1):e002744, 12 pages.
Kariko, et al., "Phosphate-enhanced transfection of cationic lipid-complexed mRNA and plasmid DNA," Biochim. Biophys. Acta, 1998, 1369(2):320-334.
Kerrigan, "Platelet interactions with bacteria," The non-thrombotic role of platelets in health and disease; Chapter 4, 2015, 65-84.

(56) References Cited

OTHER PUBLICATIONS

Kerrigan, et al., "Molecular basis for *Staphylococcus aureus* mediated platelet aggregate formation under arterial shear in vitro," Arteriosclerosis Thrombosis and Vascular Biology, 2008, 28(2):334-340.
Kirby et al., "Preparation of liposomes containing Factor VIII for oral treatment of haemophilia," 1984, J. Microencapsul. 1(1): 33-45.
Kishbaugh et al., "Intervening with Platelet Therapies," NEHL at the National Zoo, 2017, vol. 4 #2, 4 Pages.
Lam, et al., "siRNA versus miRNA as therapeutics for gene silencing," Molecular Therapy—Nucleic Acids, 2015, 4:e252.
Lannan, et. al., "Breaking the Mold: Transcription Factors in the Anuceleate Platelet and Platelet-Derived Microparticles," Front Imunnol., 2015, 6:48, 17 pages.
Makielski, et al., "Development and implementation of a novel immune thrombocytopenia bleeding score for dogs," J. Vet. Intern. Med., 2018, 32(3):1-10.
Mazzucco et al., "The use of autologous platelet gel to treat difficult-to-heal wounds: a pilot study," Transfusion, 2004, 44:1013-1018.
MedWow, "Manufacturer Specifications—CS-2000 Plus, Baxter," Apr. 19, 2011, retrieved on Sep. 26, 2019 from http://www.medwow.com/med/apheresis-machine/baxter/cs-3000-plus/5782.model-spec, 2 pages.
Merten et al., "Platelet Microparticles Promote Platelet Interaction with Subendothelial Matrix in a Glycoprotein lib/IIIa Dependent Mechanism", Circulation, 1999, 99:2577-2582.
Miajlovic, et al., "Both complement- and fibrinogen-dependent mechanisms contribute to platelet aggregation mediated by *Staphylococcus aureus* clumping factor B," Infection and Immunity, 2007, 75(7):3335-3343.
Mishra, et al., "Cell-penetrating peptides and peptide nucleic acid-coupled MRI contrast agents: evaluation of cellular delivery and target binding," Bioconjugate Chem., 2009, 20:1860-1868.
Montecinos, et al., "Selective targeting of bioengineered platelets to prostate cancer vasculature: new paradigm for the therapeutic modalities," 2015, 19(7):1530-1537.
Morris, et al., "A peptide carrier for the delivery of biologically active proteins into mammalian cells," Nature Biotechnology, 2001, 19:1173-1176.
Morrison et al. "Storage of apheresis platelet concentrates after manual replacement of >95% of plasma with PAS 5," Vox Sangunis, May 2014, 107(3):247-253.
Natan, et al., "Freeze-drying of mononuclear cells derived from umbilical cord blood followed by colony formation," PLoS One, 2009, 4(4):e5240.
Nieuwland et al., "Cell-derived microparticles generated in patients during cardiopulmonary bypass are highly procoagulant", Circulation, 1997, 96:3534-3541.
Novakowski, et. al., "Delivery of mRNA to platelets using lipid nanoparticles," Scientific Reports, 2019, 9:552, 11 pages.
O'Brien, et al., "Multiple mechanisms for the activation of human platelet aggregation by *Staphylococcus aureus*: roles for the clumping factors ClfA and ClfB, the serine-aspartate repeat protein SdrE and protein A," Molecular Microbiology, 2002, 44(4):1033-1044.
Oikarinen et al., "Augmentation of the narrow traumatized anterior alveolar ridge to facilitate dental implant placement," Dent. Traumatol., 2003, 19:19-29.
Oliver, "Dry state preservation of nucleated cells: progress and challenge," Cryobiology, 2011, 63(3):307, abstract.
PCT International Preliminary Report on Patentability in International Appln. No. PCT/US2017/012836, dated Jul. 17, 2018.
PCT International Preliminary Report on Patentability in International Appln. No. PCT/US2005/28559, dated May 8, 2007.
PCT International Preliminary Report on Patentability in International Appln. No. PCT/US2015/060533, dated May 16, 2017.
PCT International Preliminary Report on Patentability in International Appln. No. PCT/US2016/036657, dated Dec. 12, 2017.
PCT International Preliminary Report on Patentability in International Appln. No. PCT/US2016/048846, dated Mar. 6, 2018.
PCT International Preliminary Report on Patentability in International Appln. No. PCT/US2016/065681, dated Jun. 11, 2019.
PCT International Preliminary Report on Patentability in PCT Appln. No. PCT/US2018/050924, dated Mar. 17, 2020, 17 pages.
PCT International Search Report and Written Opinion in International Appln. No. PCT/US2005/28559, dated Mar. 23, 2007.
PCT International Search Report and Written Opinion in International Appln. No. PCT/US2015/060533, dated Jan. 28, 2016.
PCT International Search Report and Written opinion in International Appln. No. PCT/US2016/036657, dated Aug. 29, 2016.
PCT International Search Report and Written Opinion in International Appln. No. PCT/US2016/048846, dated Nov. 16, 2016.
PCT International Search Report and Written Opinion in International Appln. No. PCT/US2016/065681, dated Feb. 17, 2017.
PCT International Search Report and Written Opinion in International Appln. No. PCT/US2017/012836, dated Apr. 7, 2017.
PCT International Search Report and Written Opinion in International Appln. No. PCT/US2018/050924, dated Nov. 20, 2018.
PCT International Search Report and Written Opinion in International Appln. No. PCT/US2020/046522, dated Nov. 10, 2020, 10 Pages.
PCT International Search Report and Written Opinion in International Appln. No. PCT/US2020/046525, dated Nov. 10, 2020, 11 Pages.
PCT International Search Report and Written Opinion in PCT Appln. No. PCT/US2019/043723, dated Oct. 9, 2019, 16 pages.
PCT International Search Report and Written Opinion in PCT Appln. No. PCT/US2019/050624, dated Nov. 20, 2019, 23 pages.
PCT International Search Report and Written Opinion in PCT Appln. No. PCT/US2019/063549, dated Feb. 4, 2020, 10 pages.
PCT International Search Report and Written Opinion in PCT Appln. No. PCT/US2019/063650, dated Feb. 27, 2020, 11 pages.
PCT International Search Report and Written Opinion in PCT Appln. No. PCT/US2019/063736, dated Feb. 20, 2020, 10 pages.
PCT International Search Report and Written Opinion in PCT Appln. No. PCT/US2019/063750, dated Feb. 19, 2020, 10 pages.
PCT International Search Report and Written Opinion in PCT Appln. No. PCT/US2020/022705, dated Jul. 29, 2020, 12 pages.
PCT International Search Report and Written Opinion in PCT Appln. No. PCT/US2020/031172, dated Aug. 12, 2020, 9 pages.
PCT International Search Report and Written Opinion in PCT Appln. No. PCT/US2020/042492, dated Nov. 24, 2020, 9 pages.
Pierce et al., "Platelet-derived growth factor and transforming growth factor-beta enhance tissue repair activities by unique mechanisms", J. Cell Biol., 1989, 109:429-440.
Platelet. The American Heritage® Dictionary of the English Language, Fourth Edition. Houghton Mifflin Company, 2004. Mar. 23, 2010. <Dictionary.com http://dictionary.reference.com/browse/platelet>.
Prior et al., "A Sprayable Hemostat Containing Fibrillar Collagen, Bovine Thrombin, and Autologous Plasma", An.Thorac.Surg., 1999, 68:479-485.
Robson et al., "Coronavirus RNA proofreading: molecular basis and therapeutic targeting," Molecular Cell, Aug. 4, 2020, 18 Pages.
Rosing et al., "Impaired factor X and prothrombin activation associated with decreased phospholipid exposure in platelets from a patient with a bleeding disorder", Blood, 1985, 65:1557-1561.
Rounding. Dictionary.com. Dictionary.com Unabridged (v 1.1 ). Random House, Inc. http://dictionary.reference.com/browse/rounding (accessed: Oct. 27, 2008).
Rowley, et. al., "Platelet mRNA: the meaning behind the message," Curr. Opin. Hematol., 2012, 19(5):385-391.
scbcinfo.org [online], Strong, ed., "Indications for platelet transfusion therapy," available on or before Dec. 25, 2005, via Internet Archive: Wayback Machine URL <https://web.archive.org/web/20051225110714/http://www.scbcinfo.org/publications/bulletin_v2_n2.htm>, 7 pages.
Serebruany, et al., "Crossreactivity of Human versus Swine Platelet Surface Antigens Is Similar for Glycoproteins Ib and IIIa, but Not for the Glycoprotein IIb/IIIa Complex," J.Thromb. and Thromb., 1998, 5:37-41.

(56) References Cited

OTHER PUBLICATIONS

Sims et al., "Complement Proteins C5b-9 Cause Release of Membrane Vesicles from the Platelet Surface That Are Enriched in the Membrane Receptor for Coagulation Factor Va and Express Prothrombinase Activiy", J. Biol Chem., 1988, 263:18205-18212.
Sims et al., "Regulatory control of complement on blood platelets. Modulation of platelet procoagulant responses by a membrane inhibitor of the C5b-9 complex", J Biol. Chem., 1989, 264:19228-19235.
Steed, "The role of growth factors in wound healing," Surg. Clin. North Am., 1997, 77:575-586.
Strober, "Trypan blue exclusion test of cell viability," Current Protocols in Immunology, 1997, A.3B.1-A.3B.2.
Szekely and Lex, "Antifibrinolytics," Heart, Lung and Vessels, 2014, 6(1):5-7.
Tacar, et al., "Doxorubicin: an update on anticancer molecular action, toxicity and novel drug delivery systems," The Journal of Pharmacy and Pharmacology, 2013, 65(2):157-170.
Tans et al., "Comparison of anticoagulant and procoagulant activities of stimulated platelets and platelet-derived microparticles", Blood, 1991, 77:2641-2648.
Taune, et al., "Whole blood coagulation assays ROTEM and T-TAS to monitor dabigatran t dabigatran treatment," Thrombosis Research, 2017, 153(30):76-82.
Tsegaye et al., "Platelet activation suppresses HIV-1 infection of T cells," Retrovirology, 2013, 10:48.
T-TAS.info [online], Publications, 2019, retrieved on Aug. 28, 2019, retrieved from URL<https://www.t-tas.info/pub/>, 8 pages.
Ullah et al., "A Review on Malarial Parasite," World Journal of Zoology, 2015, 10(4):285-290.
Valentini, et al., "Use of CD9 and CD61 for the characterization of AML-M7 by flow cytometry in a dog," Vet. Comp. Oncol., 2011, 10:312-318.
Valeri, et al., "Survival of baboon biotin-X-N-hydroxysuccinimide and 111In-oxine-labelled autologous fresh and lyophilized reconstituted platelets," Vox Sanguinis, 2005, 88:122-129.
Vlieghe, et al., "Synthetic therapeutic peptides: science and market," Drug Discovery Today, 2010, 15:40-56.
Volz, et al., "Inhibition of platelet GPVI induces intratumor hemorrhage and increases efficacy of chemotherapy in mice," Blood, 2019, 133(25):2696-2706.
Wajon et al., "Intraoperative Plateletpheresis and Autologous Platelet Gel Do Not Reduce Chest Tube Drainage or Allogeneic Blood Transfusion After Reoperative Coronary Artery Bypass Graft", Anesth. Analg., 2001, 93:536-542.
Wang, et al., "Commonly used dietary supplements on coagulation function during surgery," Medicines, 2015, 2:157-185.
Wilkerson, M.J., et al., "Platelet size, platelet surface-associated IgG, and reticulated platelets in dogs with immune-mediated thrombocytopenia," Veterinary Clinical Pathology, 2001, 30(3):141-149.
Wilson, et al., "A simple rapid method for layering blood on Ficoll-Isopaque gradients," Journal of Immunological Methods, 1975, 9(1): 67-68.
Wolkers et al., "Human Platelets Loaded with Trehalose Survive Freeze-Drying", Cryobiology 42:79-87, 2001.
WPI Database No. AN 2014-E98028 / CN103524613, Jan. 22, 2014: 2 pages.
Xu, et al., "Doxorubicin-loaded platelets as a smart drug delivery system: an improved therapy for lymphoma," Scientific Reports, 2017, 7:42632.
Yarovoi et al., "Factor VIII ectopically expressed in platelets: efficacy in hemophilia A treatment", Blood 102(12): 4006-4013, 2003.
Zhou, et. al., "Loading Trehalose into Red Blood Cells by Improved Hypotonic Method," Cell Preservation Technology, 2008, 6(2):119-122.
PCT International Preliminary Report on Patentability in International Appln. No. PCT/US2019/050624, dated Mar. 25, 2021, 10 pages.
International Preliminary Report on Patentability in International Appln. No. PCT/US2019/063750, dated Jun. 10, 2021, 8 pages.
International Search Report and Written Opinion in International Appln. No. PCT/US2021/032783, dated Aug. 24, 2021, 13 pages.
International Search Report and Written Opinion in International Appln. No. PCT/US2021/058814, dated Mar. 17, 2020, 14 pages.
International Search Report and Written Opinion in International Appln. No. PCT/US2022/016866, dated Jul. 4, 2022, 18 pages.
International Search Report and Written Opinion in International Appln. No. PCT/US2022/016883, dated May 11, 2022.
Ishler et al., "Lyophilized Human Platelets Interact with Fresh Platelets to Promote Hemostasis Under Shear In Vitro", Cellphire, Inc., 2021, 2 page, Abstract.
Ishler et al., "Lyophilized Human Platelets Interact with Fresh Platelets to Promote Hemostasis Under Shear In Vitro", Cellphire, Inc., Jul. 2021, 1 page, Poster.
Ishler et al., "Lyophilized Platelets Show Hemostatic Function Independent of von Willebrand Factor", Cellphire, Inc., Department of Discovery and Research, ISth 2020 Virtual Congress, Jul. 2020, 1 page, Poster.
Ishler et al., "StablePlate RX®Canine Promotes In Vitro Thrombin Generation and Thrombus Formation Under High Shear", Cellphire, Inc., 2019, 1 page, Poster1.
Ishler et al., "StablePlate RX®Canine Promotes In Vitro Thrombin Generation and Thrombus Formation Under High Shear", Cellphire, Inc., 2019, 1 page, Poster2.
Jennings et al., "Antiplatelet and anticoagulant agents: Key differences in mechanisms of action, clinical application, and therapeutic benefit in patients with non-ST-segment-elevation acute coronary syndromes", Current Opinion in Cardiology vol. 23, No. 4, Jul. 2008, pp. 302-308, DOI: 10.1097/HCO.0b013e3283021ad9.
Jennings et al., "The pharmacodynamics of parenteral glycoprotein IIb/IIIa inhibitors", Journal of Interventional Cardiology, vol. 15, No. 1, Feb. 2002, pp. 45-60, DOI: 10.1111/j.1540-8183.2002.tb01034.x.
Joshi et al., "Lyophilised Reconstituted Human Platelets Increase Thrombus Formation In A Clinical Ex Vivo Model Of Deep Arterial Injury", Thrombosis and Haemostasis, vol. 108, No. 1, 2012, pp. 176-182, DOI: 10.1160/TH12-02-0059.
Joshi et al., "Thrombosomes Show Dose-Dependent Increase in Thrombus Formation in a Model of Deep Arterial Injury", Blood, vol. 118, Issue 21, Nov. 18, 2011, Abstract 2319, 8 pages, doi.org/10.1182/blood.V118.21.2319.2319.
Kuhn et al., "Assessing Circulation Persistence of Human Platelet Products in a NOD-SCID Mouse Model", Cellphire, Inc. Jul. 2022, 1 page, Poster.
Lassila et. al., "Dynamic Monitoring of Platelet Deposition on Severely Damaged Vessel Wall in Flowing Blood. Effects of Different Stenoses on Thrombus Growth", Arteriosclerosis, vol. 10, No. 2, Mar.-Apr. 1990, pp. 306-315, doi: 10.1161/01.atv.10.2.306.
Lee et al., "High Efficiency Transfection and Preservation of Platelets with Tumor Suppressing Short RNA", Cellphire, Inc. Jul. 2020, 1 page, Poster.
Lee et al., "Lyophilized Human Platelets Exhibit Adhesive Interactions with *Staphylococcus aureus*", Cellphire, Inc. Jul. 2020, 1 page, Poster.
Li etal., "Extended antiplatelet therapy with clopidogrel alone versus clopidogrel plus aspirin after completion of 9- to 12-month dual antiplatelet therapy for acute coronary syndrome patients with both high bleeding and ischemic risk. Rationale and design of the OPT-BIRISK double-blinded, placebo-controlled randomized trial", American Hear Journal, vol. 228, Oct. 2020, pp. 1-7, https://doi.org/10.1016/j.ahj.2020.07.005.
Lo et al., "Development of a multi-compartment microfiltration device for particle fractionation" 16th International Conference on Miniaturized Systems for Chemistry and Life Sciences, MicroTAS 2012—Okinawa, Japan, Oct. 28, 2012-Nov. 1, 2012, 3 pages.
Lucking et. al., "Characterisation and reproducibility of a human ex vivo model of thrombosis", Thrombosis Research, vol. 126, No. 5, Nov. 2010, pp. 431-435, doi: 10.1016/j.thromres.2010.06.030.

(56) References Cited

OTHER PUBLICATIONS

Machine Language Translation of Chinese Patent No. CN108715834 A Titled [EN], "A Kind of Platelet Lysates Liquid and Preparation Method There of Rich in CD41+, CD81+ Micro-Capsule", Oct. 30, 2018, 10 pages.

Machine Language Translation of Japanese Patent JP2012143554 A2 Titled "[EN] Polysulfone-Based Hollow Fiber Membrane, Hollow Fiber Membrane Module for Cleaning Platelet Suspension, and Cleaning Method of Platelet Suspension.", Aug. 2, 2012, 33 pages.

Mailer et al., "Commentary on "Pharmacological profile of asundexian, a novel, orally bioavailable inhibitor of factor XIa": Small molecule factor XIa inhibitor asundexian allows for safer anticoagulation", Journal of Thrombosis and Haemostasis, vol. 20, Issue 6, Jun. 2022, pp. 1309-1311, https://doi.org/10.1111/jth.15722.

Marris, "The war against wounds", Nature, Mar. 21, 2007, Issue 446, pp. 369-371.

Mathews et al., "Development of Lyophilized Platelet-Derived Extracellular Vesicles for Multiple Indications", Cellphire, Inc., Oct. 2020, 1 page, Poster.

Mathews et al., "Development of Lyophilized Platelet-Derived Extracellular Vesicles for Multiple Indications", Chellphire, Inc., 2020, 1 page, Abstract.

McCarrel, et. al., "Temporal Growth Factor Release from Platelet-Rich Plasma, Trehalose Lyophilized Platelets, and Bone Marrow Aspirate and Their Effect on Tendon and Ligament Gene Expression" Journal of Orthopaedic Research : Official Publication of the Orthopaedic Research Society, vol. 27(8), Aug. 1, 2009, pp. 1033-1042, DOI: 10.1002/jor.20853.

Mehendale, et. al., "Platelet Enrichment From Whole Blood In A Clog-Free Microfluidic Radial Pillar Device (RAPID)", Biomedical Microdevices, bioRxiv, Oct. 4, 2017, DOI: https://doi.org/10.1101/197749.

Mehendale, et. al., "Platelet Enrichment In A Continuous And Clog-Free Microfluidic Filter With Sunflower Head Geometry", 20th International Conference on Miniaturized Systems for Chemistry and Life Sciences, Dublin, Ireland, Oct. 9-13, 2016, pp. 272-273.

Meisel et. al., "A Simplified Direct Lipid Mixing Lipoplex Preparation: Comparison of Liposomal-, Dimethylsulfoxide-, and Ethanol-Based Methods", Scientific Reports, vol. 6, Article 27662, Jun. 21, 2016, 12 pages, doi: 10.1038/srep27662.

Midget et al., "Combination of freeze-dry microscopy, differential scanning calorimetry, and electron microscopy analysis as a guide for lyophilization cycle optimization to enhance Thrombosomes function", Cryobiology, vol. 63, Issue 3, 2011, p. 320, Abstract, doi:10.1016/j.cryobiol.2011.09.054.

Mihatov, et. al., "Individualizing Dual Antiplatelet Therapy (DAPT) Duration Based on Bleeding Risk, Ischemic Risk, or Both: An Analysis From the DAPT Study", Cardiovascular Revascularization Medicine, vol. 41, Aug. 2022, pp. 105-112, https://doi.org/10.1016/j.carrev.2022.01.006.

Montague, "Strategies To Improve Haemostasis In Trauma: Evaluation Of Thrombosomes In The Presence Of Native Platelet Dysfunction", vol. 100, Issue Suppl 3, 2014, pp. A91-92, DOI:10.1136/heartjnl-2014-306118.158.

Moskowitz et al., "Hemostatic Properties of Infusible Trehalose-Stabilized Lyophilized Platelet Derivatives", Blood, vol. 104, Issue 11, Nov. 16, 2004, p. 834, Abstract, doi.org/10.1182/blood.V104.11.834.834.

Moskowitz, "Thrombosomes for the Treatment of Bleeding Associated with Aggressive Anticoagulation", Cellphire, Inc., Dec. 2021, 40 pages, Posters.

Müller et. al., "Factor XI and XII as antithrombotic targets", Current Opinion In Hematology, vol. 15, No. 5, Sep. 2011, pp. 349-355, doi: 10.1097/MOH.0b013e3283497e61.

Mullin, et.al., "Doxorubicin chemotherapy for presumptive cardiac hemangiosarcoma in dogs", Veterinary and Comparative Oncology, vol. 14, Issue 4, Dec. 18, 2014, 13 pages, doi:10.1111/vco.12131.

NasrEldin, "Effect of cold storage on platelets quality stored in a small containers: Implications for pediatric transfusion", Pediatric Hematology Oncology Journal, vol. 2, Issue 2, Aug. 2017, pp. 29-34, doi.org/10.1016/j.phoj.2017.07.001.

Ohanian, et. al., "Freeze-Dried Platelets Are A Promising Alternative In Bleeding Thrombocytopenic Patients with Hematological Malignancies", American Journal of Hematology, vol. 97, Issue 3, Mar. 1, 2022, pp. 256-266, doi: 10.1002/ajh.26403.

Pietramaggiori, et. al., "Trehalose Lyophilized Platelets For Wound Healing", Wound Repair And Regeneration Official Publication Of The Wound Healing Society [and] the European Tissue Repair Society, vol. 15 (2), Mar. 9, 2007, pp. 213-220. doi:10.1111/j.1524-475X.2007.00207.x.

Powner, et. al., "Counteracting The Effects Of Anticoagulants And Antiplatelet Agents During Neurosurgical Emergencies", Neurosurgery, vol. 57, No. 5, Nov. 2005 pp. 823-831.

Read, et. al., "Preservation of hemostatic and structural properties of rehydrated lyophilized platelets: potential for long-term storage of dried platelets for transfusion", Proceedings of the National Academy of Sciences of the USA, vol. 92, Jan. 1995, pp. 397-401, DOI: 10.1073/pnas.92.2.397.

Reddoch et al., "Extended Storage of Refrigerated Platelets in Isoplate and Intersol PAS: An Evaluation of Two FDA-Approved Methods of Collection", Blood, vol. 128, Issue 22, Dec. 2, 2016, 3 pages, doi.org/10.1182/blood.V128.22.2631.2631.

Samanbar et al., "Evaluation Of The Hemostatic Ability of The New Device 'Total Thrombus Formation Analysis System' (T-TAS) for Thrombocytopenic Patients. Invitro effect of lyophilized human platelets", Cellphire, Inc. Jul. 2022, 1 page, Poster.

Schoug, et.al., "Differential effects of polymers PVP90 and Ficoll400 on storage stability and viability of Lactobacillus coryniformis Si3 freeze-dried in sucrose", Journal of Applied Microbiology, vol. 108, No. 3, pp. 1032-1040, Feb. 8, 2010.

Sheik et al., "Stably Loading Human Platelets with Gadolinium Conjugates to Enhance Magnetic Resonance Imaging", Cellphire, Inc., 2020,1 page.

Sibbing, et. al., "Antiplatelet effects of clopidogrel and bleeding in patients undergoing coronary stent placement", Journal of Thrombosis and Haemostasis, vol. 8, Issue 2, pp. 250-256, DOI: 10.1111/j.1538-7836.2009.03709.x.

Srivastava, et. al., "The rebirth of the contact pathway: a new therapeutic target", Current Opinion in Hematology, vol. 27, No. 5, Sep. 2020, pp. 311-319, doi: 10.1097/MOH.0000000000000603.

Sum et al., "Wound-healing properties of trehalose-stabilized freeze-dried outdated platelets", Transfusion, vol. 47, Issue 4, Apr. 2007, pp. 672-679, doi: 10.1111/j.1537-2995.2007.01170.x.

Alquwaizani, et.al., "Anticoagulants: A Review of the Pharmacology, Dosing, and Complications", Current Emergency and Hospital Medicine Reports, vol. 1, No. 2, Apr. 21, 2013, pp. 83-97, DOI: 10.1007/s40138-013-0014-6.

Bannai et al., "The effects of pH and agitation on platelet preservation", The Journal Of AABB Transfusion, vol. 25, Jan.-Feb. 1985, pp. 57-59, https://doi.org/10.1046/j.1537-2995.1985.25185116505.x.

Barroso, et. al., "Safety Evaluation Of A Lyophilized Platelet Derived Hemostatic Product", Transfusion, vol. 58 (12), Dec. 2018, pp. 2969-2977, DOI: 10.1111/trf.14972.

Böck et al., "Cryopreservation of human platelets with dimethyl sulfoxide: changes in biochemistry and cell function", Transfusion, vol. 35, No. 11, Nov.-Dec. 1995, pp. 921-924, doi: 10.1046/j.1537-2995.1995.351196110896.x.

Bohoněk, Miloš. "Cryopreservation of Platelets: Advances and Current Practice." Cryopreservation Biotechnology in Biomedical and Biological Sciences, Chapter 4. IntechOpen, Dec. 7, 2018, pp. 47-70.

Booth et al., "Lyophilized human platelets are superior to apheresis or fresh-drawn platelets in their ability to accelerate thrombin production", Cellphire, Inc. Jul. 2022, 1 page, Poster.

Charkhkar et al., "Amyloid beta modulation of neuronal network activity in vitro", Brain Research, vol. 1629, Dec. 2015, pp. 1-9, doi: 10.1016/j.brainres.2015.09.036.

Chelliah et. al., "P-selectin antagonism reduces thrombus formation in humans", Journal of Thrombosis and Haemostasis, vol. 7, No. 11, Nov. 2009, pp. 1915-1919. doi: 10.1111/j.1538-7836.2009.03587.x.

(56) References Cited

OTHER PUBLICATIONS

Colman, "Are hemostasis and thrombosis two sides of the same coin?", Journal of Experimental Medicine, Mar. 20, 2006, vol. 203, No. 3, pp. 493-495, doi: 10.1084/jem.20060217.
Cowles, "Anticoagulant effect of aspirin goes beyond platelet aggregation", Hematology/Oncology, May 1, 2007, 3 pages.
Crowe et. al., "Freeze-dried platelets: Moving towards clinical use", Cryobiology, vol. 66, Issue 3, Jun. 2013, p. 348, Abstract, doi.org/10.1016/j.cryobiol.2013.02.028.
Crowe et. al., "Stabilization of Dry Mammalian Cells: Lessons from Nature", Integrative and Comparative Biology, vol. 45, Issue 5, Nov. 2005, pp. 810-820, https://doi.org/10.1093/icb/45.5.810.
Crowe, et. al., "Stabilization of membranes in human platelets freeze-dried with trehalose", Chemistry and Physics of Lipids, vol. 122, Issues 1-2, Jan. 2003, pp. 41-52, https://doi.org/10.1016/S0009-3084(02)00177-9.
Dee et al., Trehalose Stabilized Freeze Dried Human Platelets, Thrombosomes, Express Surface Markers, Thromboelastogram (TEG) Values And Size Distribution Similar To Two To Three Day Old Stored Platelets, Cllphire, Inc., P-0453, 2019, 1 page, Poster.
Dickerson et al., "Lyophilized Human Platelets Restore Hemostasis in the Presence of the P2Y12 Inhibitors Cangrelor, Ticagrelor and Clopidogrel", Cellphire, Inc., 2020, 6 pages, Poster.
Dickerson et al., "Lyophilized Human Platelets Restore Hemostasis in the Presence of the P2Y12 Inhibitors Cangrelor, Ticagrelor and Clopidogrel", Cellphire Therapeutics Inc., Rockville, MD, 7 pages, Poster.
Dickerson et al., "Lyophilized Human Platelets Restore Hemostasis in the Presence of the P2Y12 Inhibitors Cangrelor, Ticagrelor and Clopidogre", American Society of Hematology, Blood,3.22 Disorders Of Coagulation Or Fibrinolysis, Nov. 5, 2020, 6 pages.
Dickerson et al., "Lyophilized human platelets support thrombosis unlike normal platelets in the presence of GPIIb/IIIa antagonists", Cellphire Therapeutics, ISth Virtual Congress, Jul. 2021, 1 page, Poster.
Dickerson et al., "Lyophilized human platelets support thrombosis unlike normal platelets in the presence of GPIIb/IIIa antagonists", Cellphire, Inc, AS-ISTH-2021-01436, 2021. 1 page, Abstract.
Dickerson et al., "Thrombosomes As a Treatment Option for Low-Dose Heparin Reversal", Cellphire, Inc, Oct. 2020. 1 page, Poster.
Dickson et al., "A scalable, micropore, platelet rich plasma separation device." Biomedical Microdevices, vol. 14 (6), Jul. 2012, pp. 1095-1102. DOI:10.1007/s10544-012-9675-2.
Dumont, et. al., "A randomized controlled trial evaluating recovery and survival of 6% dimethyl sulfoxide-frozen autologous platelets in healthy volunteers", Transfusion vol. 53(1), Jan. 2013, pp. 128-137.
Eikelboom, et. al., "Combined antiplatelet and anticoagulant therapy clinical benefits and risks", Journal of Thrombosis and Haemostasis, vol. 5, Suppl 1, Jul. 2007, pp. 255-263, DOI: 10.1111/j.1538-7836.2007.02499.x.
Extended European Search Report in EP Appln. No. 19840600.1 dated Mar. 25, 2022.
Extended European Search Report in EP Appln. No. 19888909.9 dated Sep. 28, 2022.
Extended European Search Report in EP Appln. No. 19888994.1 dated Nov. 7, 2022.
Extended European Search Report in EP Appln. No. 19891082.0 dated Sep. 30, 2022.
Fischer et al., "The interaction of factor VIIa with rehydrated, lyophilized platelets", Platelets, vol. 19 (3), May 2008, pp. 182-191, DOI:10.1080/09537100701493794.
Fischer, et. al., "Thrombus Formation with Rehydrated, Lyophilized Platelets", Hematology (Amsterdam, Netherlands), vol. 7 (6), Dec. 2002, pp. 359-369, DOI: 10.1080/1024533021000047954.
Fitzpatrick et al., "A Novel Lyophilized Platelet Derivative Produces Effective Hemostasis in Uncontrolled Bleeding/Shock Model without Systemic Thrombosis", Blood, vol. 118, Issue 21, Nov. 18, 2011, pp. 719-722, doi.org/10.1182/blood.V118.21.719.719.

Fitzpatrick et al., "Freeze-dried platelets: Advancing towards clinical use", Cryobiology, vol. 67, Issue 3, Dec. 2013, p. 420, Abstract, doi.org/10.1016/j.cryobiol.2013.09.086.
Fitzpatrick et al., "Stabilization and preservation of a platelet derived hemostatic agent, Thrombosomes", Cryobiology, vol. 63, Issue 3, Dec. 2011, p. 306, Abstract, doi:10.1016/j.cryobiol.2011.09.005.
Fitzpatrick et al., "Trehalose Stabilized Freeze Dried Human Platelets, Thrombosomes, Reduce Blood Loss In Thrombocytopenic Rabbit Ear Bleed Model By As Much As 89.5%", International Society of Blood Transfusion Vox Sanguinis, vol. 99, Suppl. 1, P-0452, 2010, p. 261, Abstract.
Fitzpatrick et al., "Trehalose Stabilized Freeze Dried Human Platelets, Thrombosomes, Express Surface Markers, Thromboelastogram (TEG) Values And Size Distribution Similar To Two To Three Day Old Stored Platelets", International Society of Blood Transfusion Vox Sanguinis, vol. 99, Suppl. 1, P-0453, 2010, p. 262, Abstract.
Fitzpatrick, "Novel platelet products under development for the treatment of thrombocytopenia or acute hemorrhage", Transfusion and Apheresis Science, vol. 58, Issue 1, Feb. 2019, pp. 7-11, doi: 10.1016/j.transci.2018.12.010.
Gao et al., "Development of Optimal Techniques for Cryopreservation of Human Platelets: I. Platelet activation during cold storage (at 22 and 8° C.) and cryopreservation", Cryobiology vol. 38(3), May 1999, pp. 225-235, DOI: 10.1006/cryo.1999.2162.
Godier et al., "Management of antiplatelet therapy for non elective invasive procedures of bleeding complications: proposals from the French working group on perioperative haemostasis (GIHP), in collaboration with the French Society of Anaesthesia and Intensive Care Medicine (SFAR)" Anaesthesia, Critical Care and Pain Medicine, vol. 38, Issue 3, Jun. 2019, pp. 289-302, doi: 10.1016/j.accpm.2018.10.004.
Goggs, et. al., "Lyophilized Platelets Versus Cryopreserved Platelets For Management Of Bleeding In Thrombocytopenic Dogs: A Multicenter Randomized Clinical Trial", Journal Of Veterinary Internal Medicine, Nov. 2020, vol. 34, Issue 6, pp. 2384-2397, doi: 10.1111/jvim.15922.
Grosset et al., "Rapid presymptomatic detection of PrPSc via conformationally responsive palindromic PrP peptides", Peptides, vol. 26, Issue 11, Nov. 2005, pp. 2193-2200, doi: 10.1016/j.peptides.2005.03.006.
Hagedorn, et. al., "Factor XIIa Inhibitor Recombinant Human Albumin Infesting Abolishes Occlusive Arterial Thrombus Formation Without Affecting Bleeding", Circulation, vol. 121, Issue 13, Apr. 6, 2010, pp. 1510-1517, DOI: 10.1161/CIRCULATIONAHA.109.924761.
Hale et al., "A Novel Use Of the NOD SCID Mouse Model for Hemostatic Efficacy", Cellphire, Inc., 2019, 1 page.
Heitmeier et al., "Pharmacological profile of asundexian, a novel, orally bioavailable inhibitor of factor XIa", Journal of Thrombosis and Haemostasis, vol. 20, No. 6, Jun. 2022, pp. 1400-1411, https://doi.org/10.1111/jth.15700.
Holmes, et. al., "Combining Antiplatelet and Anticoagulant Therapies", Journal of The American College of Cardiology, vol. 54, No. 2, Jul. 7, 2009, pp. 95-109.
Huebner et al., "Freeze-dried plasma enhances clot formation and inhibits fibrinolysis in the presence of tissue plasminogen activator similar to pooled liquid plasma", Transfusion, vol. 57, Issue 8, Aug. 2017, pp. 2007-2015, DOI:10.1111/trf.14149.
Human Translation of Chinese patent No. CN103907595 Published Jul. 9, 2014, Trehalose-containing platelet low temperature preservation solution and application thereof, First Inventor Zhao Shuming.
Inaba et al., "Dried platelets in a swine model of liver injury", Shock, vol. 41, Issue 5, May 2014, pp. 429-434, doi: 10.1097/SHK.0000000000000141.
International Partial Search Report in International Appln No. PCT/US2022/016866, dated May 11, 2022, 13 pages.
International Preliminary Report on Patentability in International Appln. No. PCT/US2019/063549, dated Jun. 10, 2021, 9 pages.
International Preliminary Report on Patentability in International Appln. No. PCT/US2019/063650, dated Jun. 10, 2021, 9 pages.

(56) References Cited

OTHER PUBLICATIONS

International Preliminary Report on Patentability in International Appln. No. PCT/US2019/063736, dated Jun. 10, 2021, 8 pages.
Swami, et.al., "von Willebrand Disease: A Concise Review and Update for the Practicing Physician", Clinical and Applied Thrombosis/Hemostasis, vol. 23 (8), Nov. 2017, pp. 900-910, DOI: 10.1177/1076029616675969.
Tang, et. al., "Targeted repair of heart injury by stem cells fused with platelet nano vesicles", Nature Biomedical Engineering, vol. 2, No. 1, May 30, 2018, pp. 17-26, DOI:10.1038/s41551-017-0182-x.
Trivedi, et. al., "Freeze-Dried Platelets Promote Clot Formation, Attenuate Endothelial Cell Permeability, And Decrease Pulmonary Vascular Leak In A Murine Model Of Hemorrhagic Shock", The Journal of Trauma and Acute Care Surgery, vol. 90, Issue 2, Feb. 1, 2021, pp. 203-214, doi: 10.1097/TA.0000000000002984.
Tsai, et.al, "Increased risk of bleeding in patients on clopidogrel therapy after drug-eluting stents implantation: insights from the HMO Research Network-Stent Registry (HMORN-stent)", Circulation Cardiovascular Interventions, vol. 3, Issue 3, Jun. 1, 2010, pp. 230-235, DOI: 10.1161/CIRCINTERVENTIONS.109.919001.
Undas, et. al., "Antithrombotic properties of aspirin and resistance to aspirin: beyond strictly antiplatelet actions", Blood, vol. 109, No. 6, Mar. 15, 2007, pp. 2285-2292, DOI: 10.1182/blood-2006-01-010645.
U.S. Appl. No. 15/776,255 Advisory Action dated Aug. 22, 2022.
U.S. Appl. No. 15/776,255 Advisory Action dated Aug. 8, 2022.
U.S. Appl. No. 15/776,255 Final Office Action dated May 23, 2022.
U.S. Appl. No. 15/776,255 Non-Final Office Action dated Nov. 16, 2022.
U.S. Appl. No. 15/776,255 Non-Final Office Action dated Nov. 19, 2021.
U.S. Appl. No. 15/776,255 Response To Final Office Action Filed Oct. 24, 2022, includes a Declaration Under 37 CFR 1.132.
U.S. Appl. No. 15/776,255 Response To Final Office Action Filed Jul. 25, 2022, includes a Declaration Under 37 CFR 1.132.
U.S. Appl. No. 15/776,255 Response To Non-Final Office Action Filed Mar. 23, 2022.
U.S. Appl. No. 15/776,255 Response To Restriction Requirement Filed Jan. 20, 2021.
U.S. Appl. No. 15/776,255 Response To Restriction Requirement Filed May 21, 2021.
U.S. Appl. No. 15/776,255 Response To Restriction Requirement Filed Sep. 27, 2021.
U.S. Appl. No. 15/776,255 Restriction Requirement dated Mar. 18, 2021.
U.S. Appl. No. 15/776,255 Restriction Requirement dated Jul. 20, 2020.
U.S. Appl. No. 15/776,255 Restriction Requirement dated Jun. 25, 2021.
Valeri et al., "Freezing human platelets with 6 percent dimethyl sulfoxide with removal of the supernatant solution before freezing and storage at−80° C. without post thaw processing" Transfusion, vol. 45 (12), Dec. 2005, pp. 1890-1898, DOI: 10.1111/j.1537-2995.2005.00647.x.
Van Der Meer et al, Platelet preservation: Agitation and containers, Transfusion and Apheresis Science, vol. 44, Issue 3, Jun. 2011, pp. 297-304, //doi.org/10.1016/j.transci.2011.03.005.
Van Der Meijden et al., "Platelet- and erythrocyte-derived microparticles trigger thrombin generation via factor XIIa", Journal of Thrombosis and Haemostasis, vol. 10, Issue 7, Apr. 26, 2012, pp. 1355-1362, doi.org/10.1111/j.1538-7836.2012.04758.x.
Vibhudutta et al., "Trehalose Stabilized Freeze Dried Human Platelets, Thrombosomes, Reduce Blood Loss In Thrombocytopenic Rabbit Ear Bleed Model By As Much As 89.5%", Cellphire, Inc. P-0454, www.bodevet.com, Mar. 2017, 1 page, Poster.
Vibhudutta et al., "Trehalose Stabilized Freeze Dried Human Platelets, Thrombosomes, Persist In Circulation 24 Hours After Infusion and Are Non-Immunogenic In New Zealand White Rabbits", International Society of Blood Transfusion Vox Sanguinis, vol. 99, Suppl. 1, P-0454, 2010, p. 262, Abstract.
Vibhudutta, et al., "Trehalose Stabilized Freeze Dried Human Platelets, Thrombosomes, Persist In Circulation 24 Hours After Infusion and Are Non-Immunogenic In New Zealand White Rabbits", Cellphire, Inc. P-0454, 1 page, Poster.
Viswanathan et al., "Clopidogrel Alters Thrombus Quantity and Quality in Patients With Type II Diabetes Mellitus and Stable Coronary Artery Disease", Journal of the American College of Cardiology, vol. 61, No. 10, Mar. 2013, E1154, 1 page.
Wei et al., "ICAM-5/Telencephalin Is a Functional Entry Receptor for Enterovirus D68", Cell Host Microbe, vol. 20, Issue 5, Nov. 9, 2016, pp. 631-641, doi: 10.1016/j.chom.2016.09.013.
Whitman et al., "Design of the CRYPTICS Trail: A Randomized Controlled Trial Comparing Cryopreserved to Liquid Stored Platelets in Patients Undergoing Cardiac Surgery", Journal of Thoracic and Cardiovascular Surgery, 2022, doi.org/10.1016/j.xjon.2022.11.003.
Wickramasinghe, "Washing Cryopreserved Blood Products Using Hollow Fibres", Food and Bioproducts Processing, vol. 77, Issue 4, Dec. 1999, pp. 287-292, DOI:org/10.1205/096030899532574.
Wright et al., "Doxorubicin delivery via novel lyophilized/reconstituted platelet-product has anti-cancer activity", Hematology & Transfusion International Journal, vol. 9, Issue 3, 2021, pp. 41-51.
Xu et al., "EACA Loaded Platelets Sustain Clots More Efficiently Than Free EACA", Cellphire, Inc., Jul. 2021, 1 page, Poster.
Xu et al., "EACA Loaded Platelets Sustain Clots More Efficiently Then Free EACA", Cellphire, Inc. 2021. 1 page.
Xu et al., "Human Platelet Derived Lyophilized Hemostatic Retains Hemostatic Properties Heparin Complexation with Protamine", Cellphire, Inc. Jul. 2022, 1 page, Poster.
Xu et al., "Thrombosomes As a Treatment Option for Low-Dose Heparin Reversal", Cellphire Therapeutics, Inc., Rockville, MD, 2020 Annual Meeting, 3 pages.
Zafar et. al., "Badimon Perfusion Chamber: An Ex Vivo Model of Thrombosis", Methods Molecular Biology, vol. 1816, 2018, pp. 161-171, doi: 10.1007/978-1-4939-8597-5_12.
Zhou et al., "Hemostatic and Thrombogenic Properties of Lyophilized Human Platelets", CellPhire, Inc. Jul. 2021, 1 page, Poster.
Zhou et al., "Lyophilized Human Platelets Promote Coagulation in Humanized Mouse VWF Transgenic Models of Hemostasis and Thrombosis", Cellphire, Inc., 2021, 1 page.

* cited by examiner

THROMBOSOMES AS AN ANTIPLATELET AGENT REVERSAL AGENT

CROSS-REFERENCE TO RELATED APPLICATIONS

This application claims priority to U.S. Provisional Application Ser. No. 62/887,923, filed on Aug. 16, 2019 and U.S. Provisional Application Ser. No. 63/065,337, filed on Aug. 13, 2020, each of which is incorporated herein by reference in its entirety.

FIELD OF THE INVENTION

This disclosure serves to describe the use of thrombosomes as a treatment for drug-induced coagulopathy. The use of antiplatelet drugs such as aspirin or clopidogrel can result in increased bleeding potential. Here we demonstrate that thrombosomes can circumvent or overcome this inhibition to restore hemostasis.

BACKGROUND

Antiplatelet drugs (also herein called antiplatelet agents) are common in the U.S. adult population and employ multiple mechanisms of inhibiting platelet action. Antiplatelet drugs are used to treat and/or prevent a number of cerebrovascular and cardiovascular diseases.

Antiplatelet drugs, however, are responsible for many adverse drug-related events (ADEs). Overdose and adverse events related to these drugs carry the risk of serious bleeding and related complications in the patient population. In addition, subjects treated with antiplatelet drugs face additional complications for surgery, as a subject may need to be tapered off the drugs before surgery, though cessation of therapy could put the subject at an increased risk for heart attack, stroke, or death.

There is therefore a need in the art for the treatment of coagulopathy, such as antiplatelet agent-induced coagulopathy, as well as a need for a solution for preparing subjects taking an anti-platelet drug for surgery.

SUMMARY OF THE INVENTION

Provided herein in some embodiments is a method of treating a coagulopathy in a subject, the method including administering to the subject in need thereof an effective amount of a composition including platelets or platelet derivatives and an incubating agent including one or more salts, a buffer, optionally a cryoprotectant, and optionally an organic solvent.

In some embodiments, provided herein is a method of treating a coagulopathy in a subject, the method including administering to the subject in need thereof an effective amount of a composition prepared by a process including incubating platelets with an incubating agent including one or more salts, a buffer, optionally a cryoprotectant, and optionally an organic solvent, to form the composition.

In some embodiments, provided herein is a method of restoring normal hemostasis in a subject, the method including administering to the subject in need thereof an effective amount of a composition including platelets or platelet derivatives and an incubating agent including one or more salts, a buffer, optionally a cryoprotectant, and optionally an organic solvent.

In some embodiments, provided herein is a method of restoring normal hemostasis in a subject, the method including administering to the subject in need thereof an effective amount of a composition prepared by a process including incubating platelets with an incubating agent including one or more salts, a buffer, optionally a cryoprotectant, and optionally an organic solvent, to form the composition.

In some embodiments, provided herein is a method of preparing a subject for surgery, the method including administering to the subject in need thereof an effective amount of a composition including platelets or platelet derivatives and an incubating agent including one or more salts, a buffer, optionally a cryoprotectant, and optionally an organic solvent. Implementations can include one or more of the following features. The surgery can be an emergency surgery. The surgery can be a scheduled surgery.

In some embodiments, provided herein is a method of preparing a subject for surgery, the method including administering to the subject in need thereof an effective amount of a composition prepared by a process including incubating platelets with an incubating agent including one or more salts, a buffer, optionally a cryoprotectant, and optionally an organic solvent, to form the composition. Implementations can include one or more of the following features. The surgery can be an emergency surgery. The surgery can be a scheduled surgery.

In some embodiments of the above methods, the subject has been treated or is being treated with an antiplatelet agent. In some embodiments, treatment with the antiplatelet agent can be stopped. In some embodiments, treatment with the antiplatelet agent can be continued.

In some embodiments, provided herein is a method of ameliorating the effects of an antiplatelet agent in a subject, the method including administering to the subject in need thereof an effective amount of a composition including platelets or platelet derivatives and an incubating agent including one or more salts, a buffer, optionally a cryoprotectant, and optionally an organic solvent.

In some embodiments, provided herein is a method of ameliorating the effects of an antiplatelet agent in a subject, the method including administering to the subject in need thereof an effective amount of a composition prepared by a process including incubating platelets with an incubating agent including one or more salts, a buffer, optionally a cryoprotectant, and optionally an organic solvent, to form the composition.

In some embodiments, the effects of the antiplatelet agent can be the result of an overdose of the antiplatelet agent.

In some embodiments, the antiplatelet agent can be selected from the group consisting of aspirin, cangrelor, ticagrelor, clopidogrel, prasugrel, eptifibatide, tirofiban, abciximab, and a supplement.

Some embodiments of any of the methods herein can include one or more of the following features. Administering can include administering topically. Administering can include administering parenterally. Administering can include administering intravenously. Administering can include administering intramuscularly. Administering can include administering intrathecally. Administering can include administering subcutaneously. Administering can include administering intraperitoneally. The composition can be dried prior to the administration step. The composition can be rehydrated following the drying step. The composition can be freeze-dried prior to the administration step. The composition can be rehydrated following the freeze-drying step. The incubating agent can include one or more salts selected from phosphate salts, sodium salts, potassium salts, calcium salts, magnesium salts, and a combination of two or more thereof. The incubating agent can include a carrier protein. The buffer can include HEPES, sodium bicarbonate ($NaHCO_3$), or a combination thereof. The composition can include one or more saccharides. The one or more saccharides can include trehalose. The one or more saccharides can include polysucrose. The one or more saccharides can include dextrose. The composition can include an organic solvent. The platelets or platelet derivatives can include thrombosomes.

DETAILED DESCRIPTION

Figure 1:
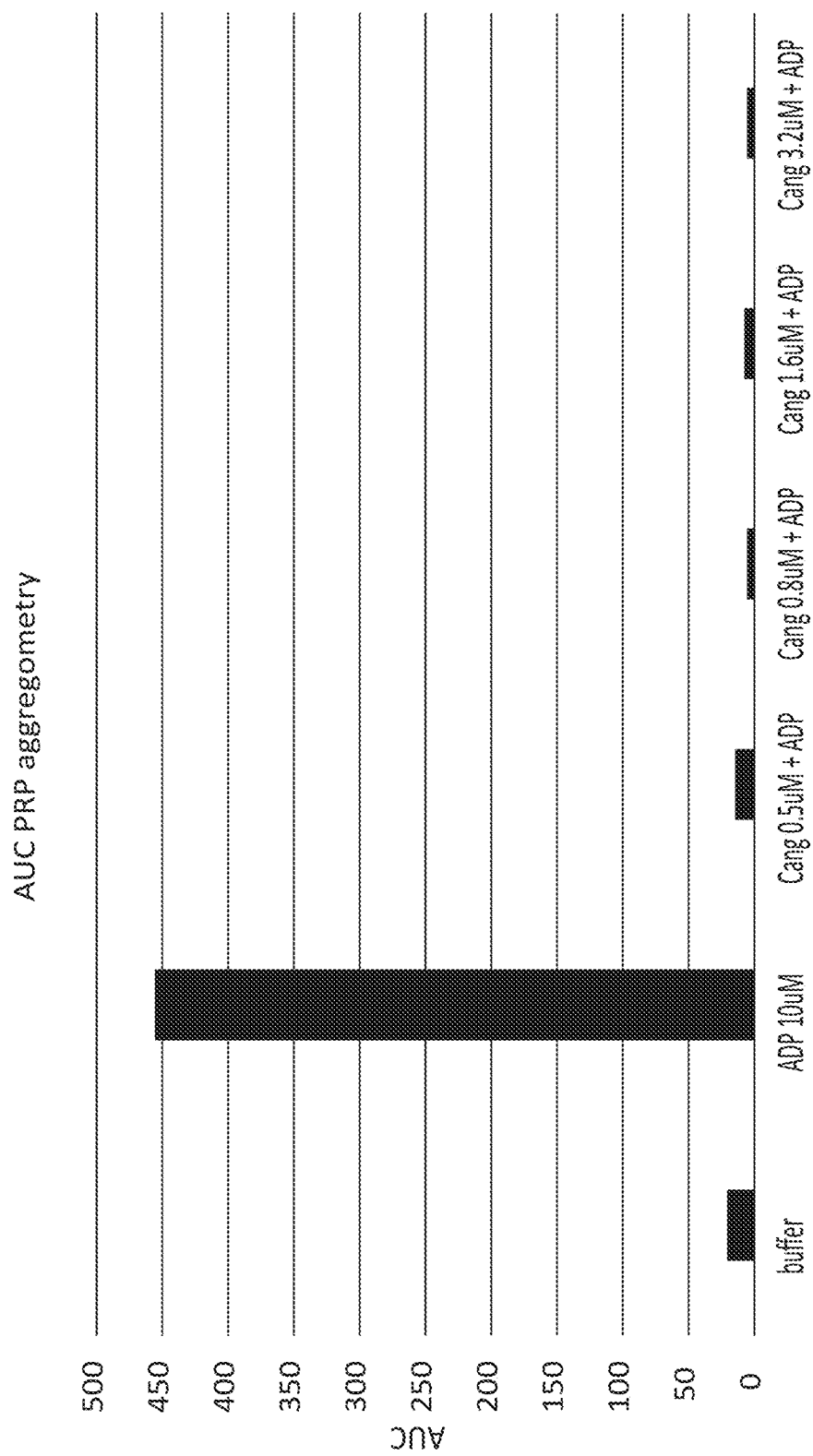
FIG. 1 shows transmission light aggregometry of cangrelor ("Cang") in platelet rich plasma, expressed as the integrated aggregation curve, induced by 10 μM adenosine diphosphate (ADP) activation with and without increasing concentrations of cangrelor.

Before embodiments of the present invention are described in detail, it is to be understood that the terminology used herein is for the purpose of describing particular embodiments only, and is not intended to be limiting. Unless defined otherwise, all technical and scientific terms used herein have the same meaning as commonly understood by one of ordinary skill in the art to which the term belongs. Although any methods and materials similar or equivalent to those described herein can be used in the practice of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a saccharide" includes reference to one or more saccharides, and equivalents thereof known to those skilled in the art. Furthermore, the use of terms that can be described using equivalent terms include the use of those equivalent terms. Thus, for example, the use of the term "subject" is to be understood to include the terms "patient", "person", "animal", "human", and other terms used in the art to indicate one who is subject to a medical treatment. The use of multiple terms to encompass a single concept is not to be construed as limiting the concept to only those terms used.

It is to be understood that the terminology used herein is for the purpose of describing particular embodiments only, and is not intended to be limiting. Further, where a range of values is disclosed, the skilled artisan will understand that all other specific values within the disclosed range are inherently disclosed by these values and the ranges they represent without the need to disclose each specific value or range herein. For example, a disclosed range of 1-10 includes 1-9,1-5, 2-10, 3.1-6, 1, 2, 3, 4, 5, and so forth. In addition, each disclosed range includes up to 5% lower for the lower value of the range and up to 5% higher for the higher value of the range. For example, a disclosed range of 4-10 includes 3.8-10.5. This concept is captured in this document by the term "about".

As used herein and in the appended claims, the term "platelet" can include whole platelets, fragmented platelets, platelet derivatives, or thrombosomes. "Platelets" within the above definition may include, for example, platelets in whole blood, platelets in plasma, platelets in buffer optionally supplemented with select plasma proteins, cold stored platelets, dried platelets, cryopreserved platelets, thawed cryopreserved platelets, rehydrated dried platelets, rehydrated cryopreserved platelets, lyopreserved platelets, thawed lyopreserved platelets, or rehydrated lyopreserved platelets. "Platelets" may be "platelets" of mammals, such as of humans, or such as of non-human mammals.

As used herein, "thrombosomes" (sometimes also herein called "Tsomes" or "Ts", particularly in the Examples and Figures) are platelet derivatives that have been treated with an incubating agent (e.g., any of the incubating agents described herein) and lyopreserved (such as freeze-dried). In some cases, thrombosomes can be prepared from pooled platelets. Thrombosomes can have a shelf life of 2-3 years in dry form at ambient temperature and can be rehydrated with sterile water within minutes for immediate infusion. One example of thrombosomes are THROMBOSOMES®, which are in clinical trials for the treatment of acute hemorrhage in thrombocytopenic patients. Typically, agents that inhibit Factor IIa, VIIa, IX, Xa, XI, Tissue Factor, or vitamin K-dependent synthesis of clotting factors (e.g., Factor II, VII, IX, or X) or that activate antithrombin (e.g., antithrombin III) are considered to be anticoagulants. Other mechanisms of anticoagulants are known. Anticoagulants include dabigatran, argatroban, hirudin, rivaroxaban, apixaban, edoxaban, fondaparinux, warfarin, heparin, and low molecular weight heparins.

As used herein, an "antiplatelet agent" is an antithrombotic and does not include anticoagulants. Examples of antiplatelet agents include aspirin (also called acetylsalicylic acid or ASA), cangrelor (e.g., KENGREAL®), ticagrelor (e.g., BRILINTA®), clopidogrel (e.g., PLAVIX®), prasugrel (e.g., EFFIENT®), eptifibatide (e.g., INTEGRILIN®), tirofiban (e.g., AGGRASTAT®), and abciximab (e.g., REOPRO®). For the purpose of this disclosure, antiplatelet agents include agents that inhibit P2Y receptors (e.g., $P2Y_{12}$), glycoprotein IIb/IIIa, or that antagonize thromboxane synthase or thromboxane receptors. Non-limiting examples of thromboxane $A_2$ antagonists are aspirin, terutroban, and picotamide. Non-limiting examples of P2Y receptor antagonists include cangrelor, ticagrelor, elinogrel, clopidogrel, prasugrel, and ticlopidine. Non-limiting examples of glycoprotein IIb/IIIa include abciximab, eptifibatide, and tirofiban. NSAIDS (e.g., ibuprofen) are also considered to be antiplatelet agents for the purposes of this disclosure. Other mechanisms of anti-platelet agents are known. Antiplatelet agents also include PAR1 antagonists, PAR4 antagonists GPVI antagonists and alpha2beta1 collagen receptor antagonists. Non-limiting examples of PAR-1 antagonists include vorapaxar and atopaxar. As used herein, aspirin is considered to be an antiplatelet agent but not an anticoagulant. Additional non-limiting examples of anti-platelet agents include cilostazol, prostaglandin E1, epoprostenol, dipyridamole, treprostinil sodium, and sarpogrelate.

In some embodiments, an antiplatelet agent can be selected from the group consisting of aspirin, cangrelor, ticagrelor, clopidogrel, prasugrel, eptifibatide, tirofiban, abciximab, and combinations thereof. In some embodiments, an antiplatelet agent can be selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, and combinations thereof. In some embodiments, an antiplatelet agent can be selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, sarpogrelate and combinations thereof. In some embodiments, the antiplatelet agent can include multiple antiplatelet agents, such as 2 (or more) of any of the antiplatelet agents described herein. In some embodiments, the antiplatelet agent can be aspirin and clopidogrel.

Cangrelor like clopidogrel, ticagrelor, and prasugrel, blocks the $P2Y_{12}$ (ADP) receptor on platelets. Cangrelor can in some cases be used as a representative of this class of drug. Cangrelor, unlike clopidogrel and prasugrel, does not need hepatic metabolism to become biologically active.

Eptifibatide is a peptide therapeutic that blocks the fibrin binding role of GPIIb-IIIa receptor on platelets. The drug is typically administered via IV as a 180 μg/kg bolus followed by 2 μg/kg/min continuous infusion. The blood concentration of eptifibatide is typically about 1-2 μM. Bleeding times generally return to normal within about 1 hour of drug stoppage.

Aspirin is an irreversible cylcooxygenase (COX) inhibitor. The COX enzyme in platelets is responsible for synthesis of thromboxane A2, prostaglandin E2 and prostacyclin (PGI2). Aspirin permanently inactivates the COX enzyme within platelets, and since platelets do not have the nuclear material to synthesize new enzyme, new platelets must be produced to overcome the aspirin effect. Without thromboxane A2, prostaglandin E2, and prostacyclin (PGI2) platelets are limited in their pro-aggregation activity. Many people are maintained on a low dose of aspirin to prevent unwanted clotting events. Aspirin bioavailability largely varies with administration route, with a single 500 mg dose IV at peaks of 500 μM and the same dose orally at 44 μM.

The antiplatelet class of drugs is widely used to prevent unwanted clotting episodes that lead to heart failure, stroke, and the like. In many cases, an antiplatelet drug may need to be reversed or stopped. In the case of advanced notice, as in a pre-planned surgery situation, the antiplatelet drug dose can sometimes be stopped before the surgery, preventing unwanted bleeding during surgery. In the case where an antiplatelet agent needs reversing quickly, reversal agents are typically not readily available, are expensive, or carry significant risk to the patient. In the case of need for rapid antiplatelet reversal, a platelet transfusion is typically administered, though the response to this is often only partial reversal. The caveat of this course of reversal is that the newly-infused platelets themselves are susceptible to circulating drug antiplatelet activity whereas, in some embodiments, compositions as described herein (e.g., including thrombosomes) are not. In some embodiments, compositions as described herein (e.g., including thrombosomes) are an active reversal agent. In some embodiments, the hemostatic activity of compositions as described herein (e.g., including thrombosomes) does not succumb to antiplatelet drugs.

Some exemplary antiplatelet agents and potential methods of reversal are described below.

Acetylsalicylic acid (ASA; aspirin)—aspirin acts as a COX-1 blocker in platelets, which renders the platelet inactive by irreversibly inhibiting platelet-derived thromboxane formation. Clinically, aspirin is sometimes reversed by a platelet transfusion in emergency situations or by stopping treatment where surgery is scheduled in the future.

Clopidogrel (e.g., PLAVIX®)—clopidogrel acts as to prevent ADP from binding to its receptor on platelets. ADP binding leads to platelet shape change and aggregation. Clopidogrel is non-reversible. Clinically, clopidogrel is sometimes reversed by a platelet transfusion in emergency situations or by stopping treatment where surgery is scheduled in the future.

Cangrelor (e.g., KENGREAL®)—cangrelor acts to prevent ADP from binding to its receptor on platelets. ADP binding leads to platelet shape change and aggregation. Clopidogrel is reversible and platelet function is returned approximately 1 hour after stopping infusion. Clinically it is generally preferred when reversal is needed after a procedure.

Ticagrelor (e.g., BRILINTA®)—ticagrelor acts to prevent ADP from binding to its receptor and acts as an inverse agonist. Ticagrelor is reversible and platelet function can return after approximately 72 hours of the last dosage. Reversal of action of ticagrelor can be affected by the time after the last dose. If the last dose was longer than 24 hours previous, then platelet transfusion can sometimes be therapeutic to reverse the results.

Effient (e.g., PRASUGREL®)—Effient acts to prevent ADP from binding to its receptor and acts as a non-reversable antagonist. It being a non-reversible antagonist, new platelets must be formed to overcome its effect. Clinically Effient is reversed by a platelet transfusion in emergency situations or by stopping treatment where surgery is scheduled in the future.

Eptifibatide (Integrilin)—Eptifibatide acts to block the GpIIb/IIIa and acts as a reversible antagonist. Clinically, Integrilin is reversed by a platelet transfusion in emergency situations or by stopping treatment where surgery is scheduled in the future.

Platelets infusions are currently used as a treatment method for antiplatelet drugs, but platelet transfusions only act to dilute out the effect of these drugs. In some embodiments, thrombosomes are not reactive to these drugs and maintain their ability to aid in clotting. This makes treatment via thrombosomes entirely unique and introduces a new application for the product.

Platelet-derived products are not currently used as a treatment method for anticoagulant/antiplatelet drugs, and there are no currently approved reversal agents for antiplatelet agents. As such, emergency treatments (pre-op, trauma, and the like) are typically blanket precautions to avoid or mitigate hemorrhage. Non-limiting examples include infusion of plasma, red blood cells, and anti-fibrinolytics. Platelet derivatives (e.g., lyopreserved platelets (e.g., thrombosomes)) may be an effective alternative or supplement to these general treatments.

Without being bound by any particular theory, it is believed that thrombosomes can work at least in part by providing a procoagulant negatively charged surface to augment thrombin generation above and beyond that suppressed by the anti-coagulants. Similarly, without being bound by any particular theory, it is believed that thrombosomes can work at least in part by binding to and co-aggregating with circulating platelets.

Products and methods are described herein for controlling bleeding and improving healing. The products and methods described herein can also be used to counteract the activity of an antiplatelet agent (e.g., aspirin (also called acetylsalicylic acid or ASA), cangrelor (e.g., KENGREAL®), ticagrelor (e.g., BRILINTA®), clopidogrel (e.g., PLAVIX®), prasugrel (e.g., EFFIENT®), eptifibatide (e.g., INTEGRILIN®), tirofiban (e.g., AGGRASTAT®), or abciximab (e.g., REOPRO®)). The products and methods described herein are directed toward embodiments that can aid in the closure and healing of wounds.

In certain embodiments, a composition comprising platelets such as lyophilized platelets or platelet derivatives may be delivered to a wound on the surface of or in the interior of a patient. In various embodiments, a composition comprising platelets such as lyophilized platelets or platelet derivatives can be applied in selected forms including, but not limited to, adhesive bandages, compression bandages, liquid solutions, aerosols, matrix compositions, and coated sutures or other medical closures. In embodiments, a composition comprising platelets such as lyophilized platelets or platelet derivatives may be administered to all or only a portion of an affected area on the surface of a patient. In other embodiments, a composition comprising platelets such as lyophilized platelets or platelet derivatives may be administered systemically, for example via the blood stream. In embodiments, an application of the platelet derivative can produce hemostatic effects for 2 or 3 days, preferably 5 to 10 days, or most preferably for up to 14 days.

Some embodiments provide a method of treating a coagulopathy in a subject, the method comprising administering to the subject in need thereof an effective amount of a composition comprising platelets such as lyophilized platelets or platelet derivatives and an incubating agent comprising one or more salts, a buffer, optionally a cryoprotectant (also called a lyophilizing agent), and optionally an organic solvent.

Some embodiments provide a method of treating a coagulopathy in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

In some embodiments of any of the methods described herein, the coagulopathy is the result of an antiplatelet agent.

Some embodiments provide a method of treating coagulopathy in a subject, wherein the subject has been treated or is being treated with an antiplatelet agent, the method comprising administering to the subject in need thereof an effective amount of a composition comprising platelets such as lyophilized platelets or platelet derivatives and an incubating agent comprising one or more salts, a buffer, optionally a cryoprotectant, and optionally an organic solvent.

Some embodiments provide a method of treating coagulopathy in a subject, wherein the subject has been treated or is being treated with an antiplatelet agent, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Some embodiments provide a method of restoring normal hemostasis in a subject, the method comprising administering to the subject in need thereof an effective amount of a composition comprising platelets such as lyophilized platelets or platelet derivatives and an incubating agent comprising one or more salts, a buffer, optionally a cryoprotectant, and optionally an organic solvent.

Some embodiments provide a method of restoring normal hemostasis in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Some embodiments provide a method of restoring normal hemostasis in a subject, wherein the subject has been treated or is being treated with an antiplatelet agent, the method comprising administering to the subject in need thereof an effective amount of a composition comprising platelets such as lyophilized platelets or platelet derivatives and an incubating agent comprising one or more salts, a buffer, optionally a cryoprotectant, and optionally an organic solvent.

Some embodiments provide a method of restoring normal hemostasis in a subject, wherein the subject has been treated or is being treated with an antiplatelet agent, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Compositions as described herein can also be administered to prepare a subject for surgery, in some cases. For some patients taking an antiplatelet agent, it may be difficult or impossible to reduce the dosage of the antiplatelet agent before surgery (e.g., in the case of trauma or other emergency surgery). For some patients taking an antiplatelet agent, it may be inadvisable to reduce the dosage of the antiplatelet agent before surgery (e.g., if the patient would be at risk of a thrombotic event (e.g., deep vein thrombosis, pulmonary embolism, or stroke) if the dosage of the antiplatelet agent were reduced over time.

Accordingly, some embodiments provide a method of preparing a subject for surgery, the method comprising administering to the subject in need thereof an effective amount of a composition comprising platelets such as lyophilized platelets or platelet derivatives and an incubating agent comprising one or more salts, a buffer, optionally a cryoprotectant, and optionally an organic solvent.

Some embodiments provide a method of preparing a subject for surgery, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Some embodiments provide a method of preparing a subject for surgery, wherein the subject has been treated or is being treated with an antiplatelet agent, the method comprising administering to the subject in need thereof an effective amount of a composition comprising platelets such as lyophilized platelets or platelet derivatives and an incubating agent comprising one or more salts, a buffer, optionally a cryoprotectant, and optionally an organic solvent.

Some embodiments provide a method of preparing a subject for surgery, wherein the subject has been treated or is being treated with an antiplatelet agent, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

In some embodiments, a surgery can be an emergency surgery (e.g., in the case of trauma) or a scheduled surgery.

In some embodiments, treatment with an anticoagulant can be stopped (e.g., in preparation for surgery). In some embodiments, treatment with an anticoagulant can continue.

Some embodiments provide a method of ameliorating the effects of an antiplatelet agent in a subject, the method comprising administering to the subject in need thereof an effective amount of a composition comprising platelets such as lyophilized platelets or platelet derivatives and an incubating agent comprising one or more salts, a buffer, optionally a cryoprotectant, and optionally an organic solvent.

Some embodiments provide a method of ameliorating the effects of an antiplatelet agent in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

In some cases, the effects of an antiplatelet agent may need to be ameliorated due to an incorrect dosage of an antiplatelet agent. For example, in some embodiments, the effects of an antiplatelet agent can be ameliorated following an overdose of the antiplatelet agent. In some cases, the effects of an antiplatelet agent may need to be ameliorated due to a potential for interaction with another drug (e.g., a second antiplatelet agent). For example, in some embodiments, the effects of an antiplatelet agent can be ameliorated following an erroneous dosing of two or more drugs, at least one of which is an antiplatelet agent.

In some embodiments of any of the methods described herein, the composition can further comprise an active agent, such as an anti-fibrinolytic agent. Non-limiting examples of anti-fibrinolytic agents include ε-aminocaproic acid (EACA), tranexamic acid, aprotinin, aminomethylbenzoic acid, and fibrinogen. In some embodiments, platelets or platelet derivatives can be loaded with an active agent, such as an anti-fibrinolytic agent.

Clotting parameters of blood (e.g., the subject's blood) can be assessed at any appropriate time during the methods described herein. For example, one or more clotting parameters of blood can be assessed before administration of a composition comprising platelets such as lyophilized platelets or platelet derivatives as described herein, e.g., in order to determine the need for administration of a composition comprising platelets or platelet derivatives as described herein. As another example, one or more clotting parameters of blood can be assessed after administration of a composition comprising platelets or platelet derivatives as described herein, e.g., in order to determine the effectiveness of the administered composition, to determine whether additional administration of the composition is warranted, or to determine whether it is safe to perform a surgical procedure.

Accordingly, any of the methods described herein can include steps of assessing one or more clotting parameters of blood before administration of a composition comprising platelets or platelet derivatives as described herein, assessing one or more clotting parameters of blood after administration of a composition comprising platelets or platelet derivatives as described herein, or both.

Any appropriate method can be used to assess clotting parameters of blood. Non-limiting examples of methods include the prothrombin time assay, international normalized ratio (INR), thrombin generation (TGA; which can be used to generate parameters such as, e.g., peak thrombin, endogenous thrombin potential (ETP), and lag time), thromboelastography (TEG), activated clotting time (ACT), and partial thromboplastin time (PTT or aPTT).

Thrombin Generation

The thrombin generation assay measured the production of thrombin after sample activation via a pro-coagulation agent resulting of thrombin enzymatic cleavage of a fluorescent peptide and release of fluorescent molecule. The peak thrombin is a measure of the maximum thrombin produced, lag time the time to start of thrombin production and ETP as the total thrombin potentially produced.

In some embodiments, a patient can have a peak thrombin of about 60 nM to about 170 nM, such as about 65 nM to about 170 nM, such as about 65 nM to about 120 nM, such as about 80 nM, before administration of a composition comprising platelets or platelet derivatives as described herein.

TEG assesses intrinsic hemostasis via plots of clot strength over time. Calcium chloride ($CaCl_2$) is typically used as the initiating reagent. A TEG waveform (see, e.g., FIG. 16) has multiple parameters that can provide information about clotting.

R-time=reaction time(s)–time of latency from start of test to initial fibrin formation.

K=kinetics(s)–speed of initial fibrin formation,time taken to achieve a certain level of clot strength (e.g., an amplitude of 20 mm)

alpha angle=slope of line between R and K–measures the rate of clot formation.

MA=maximum amplitude(mm)–represents the ultimate strength of the fibrin clot.

$A_{30}$=amplitude 30 minutes after maximum amplitude is reached–represents rate of lysis phase.

In hypocoagulable blood states, R-time increases and MA decreases. R-time typically provides a broader response range than MA.

In the Total Thrombus-formation Analysis System (T-TAS®, FUJIMORI KOGYO CO., LTD), the sample is forced through collagen-coated microchannels using mineral oil. Changes in pressure are used to assess thrombus formation. The Occlusion Start Time is time it takes to reach 10 kPa, and the Occlusion Time=time it takes to each Δ80 kPa using an AR chip (e.g., Zacros Item No, TC0101). According to the manufacturer, an AR chip can be used for analyzing the formation of a mixed white thrombus consisting chiefly of fibrin and activated platelets. It has a flow path (300 μm wide by 50 μm high) coated with collagen and tissue factors and can be used to analyze the clotting function and platelet function. In comparison, a PL chip can be used for analyzing the formation of a platelet thrombus consisting chiefly of activated platelets. A PL chip has a flow path coated with collagen only and can be used to analyze the platelet function.

The ACT assay is the most basic, but possibly most reliable, way to measure clotting time ($t_{ACT}$), determined by a magnet's resistance to gravity as a clot forms around it. Typical donor blood has a $t_{ACT}$~200-300 s using only $CaCl_2$.

Some embodiments provide a method of increasing thrombin generation in a subject, the method comprising administering to the subject in need thereof an effective amount of a composition comprising platelets such as lyophilized platelets or platelet derivatives and an incubating agent comprising one or more salts, a buffer, optionally a cryoprotectant, and optionally an organic solvent.

Some embodiments, provide a method of increasing thrombin generation in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Some embodiments provide a method of increasing peak thrombin in a subject, the method comprising administering to the subject in need thereof an effective amount of a composition comprising platelets such as lyophilized platelets or platelet derivatives and an incubating agent comprising one or more salts, a buffer, optionally a cryoprotectant, and optionally an organic solvent.

Some embodiments provide a method of increasing peak thrombin in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

In some embodiments, prior to the administering, the peak thrombin of the subject was below 66 nM (e.g., below 64 nM, 62 nM, 60 nM, 55 nM, 50 nM, 45 nM, 40 nM, 35 nM, 30 nM, 25 nM, 20 nM, 15 nM, 10 nM, or 5 nM). In some embodiments, after the administering, the peak thrombin of the subject is above 66 nM (e.g., above 68 nM, 70 nM, 75 nM, 80 nM, 85 nM, 90 nM, 95 nM, 100 nM, 110 nM, 120 nM, 130 nM, 140 nM, or 150 nM). In some embodiments, after the administering, the peak thrombin of the subject is between 66 and 166 nM. Peak thrombin can be measured by any appropriate method.

An "effective amount" as used herein is an amount of the composition that comprises an amount of platelets such as lyophilized platelets or platelet derivatives (e.g., thrombosomes) effective in treating the subject. Such an amount of platelets or platelet derivatives (e.g., thrombosomes) includes any appropriate dosage of a composition comprising platelets or platelet derivatives as described herein that can be administered to the subject. For example, in some embodiments, a dose of a composition comprising platelets or platelet derivatives (e.g., thrombosomes) can include about $1.0 \times 10^7$ particles to about $1.0 \times 10^{10}$ particles, such as about $1.6 \times 10^7$ particles (e.g., thrombosomes)/kg to about $1.0 \times 10^{10}$ particles/kg (e.g., about $1.6 \times 10^7$ to about $5.1 \times 10^9$ particles/kg, about $1.6 \times 10^7$ to about $3.0 \times 10^9$ particles/kg, about $1.6 \times 10^7$ to about $1.0 \times 10^9$ particles/kg, about $1.6 \times 10^7$ to about $5.0 \times 10^8$ particles/kg, about $1.6 \times 10^7$ to about $1.0 \times 10^8$ particles/kg, about $1.6 \times 10^7$ to about $5.0 \times 10^7$ particles/kg, about $5.0 \times 10^7$ to about $1.0 \times 10^8$ particles/kg, about $1.0 \times 10^8$ to about $5.0 \times 10^8$ particles/kg, about $5.0 \times 10^8$ to about $1.0 \times 10^9$ particles/kg, about $1.0 \times 10^9$ to about $5.0 \times 10^9$ particles/kg, or about $5.0 \times 10^9$ to about $1.0 \times 10^{10}$ particles/kg).

In some embodiments of the methods herein, the composition is administered topically. In some embodiments, topical administration can include administration via a solution, cream, gel, suspension, putty, particulates, or powder. In some embodiments, topical administration can include administration via a bandage (e.g. an adhesive bandage or a compression bandage) or medical closure (e.g., sutures, staples)); for example the platelet derivatives (e.g., lyopreserved platelets (e.g., thrombosomes)) can be embedded therein or coated thereupon), as described in PCT Publication No. WO2017/040238 (e.g., paragraphs [013]-[069]), corresponding to U.S. patent application Ser. No. 15/776,255, the entirety of which is herein incorporated by reference.

In some embodiments of the methods herein, the composition is administered parenterally.

In some embodiments of the methods herein, the composition is administered intravenously.

In some embodiments of the methods herein, the composition is administered intramuscularly.

In some embodiments of the methods herein, the composition is administered intrathecally.

In some embodiments of the methods herein, the composition is administered subcutaneously.

In some embodiments of the methods herein, the composition is administered intraperitoneally.

In some embodiments of the methods herein, the composition is dried prior to the administration step. In some embodiments of the method, the composition is freeze-dried prior to the administration step. In some embodiments of the method, the composition is rehydrated following the drying or freeze-drying step.

In some embodiments, the antiplatelet agent is selected from the group consisting of aspirin (also called acetylsalicylic acid or ASA); a P2Y12 inhibitor such as cangrelor (e.g., KENGREAL®), ticagrelor (e.g., BRILINTA®), clopidogrel (e.g., PLAVIX®), or prasugrel (e.g., EFFIENT®); a glycoprotein IIb/IIIa inhibitor such as eptifibatide (e.g., INTEGRILIN®), tirofiban (e.g., AGGRASTAT®), or abciximab (e.g., REOPRO®)); supplements such as herbal supplements; or a combination of any thereof. Examples of supplements include ginger, ginseng, ginkgo, green tea, kava, saw palmetto, boldo (*Peumus boldus*), Danshen (*Salvia miltiorrhiza*), Dong quai (*Angelica sinensis*) papaya (*Carica papaya*), fish oil, and vitamin E. Examples of herbal supplements include ginger, ginseng, and ginkgo.

In some embodiments, the antiplatelet agent is aspirin.

In some embodiments, the antiplatelet agent is cangrelor (e.g., KENGREAL®).

In some embodiments, the antiplatelet agent is ticagrelor (e.g., BRILINTA®).

In some embodiments, the antiplatelet agent is clopidogrel (e.g., PLAVIX®).

In some embodiments, the antiplatelet agent is prasugrel (e.g., EFFIENT®).

In some embodiments, the antiplatelet agent is eptifibatide (e.g., INTEGRILIN®).

In some embodiments, the antiplatelet agent is tirofiban (e.g., AGGRASTAT®).

In some embodiments, the antiplatelet agent is abciximab (e.g., REOPRO®).

In some embodiments, the antiplatelet agent is terutroban.

In some embodiments, the antiplatelet agent is picotamide.

In some embodiments, the antiplatelet agent is elinogrel.

In some embodiments, the antiplatelet agent is ticlopidine.

In some embodiments, the antiplatelet agent is ibuprofen.

In some embodiments, the antiplatelet agent is vorapaxar.

In some embodiments, the antiplatelet agent is atopaxar.

In some embodiments, the antiplatelet agent is cilostazol.

In some embodiments, the antiplatelet agent is prostaglandin E1.

In some embodiments, the antiplatelet agent is epoprostenol.

In some embodiments, the antiplatelet agent is dipyridamole.

In some embodiments, the antiplatelet agent is treprostinil sodium.

In some embodiments, the antiplatelet agent is sarpogrelate.

In some embodiments, the antiplatelet agent is a supplement.

In some embodiments, the antiplatelet agent is an herbal supplement.

In some embodiments, rehydrating the composition comprising platelets or platelet derivatives comprises adding to the platelets an aqueous liquid. In some embodiments, the aqueous liquid is water. In some embodiments, the aqueous liquid is an aqueous solution (e.g., a buffer). In some embodiments, the aqueous liquid is a saline solution. In some embodiments, the aqueous liquid is a suspension.

In some embodiments, the rehydrated platelets or platelet derivatives (e.g., thrombosomes) have coagulation factor levels showing all individual factors (e.g., Factors VII, VIII and IX) associated with blood clotting at 40 international units (IU) or greater.

In some embodiments, the platelets such as lyophilized platelets or platelet derivatives (e.g., thrombosomes) have less than about 10%, such as less than about 8%, such as less than about 6%, such as less than about 4%, such as less than about 2%, such as less than about 0.5% crosslinking of platelet membranes via proteins and/or lipids present on the membranes. In some embodiments, the rehydrated platelets or platelet derivatives (e.g., thrombosomes), have less than about 10%, such as less than about 8%, such as less than about 6%, such as less than about 4%, such as less than about 2%, such as less than about 0.5% crosslinking of platelet membranes via proteins and/or lipids present on the membranes.

In some embodiments, the platelets such as lyophilized platelets or platelet derivatives (e.g., thrombosomes) have a particle size (e.g., diameter, max dimension) of at least about 0.2 µm (e.g., at least about 0.3 µm, at least about 0.4 µm, at least about 0.5 µm, at least about 0.6 µm, at least about 0.7 µm, at least about 0.8 µm, at least about 0.9 µm, at least about 1.0 µm, at least about 1.2 µm, at least about 1.5 µm, at least about 2.0 µm, at least about 2.5 µm, or at least about 5.0 µm). In some embodiments, the particle size is less than about 5.0 µm (e.g., less than about 2.5 µm, less than about 2.0 µm, less than about 1.5 µm, less than about 1.0 µm, less than about 0.9 µm, less than about 0.8 µm, less than about 0.7 µm, less than about 0.6 µm, less than about 0.5 µm, less than about 0.4 µm, or less than about 0.3 µm). In some embodiments, the particle size is from about 0.3 µm to about 5.0 µm (e.g., from about 0.4 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm).

In some embodiments, at least 50% (e.g., at least about 55%, at least about 60%, at least about 65%, at least about 70%, at least about 75%, at least about 80%, at least about 85%, at least about 90%, at least about 95%, or at least about 99%) of platelets such as lyophilized platelets or platelet derivatives (e.g., thrombosomes), have a particle size in the range of about 0.3 µm to about 5.0 µm (e.g., from about 0.4 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm). In some embodiments, at most 99% (e.g., at most about 95%, at most about 80%, at most about 75%, at most about 70%, at most about 65%, at most about 60%, at most about 55%, or at most about 50%) of the platelets such as lyophilized platelets or platelet derivatives (e.g., thrombosomes), are in the range of about 0.3 µm to about 5.0 µm (e.g., from about 0.4 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm). In some embodiments, about 50% to about 99% (e.g., about 55% to about 95%, about 60% to about 90%, about 65% to about 85, about 70% to about 80%) of the platelets or platelet derivatives (e.g., thrombosomes) are in the range of about 0.3 µm to about 5.0 µm (e.g., from about 0.4 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm).

In some embodiments, platelets are isolated, for example in a liquid medium, prior to treating a subject.

In some embodiments, platelets are donor-derived platelets. In some embodiments, platelets are obtained by a process that comprises an apheresis step. In some embodiments, platelets are pooled platelets.

In some embodiments, platelets are pooled from a plurality of donors. Such platelets pooled from a plurality of donors may be also referred herein as pooled platelets. In some embodiments, the donors are more than 5, such as more than 10, such as more than 20, such as more than 50, such as up to about 100 donors. In some embodiments, the donors are from about 5 to about 100, such as from about 10 to about 50, such as from about 20 to about 40, such as from about 25 to about 35. Pooled platelets can be used to make any of the compositions described herein.

In some embodiments, platelets are derived in vitro. In some embodiments, platelets are derived or prepared in a culture. In some embodiments, preparing the platelets comprises deriving or growing the platelets from a culture of megakaryocytes. In some embodiments, preparing the platelets comprises deriving or growing the platelets (or megakaryocytes) from a culture of human pluripotent stem cells (PCSs), including embryonic stem cells (ESCs) and/or induced pluripotent stem cells (iPSCs).

Accordingly, in some embodiments, platelets are prepared prior to treating a subject as described herein. In some embodiments, the platelets are lyophilized. In some embodiments, the platelets are cryopreserved.

In some embodiments, the platelets or pooled platelets may be acidified to a pH of about 6.0 to about 7.4 prior to the incubation with the incubating agent. In some embodiments, the method comprises acidifying the platelets to a pH of about 6.5 to about 6.9. In some embodiments, the method comprises acidifying the platelets to a pH of about 6.6 to about 6.8. In some embodiments, the acidifying comprises adding to the pooled platelets a solution comprising Acid Citrate Dextrose (ACD).

In some embodiments, the platelets are isolated prior to the incubation with the incubating agent. In some embodiments, the method further comprises isolating platelets by using centrifugation. In some embodiments, the centrifugation occurs at a relative centrifugal force (RCF) of about 1000×g to about 2000×g. In some embodiments, the centrifugation occurs at relative centrifugal force (RCF) of about 1300×g to about 1800×g. In some embodiments, the centrifugation occurs at relative centrifugal force (RCF) of about 1500×g. In some embodiments, the centrifugation occurs for about 1 minute to about 60 minutes. In some embodiments, the centrifugation occurs for about 10 minutes to about 30 minutes. In some embodiments, the centrifugation occurs for about 30 minutes.

An incubating agent can include any appropriate components. In some embodiments, the incubating agent may comprise a liquid medium. In some embodiments the incubating agent may comprise one or more salts selected from phosphate salts, sodium salts, potassium salts, calcium salts, magnesium salts, and any other salt that can be found in blood or blood products, or that is known to be useful in drying platelets, or any combination of two or more of these.

In some embodiments, the incubating agent comprises one or more salts, such as phosphate salts, sodium salts, potassium salts, calcium salts, magnesium salts, and any other salt that can be found in blood or blood products. Exemplary salts include sodium chloride (NaCl), potassium chloride (KCl), and combinations thereof. In some embodiments, the incubating agent includes from about 0.5 mM to about 100 mM of the one or more salts. In some embodiments, the incubating agent includes from about 0.5 mM to about 100 mM (e.g., about 0.5 to about 2 mM, about 2 mM to about 90 mM, about 2 mM to about 6 mM, about 50 mM to about 100 mM, about 60 mM to about 90 mM, about 70 to about 85 mM) about of the one or more salts. In some embodiments, the incubating agent includes about 5 mM, about 60 mM, about 65 mM, about 70 mM, about 75 mM, or about 80 mM of the one or more salts. In some embodiments, the incubating agent comprises one or more salts selected from calcium salts, magnesium salts, and a combination of the two, in a concentration of about 0.5 mM to about 2 mM.

Preferably, these salts are present in the composition comprising platelets or platelet derivatives, such as freeze-dried platelets, at an amount that is about the same as is found in whole blood.

In some embodiments, the incubating agent further comprises a carrier protein. In some embodiments, the carrier protein comprises human serum albumin, bovine serum albumin, or a combination thereof. In some embodiments, the carrier protein is present in an amount of about 0.05% to about 1.0% (w/v).

The incubating agent may be any buffer that is non-toxic to the platelets and provides adequate buffering capacity to the solution at the temperatures at which the solution will be exposed during the process provided herein. Thus, the buffer may comprise any of the known biologically compatible buffers available commercially, such as phosphate buffers, such as phosphate buffered saline (PBS), bicarbonate/carbonic acid, such as sodium-bicarbonate buffer, N-2-hydroxyethylpiperazine-N'-2-ethanesulfonic acid (HEPES), and tris-based buffers, such as tris-buffered saline (TBS). Likewise, it may comprise one or more of the following buffers: propane-1,2,3-tricarboxylic (tricarballylic); benzenepentacarboxylic; maleic; 2,2-dimethylsuccinic; EDTA; 3,3-dimethylglutaric; bis(2-hydroxyethyl)imino-tris(hydroxymethyl)-methane (BIS-TRIS); benzenehexacarboxylic (mellitic); N-(2-acetamido)imino-diacetic acid (ADA); butane-1,2,3,4-tetracarboxylic; pyrophosphoric; 1,1-cyclopentanediacetic (3,3 tetramethylene-glutaric acid); piperazine-1,4-bis-(2-ethanesulfonic acid) (PIPES); N-(2-acetamido)-2-amnoethanesulfonic acid (ACES); 1,1-cyclohexanediacetic; 3,6-endomethylene-1,2,3,6-tetrahydrophthalic acid (EMTA; ENDCA); imidazole; 2-(aminoethyl)trimethylammonium chloride (CHOLAMINE); N,N-bis(2-hydroxyethyl)-2-aminoethanesulfonic acid (BES); 2-methylpropane-1,2,3-triscarboxylic (beta-methyl tricarballylic); 2-(N-morpholino)propanesulfonic acid (MOPS); phosphoric; and N-tris(hydroxymethyl)methyl-2-amminoethane sulfonic acid (TES). In some embodiments, the incubating agent includes one or more buffers, e.g., N-2-hydroxyethylpiperazine-N'-2-ethanesulfonic acid (HEPES), or sodium-bicarbonate (NaHCO$_3$). In some embodiments, the incubating agent includes from about 5 to about 100 mM of the one or more buffers. In some embodiments, the incubating agent includes from about 5 to about 50 mM (e.g., from about 5 mM to about 40 mM, from about 8 mM to about 30 mM, about 10 mM to about 25 mM) about of the one or more buffers. In some embodiments, the incubating agent includes about 10 mM, about 20 mM, about 25 mM, or about 30 mM of the one or more buffers.

In some embodiments, the incubating agent includes one or more saccharides, such as monosaccharides and disaccharides, including sucrose, maltose, trehalose, glucose, mannose, dextrose, and xylose. In some embodiments, the saccharide is a monosaccharide. In some embodiments, the saccharide is a disaccharide. In some embodiments, the saccharide comprises a monosaccharide, a disaccharide, or a combination thereof. In some embodiments, the saccharide is a non-reducing disaccharide. In some embodiments, the saccharide comprises sucrose, maltose, trehalose, glucose (e.g., dextrose), mannose, or xylose. In some embodiments, the saccharide comprises trehalose. In some embodiments, the incubating agent comprises a starch. In some embodiments, the incubating agent includes polysucrose, a polymer of sucrose and epichlorohydrin. In some embodiments, the incubating agent includes from about 10 mM to about 1,000 mM of the one or more saccharides. In some embodiments, the incubating agent includes from about 50 to about 500 mM of the one or more saccharides. In embodiments, one or more saccharides is present in an amount of from 10 mM 10 to 500 mM. In some embodiments, one or more saccharides is present in an amount of from 50 mM to 200 mM. In embodiments, one or more saccharides is present in an amount from 100 mM to 150 mM. In some embodiments, the one or more saccharides is the lyophilizing agent; for example, in some embodiments, the lyophilizing agent comprises trehalose, polysucrose, or a combination thereof.

In some embodiments the composition comprising platelets or platelet derivatives, (e.g., thrombosomes), may comprise one or more of water or a saline solution. In some embodiments the composition comprising platelets or platelet derivatives, such as freeze-dried platelets, may comprise DMSO.

In some embodiments, the incubating agent comprises an organic solvent, such as an alcohol (e.g., ethanol). In such an incubating agent, the amount of solvent can range from 0.1% to 5.0% (v/v). In some embodiments, the organic solvent can range from about 0.1% (v/v) to about 5.0% (v/v), such as from about 0.3% (v/v) to about 3.0% (v/v), or from about 0.5% (v/v) to about 2% (v/v).

In some embodiments, suitable organic solvents include, but are not limited to alcohols, esters, ketones, ethers, halogenated solvents, hydrocarbons, nitriles, glycols, alkyl nitrates, water or mixtures thereof. In some embodiments, suitable organic solvents includes, but are not limited to methanol, ethanol, n-propanol, isopropanol, acetic acid, acetone, methyl ethyl ketone, methyl isobutyl ketone, methyl acetate, ethyl acetate, isopropyl acetate, tetrahydrofuran, isopropyl ether (IPE), tert-butyl methyl ether, dioxane (e.g., 1,4-dioxane), acetonitrile, propionitrile, methylene chloride, chloroform, toluene, anisole, cyclohexane, hexane, heptane, ethylene glycol, nitromethane, dimethylformamide, dimethyl sulfoxide, N-methyl pyrrolidone, dimethylacetamide, and combinations thereof. In some embodiments the organic solvent is selected from the group consisting of ethanol, acetic acid, acetone, acetonitrile, dimethylformamide, dimethyl sulfoxide (DMSO), dioxane, methanol, n-propanol, isopropanol, tetrahydrofuran (THF), N-methyl pyrrolidone, dimethylacetamide (DMAC), or combinations thereof. In some embodiments, the organic solvent comprises ethanol, DMSO, or a combination thereof. The presence of organic solvents, such as ethanol, can be beneficial in the processing of platelets, platelet derivatives, or thrombosomes (e.g., freeze-dried platelet derivatives).

In some embodiments the incubating agent is incubated into the platelets in the presence of an aqueous medium. In some embodiments the incubating agent is incubated in the presence of a medium comprising DMSO.

In some embodiments, one or more other components may be incubated in the platelets. Exemplary components may include Prostaglandin E1 or Prostacyclin and or EDTA/EGTA to prevent platelet aggregation and activation during the incubating process.

Non-limiting examples of incubating agent compositions that may be used are shown in Tables 1-5.

TABLE 1

Buffer

| Component | Concentration (mM unless otherwise specified) |
|---|---|
| NaCl | 75.0 |
| KCl | 4.8 |
| HEPES | 9.5 |
| NaHCCO$_3$ | 12.0 |
| Dextrose | 3 |
| Trehalose | 100 |
| Ethanol (optional) | 1% (v/v) |

TABLE 2

Buffer A

| Component | Concentration (mM unless specified otherwise) |
|---|---|
| CaCl$_2$ | 1.8 |
| MgCl$_2$ | 1.1 |
| KCl | 2.7 |
| NaCl | 137 |
| NaH$_2$PO$_4$ | 0.4 |
| HEPES | 10 |
| D-glucose | 5.6 |
| pH | 6.5 |

TABLE 3

Buffer B

| Component | Concentration (mM unless otherwise specified) |
|---|---|
| Buffer and Salts | Table 4 (below) |
| BSA | 0.35% |
| Dextrose | 5 |
| pH | 7.4 |

Table 3. Buffer B can be used when incubating platelets, e.g., for flow cytometry. Such an incubation can be done at room temperature in the dark. Albumin is an optional component of Buffer B.

TABLE 4

Concentration of HEPES and of Salts in Buffer B

| Component | Concentration (mM unless otherwise specified) |
|---|---|
| HEPES | 25 |
| NaCl | 119 |
| KCl | 5 |
| CaCl$_2$ | 2 |
| MgCl$_2$ | 2 |
| glucose | 6 g/l |

Table 4 is another exemplary incubating agent. The pH can be adjusted to 7.4 with NaOH. Albumin is an optional component of Buffer B.

TABLE 5

Tyrode's HEPES Buffer (plus PGE1)

| Component | Concentration (mM) |
|---|---|
| CaCl$_2$ | 1.8 |
| MgCl$_2$ | 1.1 |
| KCl | 2.7 |
| NaCl | 137 |
| NaH$_2$PO$_4$ | 0.4 |
| HEPES | 10 |
| D-glucose | 5.6 |
| pH | 6.5 |
| Prostagalandin E1 (PGE1) | 1 µg/ml |

Table 5 is another exemplary incubating agent.

In some embodiments, platelets (e.g., apheresis platelets, platelets isolated from whole blood, pooled platelets, or a combination thereof) are incubated with the incubating agent for different durations at or at different temperatures from 15-45° C., or about 37° C.

In some embodiments, platelets (e.g., apheresis platelets, platelets isolated from whole blood, pooled platelets, or a combination thereof) form a suspension in an incubating agent comprising a liquid medium at a concentration from 10,000 platelets/µL to 10,000,000 platelets/µL, such as 50,000 platelets/µL to 2,000,000 platelets/µL, such as 100,000 platelets/µL to 500,000 platelets/µL, such as 150,000 platelets/µL to 300,000 platelets/µL, such as 200,000 platelets/µL.

The platelets (e.g., apheresis platelets, platelets isolated from whole blood, pooled platelets, or a combination thereof) may be incubated with the incubating agent for different durations, such as, for example, for at least about 5 minutes (mins) (e.g., at least about 20 mins, about 30 mins, about 1 hour (hr), about 2 hrs, about 3 hrs, about 4 hrs, about 5 hrs, about 6 hrs, about 7 hrs, about 8 hrs, about 9 hrs, about 10 hrs, about 12 hrs, about 16 hrs, about 20 hrs, about 24 hrs, about 30 hrs, about 36 hrs, about 42 hrs, about 48 hrs, or at least about 48 hrs. In some embodiments, the platelets may be incubated with the incubating agent for no more than about 48 hrs (e.g., no more than about 20 mins, about 30 mins, about 1 hour (hr), about 2 hrs, about 3 hrs, about 4 hrs, about 5 hrs, about 6 hrs, about 7 hrs, about 8 hrs, about 9 hrs, about 10 hrs, about 12 hrs, about 16 hrs, about 20 hrs, about 24 hrs, about 30 hrs, about 36 hrs, or no more than about 42 hrs). In some embodiments, the platelets may be incubated with the incubating agent for from about 10 mins to about 48 hours (e.g., from about 20 mins to about 36 hrs, from about 30 mins to about 24 hrs, from about 1 hr to about 20 hrs, from about 2 hrs to about 16 hours, from about 10 mins to about 24 hours, from about 20 mins to about 12 hours, from about 30 mins to about 10 hrs, or from about 1 hr to about 6 hrs. In some embodiments, the platelets, the platelet derivatives, or the thrombosomes are incubated with the incubating agent for a period of time of 5 minutes to 48 hours, such as 10 minutes to 24 hours, such as 20 minutes to 12 hours, such as 30 minutes to 6 hours, such as 1 hour minutes to 3 hours, such as about 2 hours.

In some embodiments, the platelets (e.g., apheresis platelets, platelets isolated from whole blood, pooled platelets, or a combination thereof) are incubated with the incubating agents at different temperatures. In embodiments, incubation is conducted at 37° C. In certain embodiments, incubation is performed at 4° C. to 45° C., such as 15° C. to 42° C. For example, in embodiments, incubation is performed at 35° C. to 40° C. (e.g., 37° C.) for 110 to 130 (e.g., 120) minutes and for as long as 24-48 hours. In some embodiments, the platelets are incubated with the incubating agent for different durations as disclosed herein, and at temperatures from 15-45° C., or about 37° C.

In some embodiments, platelets (e.g., apheresis platelets, platelets isolated from whole blood, pooled platelets, or a combination thereof) are loaded with one or more active agents. In some embodiments, the platelets can be loaded with an anti-fibrinolytic agent. Non-limiting examples of anti-fibrinolytic agents include ε-aminocaproic acid (EACA), tranexamic acid, aprotinin, aminomethylbenzoic acid, and fibrinogen.

Loading platelets (e.g., apheresis platelets, platelets isolated from whole blood, pooled platelets, or a combination thereof) with an active agent (e.g., an anti-fibrinolytic agent) can be performed by any appropriate method. See, for example, PCT Publication Nos. WO2020113090A1, WO2020113101A1, WO2020113035A1, and WO2020112963A1. Generally, the loading includes contacting the platelets with the anti-fibrinolytic agent. In some embodiments, the loading can be performed by combining the active agent with the incubating agent. In some embodiments, the loading can be performed in a separate step from the incubating step. For example, the loading can be performed in a step prior to the incubation step. In some such embodiments, the active agent can be supplied to the platelets as a solution or suspension in any of the incubation agents described herein, which may or may not be the same as the incubating agent used in the incubating step. In some embodiments, the loading step can be performed during the incubation step. In some such embodiments, the active agent can be added to the incubation agent (e.g., as a solid or in a solution or suspension) during the incubation). In some embodiments, the loading step can be performed in a step following the incubation step. In some such embodiments, be supplied to the platelets as a solution or suspension in any of the incubation agents described herein, which may or may not be the same as the incubating agent used in the incubating step.

An active agent can be applied to the platelets in any appropriate concentration. In some embodiments, an active agent can be applied to the platelets (e.g., as part of the incubating agent or another solution or suspension) in a concentration of about 1 µM to about 100 mM (e.g., about 1 µM to about 10 µm, about 1 µM to about 50 µM, about 1 µM to about 100 µM, about 1 µM to about 500 µM, about 1 µM to about 1 mM, about 1 µM to about 10 mM, about 1 µM to about 25 mM, about 1 µM to about 50 mM, about 1 µM to about 75 mM, about 10 µM to about 100 mM, about 50 µM to about 100 mM, about 100 µM to about 100 mM, about 500 µM to about 100 mM, about 1 mM to about 100 mM, about 10 mM to about 100 mM, about 25 mM to about 100 mM, about 50 mM to about 100 mM, about 75 mM to about 100 mM, about 10 µM to about 100 mM, about 200 µM to about 1 mM, about 800 µM to about 900 µM, about 400 µM to about 800 µM, about 500 µM to about 700 µM, about 600 µM, about 5 mM to about 85 mM, about 20 mM to about 90 mM, about 25 mM to about 75 mM, about 30 mM to about 90 mM, about 35 mM to about 65 mM, about 40 mM to about 60 mM, about 50 mM to about 60 mM, about 40 mM to about 70 mM, about 45 mM to about 55 mM, or about 50 mM).

In some embodiments, the method further comprises drying the platelets. In some embodiments, the drying step comprises lyophilizing the platelets. In some embodiments, the drying step comprises freeze-drying the platelets. In some embodiments, the method further comprises rehydrating the platelets obtained from the drying step.

In some embodiments, the platelets are cold stored, cryopreserved, or lyophilized (e.g., to produce thrombosomes) prior to use in therapy or in functional assays.

Any known technique for drying platelets can be used in accordance with the present disclosure, as long as the technique can achieve a final residual moisture content of less than 5%. Preferably, the technique achieves a final residual moisture content of less than 2%, such as 1%, 0.5%, or 0.1%. Non-limiting examples of suitable techniques are freeze-drying (lyophilization) and spray-drying. A suitable lyophilization method is presented in Table A. Additional exemplary lyophilization methods can be found in U.S. Pat. Nos. 7,811,558, 8,486,617, and 8,097,403. An exemplary spray-drying method includes: combining nitrogen, as a drying gas, with a incubating agent according to the present disclosure, then introducing the mixture into GEA Mobile Minor spray dryer from GEA Processing Engineering, Inc. (Columbia Md., USA), which has a Two-Fluid Nozzle configuration, spray drying the mixture at an inlet temperature in the range of 150° C. to 190° C., an outlet temperature in the range of 65° C. to 100° C., an atomic rate in the range of 0.5 to 2.0 bars, an atomic rate in the range of 5 to 13 kg/hr, a nitrogen use in the range of 60 to 100 kg/hr, and a run time of 10 to 35 minutes. The final step in spray drying is preferentially collecting the dried mixture. The dried composition in some embodiments is stable for at least six months at temperatures that range from −20° C. or lower to 90° C. or higher.

TABLE A

Exemplary Lyophilization Protocol

| | Step | Temp. Set | Type | Duration | Pressure Set |
|---|---|---|---|---|---|
| Freezing Step | F1 | −50° C. | Ramp | Var | N/A |
| | F2 | −50° C. | Hold | 3 Hrs | N/A |
| Vacuum Pulldown | F3 | −50° | Hold | Var | N/A |
| Primary Dry | P1 | −40° | Hold | 1.5 Hrs | 0 mT |
| | P2 | −35° | Ramp | 2 Hrs | 0 mT |
| | P3 | −25° | Ramp | 2 Hrs | 0 mT |
| | P4 | −17° C. | Ramp | 2 Hrs | 0 mT |
| | P5 | 0° C. | Ramp | 1.5 Hrs | 0 mT |
| | P6 | 27° C. | Ramp | 1.5 Hrs | 0 mT |
| | P7 | 27° C. | Hold | 16 Hrs | 0 mT |
| Secondary Dry | S1 | 27° C. | Hold | >8 Hrs | 0 mT |

In some embodiments, the step of drying the platelets that are obtained as disclosed herein, such as the step of freeze-drying the platelets that are obtained as disclosed herein, comprises incubating the platelets with a lyophilizing agent (e.g., a non-reducing disaccharide). Accordingly, in some embodiments, the methods for preparing platelets further comprise incubating the platelets with a lyophilizing agent. In some embodiments the lyophilizing agent is a saccharide. In some embodiments the saccharide is a disaccharide, such as a non-reducing disaccharide.

In some embodiments, the platelets are incubated with a lyophilizing agent for a sufficient amount of time and at a suitable temperature to incubate the platelets with the lyophilizing agent. Non-limiting examples of suitable lyophilizing agents are saccharides, such as monosaccharides and disaccharides, including sucrose, maltose, trehalose, glucose (e.g., dextrose), mannose, and xylose. In some embodiments, non-limiting examples of lyophilizing agents include serum albumin, dextran, polyvinyl pyrrolidone (PVP), starch, and hydroxyethyl starch (HES). In some embodiments, exemplary lyophilizing agents can include a high molecular weight polymer. By "high molecular weight" it means a polymer having an average molecular weight of about or above 70 kDa and up to 1,000,000 kDa. Non-limiting examples are polymers of sucrose and epichlorohydrin (e.g., polysucrose). In some embodiments, the lyophilizing agent is polysucrose. Although any amount of high molecular weight polymer can be used as a lyophilizing agent, it is preferred that an amount be used that achieves a final concentration of about 3% to 10% (w/v), such as 3% to 7%, for example 6%.

An exemplary saccharide for use in the compositions disclosed herein is trehalose. Regardless of the identity of the saccharide, it can be present in the composition in any suitable amount. For example, it can be present in an amount of 1 mM to 1 M. In embodiments, it is present in an amount of from 10 mM 10 to 500 mM. In some embodiments, it is present in an amount of from 20 mM to 200 mM. In embodiments, it is present in an amount from 40 mM to 100 mM. In various embodiments, the saccharide is present in different specific concentrations within the ranges recited above, and one of skill in the art can immediately understand the various concentrations without the need to specifically recite each herein. Where more than one saccharide is present in the composition, each saccharide can be present in an amount according to the ranges and particular concentrations recited above.

Within the process provided herein for making the compositions provided herein, addition of the lyophilizing agent can be the last step prior to drying. However, in some embodiments, the lyophilizing agent is added at the same time or before other components of the composition, such as a salt, a buffer, optionally a cryoprotectant, or other components. In some embodiments, the lyophilizing agent is added to the incubating agent, thoroughly mixed to form a drying solution, dispensed into a drying vessel (e.g., a glass or plastic serum vial, a lyophilization bag), and subjected to conditions that allow for drying of the solution to form a dried composition.

The step of incubating the platelets with a cryoprotectant can include incubating the platelets for a time suitable for loading, as long as the time, taken in conjunction with the temperature, is sufficient for the cryoprotectant to come into contact with the platelets and, preferably, be incorporated, at least to some extent, into the platelets. In embodiments, incubation is carried out for about 1 minute to about 180 minutes or longer.

The step of incubating the platelets with a cryoprotectant can include incubating the platelets and the cryoprotectant at a temperature that, when selected in conjunction with the amount of time allotted, is suitable for incubating. In general, the composition is incubated at a temperature above freezing for at least a sufficient time for the cryoprotectant to come into contact with the platelets. In embodiments, incubation is conducted at 37° C. In certain embodiments, incubation is performed at 20° C. to 42° C. For example, in embodiments, incubation is performed at 35° C. to 40° C. (e.g., 37° C.) for 110 to 130 (e.g., 120) minutes.

In various embodiments, the lyophilization bag is a gas-permeable bag configured to allow gases to pass through at least a portion or all portions of the bag during the processing. The gas-permeable bag can allow for the exchange of gas within the interior of the bag with atmospheric gas present in the surrounding environment. The gas-permeable bag can be permeable to gases, such as oxygen, nitrogen, water, air, hydrogen, and carbon dioxide, allowing gas exchange to occur in the compositions provided herein. In some embodiments, the gas-permeable bag allows for the removal of some of the carbon dioxide present within an interior of the bag by allowing the carbon dioxide to permeate through its wall. In some embodiments, the release of carbon dioxide from the bag can be advantageous to maintaining a desired pH level of the composition contained within the bag.

In some embodiments, the container of the process herein is a gas-permeable container that is closed or sealed. In some embodiments, the container is a container that is closed or sealed and a portion of which is gas-permeable. In some embodiments, the surface area of a gas-permeable portion of a closed or sealed container (e.g., bag) relative to the volume of the product being contained in the container (hereinafter referred to as the "SA/V ratio") can be adjusted to improve pH maintenance of the compositions provided herein. For example, in some embodiments, the SA/V ratio of the container can be at least about 2.0 $cm^2/mL$ (e.g., at least about 2.1 $cm^2/mL$, at least about 2.2 $cm^2/mL$, at least about 2.3 $cm^2/mL$, at least about 2.4 $cm^2/mL$, at least about 2.5 $cm^2/mL$, at least about 2.6 $cm^2/mL$, at least about 2.7 $cm^2/mL$, at least about 2.8 $cm^2/mL$, at least about 2.9 $cm^2/mL$, at least about 3.0 $cm^2/mL$, at least about 3.1 $cm^2/mL$, at least about 3.2 $cm^2/mL$, at least about 3.3 $cm^2/mL$, at least about 3.4 $cm^2/mL$, at least about 3.5 $cm^2/mL$, at least about 3.6 $cm^2/mL$, at least about 3.7 $cm^2/mL$, at least about 3.8 $cm^2/mL$, at least about 3.9 $cm^2/mL$, at least about 4.0 $cm^2/mL$, at least about 4.1 $cm^2/mL$, at least about 4.2 $cm^2/mL$, at least about 4.3 $cm^2/mL$, at least about 4.4 $cm^2/mL$, at least about 4.5 $cm^2/mL$, at least about 4.6 $cm^2/mL$, at least about 4.7 $cm^2/mL$, at least about 4.8 $cm^2/mL$, at least about 4.9 $cm^2/mL$, or at least about 5.0 $cm^2/mL$. In some embodiments, the SA/V ratio of the container can be at most about 10.0 $cm^2/mL$ (e.g., at most about 9.9 $cm^2/mL$, at most about 9.8 $cm^2/mL$, at most about 9.7 $cm^2/mL$, at most about 9.6 $cm^2/mL$, at most about 9.5 $cm^2/mL$, at most about 9.4 $cm^2/mL$, at most about 9.3 $cm^2/mL$, at most about 9.2 $cm^2/mL$, at most about 9.1 $cm^2/mL$, at most about 9.0 $cm^2/mL$, at most about 8.9 $cm^2/mL$, at most about 8.8 $cm^2/mL$, at most about 8.7 $cm^2/mL$, at most about 8.6, $cm^2/mL$ at most about 8.5 $cm^2/mL$, at most about 8.4 $cm^2/mL$, at most about 8.3 $cm^2/mL$, at most about 8.2 $cm^2/mL$, at most about 8.1 $cm^2/mL$, at most about 8.0 $cm^2/mL$, at most about 7.9 $cm^2/mL$, at most about 7.8 $cm^2/mL$, at most about 7.7 $cm^2/mL$, at most about 7.6 $cm^2/mL$, at most about 7.5 $cm^2/mL$, at most about 7.4 $cm^2/mL$, at most about 7.3 $cm^2/mL$, at most about 7.2 $cm^2/mL$, at most about 7.1 $cm^2/mL$, at most about 6.9 $cm^2/mL$, at most about 6.8 $cm^2/mL$, at most about 6.7 $cm^2/mL$, at most about 6.6 $cm^2/mL$, at most about 6.5 $cm^2/mL$, at most about 6.4 $cm^2/mL$, at most about 6.3 $cm^2/mL$, at most about 6.2 $cm^2/mL$, at most about 6.1 $cm^2/mL$, at most about 6.0 $cm^2/mL$, at most about 5.9 $cm^2/mL$, at most about 5.8 $cm^2/mL$, at most about 5.7 $cm^2/mL$, at most about 5.6 $cm^2/mL$, at most about 5.5 $cm^2/mL$, at most about 5.4 $cm^2/mL$, at most about 5.3 $cm^2/mL$, at most about 5.2 $cm^2/mL$, at most about 5.1 $cm^2/mL$, at most about 5.0 $cm^2/mL$, at most about 4.9 $cm^2/mL$, at most about 4.8 $cm^2/mL$, at most about 4.7 $cm^2/mL$, at most about 4.6 $cm^2/mL$, at most about 4.5 $cm^2/mL$, at most about 4.4 $cm^2/mL$, at most about 4.3 $cm^2/mL$, at most about 4.2 $cm^2/mL$, at most about 4.1 $cm^2/mL$, or at most about 4.0 $cm^2/mL$. In some embodiments, the SA/V ratio of the container can range from about 2.0 to about 10.0 $cm^2/mL$ (e.g., from about 2.1 $cm^2/mL$ to about 9.9 $cm^2/mL$, from about 2.2 $cm^2/mL$ to about 9.8 cm²/mL, from about 2.3 cm²/mL to about 9.7 cm²/mL, from about 2.4 cm²/mL to about 9.6 cm²/mL, from about 2.5 cm²/mL to about 9.5 cm²/mL, from about 2.6 cm²/mL to about 9.4 cm²/mL, from about 2.7 cm²/mL to about 9.3 cm²/mL, from about 2.8 cm²/mL to about 9.2 cm²/mL, from about 2.9 cm²/mL to about 9.1 cm²/mL, from about 3.0 cm²/mL to about 9.0 cm²/mL, from about 3.1 cm²/mL to about 8.9 cm²/mL, from about 3.2 cm²/mL to about 8.8 cm²/mL, from about 3.3 cm²/mL to about 8.7 cm²/mL, from about 3.4 cm²/mL to about 8.6 cm²/mL, from about 3.5 cm²/mL to about 8.5 cm²/mL, from about 3.6 cm²/mL to about 8.4 cm²/mL, from about 3.7 cm²/mL to about 8.3 cm²/mL, from about 3.8 cm²/mL to about 8.2 cm²/mL, from about 3.9 cm²/mL to about 8.1 cm²/mL, from about 4.0 cm²/mL to about 8.0 cm²/mL, from about 4.1 cm²/mL to about 7.9 cm²/mL, from about 4.2 cm²/mL to about 7.8 cm²/mL, from about 4.3 cm²/mL to about 7.7 cm²/mL, from about 4.4 cm²/mL to about 7.6 cm²/mL, from about 4.5 cm²/mL to about 7.5 cm²/mL, from about 4.6 cm²/mL to about 7.4 cm²/mL, from about 4.7 cm²/mL to about 7.3 cm²/mL, from about 4.8 cm²/mL to about 7.2 cm²/mL, from about 4.9 cm²/mL to about 7.1 cm²/mL, from about 5.0 cm²/mL to about 6.9 cm²/mL, from about 5.1 cm²/mL to about 6.8 cm²/mL, from about 5.2 cm²/mL to about 6.7 cm²/mL, from about 5.3 cm²/mL to about 6.6 cm²/mL, from about 5.4 cm²/mL to about 6.5 cm²/mL, from about 5.5 cm²/mL to about 6.4 cm²/mL, from about 5.6 cm²/mL to about 6.3 cm²/mL, from about 5.7 cm²/mL to about 6.2 cm²/mL, or from about 5.8 cm²/mL to about 6.1 cm²/mL.

Gas-permeable closed containers (e.g., bags) or portions thereof can be made of one or more various gas-permeable materials. In some embodiments, the gas-permeable bag can be made of one or more polymers including fluoropolymers (such as polytetrafluoroethylene (PTFE) and perfluoro-alkoxy (PFA) polymers), polyolefins (such as low-density polyethylene (LDPE), high-density polyethylene (HDPE)), fluorinated ethylene propylene (FEP), polystyrene, polyvinylchloride (PVC), silicone, and any combinations thereof.

In some embodiments, dried platelets or platelet derivatives (e.g., thrombosomes) can undergo heat treatment. Heating can be performed at a temperature above about 25° C. (e.g., greater than about 40° C., 50° C., 60° C., 70° C., 80° C. or higher). In some embodiments, heating is conducted between about 70° C. and about 85° C. (e.g., between about 75° C. and about 85° C., or at about 75° C. or 80° C.). The temperature for heating can be selected in conjunction with the length of time that heating is to be performed. Although any suitable time can be used, typically, the lyophilized platelets are heated for at least 1 hour, but not more than 36 hours. Thus, in embodiments, heating is performed for at least 2 hours, at least 6 hours, at least 12 hours, at least 18 hours, at least 20 hours, at least 24 hours, or at least 30 hours. For example, the lyophilized platelets can be heated for 18 hours, 19 hours, 20 hours, 21 hours, 22 hours, 23 hours, 24 hours, 25 hours, 26 hours, 27 hours, 28 hours, 29 hours, or 30 hours. Non-limiting exemplary combinations include: heating the dried platelets or platelet derivatives (e.g., thrombosomes) for at least 30 minutes at a temperature higher than 30° C.; heating the dried platelets or platelet derivatives (e.g., thrombosomes) for at least 10 hours at a temperature higher than 50° C.; heating the dried platelets or platelet derivatives (e.g., thrombosomes) for at least 18 hours at a temperature higher than 75° C.; and heating the dried platelets or platelet derivatives (e.g., thrombosomes) for 24 hours at 80° C. In some embodiments, heating can be performed in sealed container, such as a capped vial. In some embodiments, a sealed container be subjected to a vacuum prior to heating. The heat treatment step, particularly in the presence of a cryoprotectant such as albumin or polysucrose, has been found to improve the stability and shelf-life of the freeze-dried platelets. Indeed, advantageous results have been obtained with the particular combination of serum albumin or polysucrose and a post-lyophilization heat treatment step, as compared to those cryoprotectants without a heat treatment step. A cryoprotectant (e.g., sucrose) can be present in any appropriate amount (e.g. about 3% to about 10% by mass or by volume of the platelets or platelet derivatives (e.g., thrombosomes).

In some embodiments, the platelets or platelet derivatives (e.g., thrombosomes) prepared as disclosed herein by a process comprising incubation with an incubating agent have a storage stability that is at least about equal to that of the platelets prior to the incubation.

In some embodiments, the method further comprises cryopreserving the platelets or platelet derivatives prior to administering the platelets or platelet derivatives (e.g., with an incubating agent, e.g., an incubating agent described herein).

In some embodiments, the method further comprises drying a composition comprising platelets or platelet derivatives, (e.g., with an incubating agent e.g., an incubating agent described herein) prior to administering the platelets or platelet derivatives (e.g., thrombosomes). In some embodiments, the method may further comprise heating the composition following the drying step. In some embodiments, the method may further comprise rehydrating the composition following the freeze-drying step or the heating step.

In some embodiments, the method further comprises freeze-drying a composition comprising platelets or platelet derivatives (e.g., with an incubating agent e.g., an incubating agent described herein) prior to administering the platelets or platelet derivatives (e.g., thrombosomes) In some embodiments, the method may further comprise heating the composition following the freeze-drying step. In some embodiments, the method may further comprise rehydrating the composition following the freeze-drying step or the heating step.

In some embodiments, the method further comprises cold storing the platelets, platelet derivatives, or the thrombosomes prior to administering the platelets, platelet derivatives, or thrombosomes (e.g., with an incubating agent, e.g., an incubating agent described herein).

Storing conditions include, for example, standard room temperature storing (e.g., storing at a temperature ranging from about 20 to about 30° C.) or cold storing (e.g., storing at a temperature ranging from about 1 to about 10° C.). In some embodiments, the method further comprises cryopreserving, freeze-drying, thawing, rehydrating, and combinations thereof, a composition comprising platelets or platelet derivatives (e.g., thrombosomes) (e.g., with an incubating agent e.g., an incubating agent described herein) prior to administering the platelets or platelet derivatives (e.g., thrombosomes). For example, in some embodiments, the method further comprises drying (e.g., freeze-drying) a composition comprising platelets or platelet derivatives (e.g., with an incubating agent e.g., an incubating agent described herein) (e.g., to form thrombosomes) prior to administering the platelets or platelet derivatives (e.g., thrombosomes). In some embodiments, the method may further comprise rehydrating the composition obtained from the drying step.

In some embodiments, provided herein is composition comprising platelets or platelet derivatives (e.g., thrombosomes), polysucrose and trehalose made by the process of obtaining fresh platelets, optionally incubating the platelets in DMSO, isolating the platelets by centrifugation, resuspending the platelets in an incubating agent which comprises trehalose and ethanol thereby forming a first mixture, incubating the first mixture, mixing polysucrose with the first mixture, thereby forming a second mixture, and lyophilizing the second mixture to form a freeze dried composition comprising platelets or platelet derivatives (e.g., thrombosomes), polysucrose and trehalose.

In some embodiments, provided herein is a method of making a freeze-dried platelet composition comprising platelets or platelet derivatives (e.g., thrombosomes), polysucrose and trehalose comprising obtaining fresh platelets, optionally incubating the platelets in DMSO, isolating the platelets by centrifugation, resuspending the platelets in a incubating agent which comprises trehalose and ethanol thereby forming a first mixture, incubating the first mixture, mixing polysucrose with the first mixture, thereby forming a second mixture, and lyophilizing the second mixture to form a freeze-dried composition comprising platelets or platelet derivatives (e.g., thrombosomes), polysucrose and trehalose.

In some embodiments, provided herein is a process for making freeze-dried platelets, the process comprising incubating isolated platelets in the presence of at least one saccharide under the following conditions: a temperature of from 20° C. to 42° C. for about 10 minutes to about 180 minutes, adding to the platelets at least one cryoprotectant, and lyophilizing the platelets, wherein the process optionally does not include isolating the platelets between the incubating and adding steps, and optionally wherein the process does not include exposing the platelets to a platelet activation inhibitor. The cryoprotectant can be a polysugar (e.g., polysucrose). The process can further include heating the lyophilized platelets at a temperature of 70° C. to 80° C. for 8 to 24 hours. The step of adding to the platelets at least one cryoprotectant can further include exposing the platelets to ethanol. The step of incubating isolated platelets in the presence of at least one saccharide can include incubating in the presence of at least one saccharide. The step of incubating isolated platelets in the presence of at least one saccharide can include incubating in the presence of at least one saccharide. The conditions for incubating can include incubating for about 100 minutes to about 150 minutes. The conditions for incubating can include incubating for about 110 minutes to about 130 minutes. The conditions for incubating can include incubating for about 120 minutes. The conditions for incubating can include incubating at 35° C. to 40° C. The conditions for incubating can include incubating at 37° C. The conditions for incubating can include incubating at 35° C. to 40° C. for 110 minutes to 130 minutes. The conditions for incubating can include incubating at 37° C. for 120 minutes. The at least one saccharide can be trehalose, sucrose, or both trehalose and sucrose. The at least one saccharide can be trehalose. The at least one saccharide can be sucrose.

In some embodiments, provided herein is a method of preparing freeze-dried platelets, the method including providing platelets, suspending the platelets in a salt buffer that includes about 100 mM trehalose and about 1% (v/v) ethanol to make a first composition, incubating the first composition at about 37° C. for about 2 hours, adding polysucrose (e.g., polysucrose 400) to a final concentration of about 6% (w/v) to make a second composition, lyophilizing the second composition to make freeze-dried platelets, and heating the freeze-dried platelets at 80° C. for 24 hours.

Specific embodiments disclosed herein may be further limited in the claims using "consisting of" or "consisting essentially of" language.

EXEMPLARY EMBODIMENTS

Embodiment 1 is a method of treating a coagulopathy in a subject, the method comprising administering to the subject in need thereof an effective amount of a composition comprising platelets or platelet derivatives and an incubating agent comprising one or more salts, a buffer, optionally a cryoprotectant, and optionally an organic solvent.

Embodiment 2 is a method of treating a coagulopathy in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 3 is a method of restoring normal hemostasis in a subject, the method comprising administering to the subject in need thereof an effective amount of a composition comprising platelets or platelet derivatives and an incubating agent comprising one or more salts, a buffer, optionally a cryoprotectant, and optionally an organic solvent.

Embodiment 4 is a method of restoring normal hemostasis in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 5 is a method of preparing a subject for surgery, the method comprising administering to the subject in need thereof an effective amount of a composition comprising platelets or platelet derivatives and an incubating agent comprising one or more salts, a buffer, optionally a cryoprotectant, and optionally an organic solvent.

Embodiment 6 is a method of preparing a subject for surgery, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 7 is the method of any one of embodiments 5-6, wherein the surgery is an emergency surgery.

Embodiment 8 is the method of any one of embodiments 5-6, wherein the surgery is a scheduled surgery.

Embodiment 9 is the method of any one of embodiments 1-8, wherein the subject has been treated or is being treated with an antiplatelet agent.

Embodiment 10 is the method of embodiment 9, wherein treatment with the antiplatelet agent is stopped.

Embodiment 11 is the method of embodiment 9, wherein treatment with the antiplatelet agent is continued.

Embodiment 12 is a method of ameliorating the effects of an antiplatelet agent in a subject, the method comprising administering to the subject in need thereof an effective amount of a composition comprising platelets or platelet derivatives and an incubating agent comprising one or more salts, a buffer, optionally a cryoprotectant, and optionally an organic solvent.

Embodiment 13 is a method of ameliorating the effects of an antiplatelet agent in a subject, the method comprising administering to the subject in need thereof an effective amount of a composition prepared by a process comprising incubating platelets with an incubating agent comprising one or more salts, a buffer, optionally a cryoprotectant, and optionally an organic solvent, to form the composition.

Embodiment 14 is the method of embodiment 12 or embodiment 13, wherein the effects of the antiplatelet agent are the result of an overdose of the antiplatelet agent.

Embodiment 15 is the method of any one of embodiments 1-14, wherein the composition further comprises an anti-fibrinolytic agent.

Embodiment 16 is the method of embodiment 15, wherein the anti-fibrinolytic agent is selected from the group consisting of ε-aminocaproic acid (EACA), tranexamic acid, aprotinin, aminomethylbenzoic acid, fibrinogen, and a combination thereof.

Embodiment 17 is the method of embodiment 15 or embodiment 16, wherein the platelets or platelet derivatives are loaded with the anti-fibrinolytic agent.

Embodiment 18 is the method of any one of embodiments 9-16, wherein the antiplatelet agent is selected from the group consisting of aspirin, cangrelor, ticagrelor, clopidogrel, prasugrel, eptifibatide, tirofiban, abciximab, a supplement, and a combination thereof.

Embodiment 19 is the method of any one of embodiments 9-16, wherein the antiplatelet agent is selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, and a combination thereof.

Embodiment 20 is the method of any one of embodiments 9-16, wherein the antiplatelet agent is selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, sarpogrelate, and a combination thereof.

Embodiment 21 is the method of any one of embodiments 1-20, wherein administering comprises administering topically.

Embodiment 22 is the method of any one of embodiments 1-20, wherein administering comprises administering parenterally.

Embodiment 23 is the method of any one of embodiments 1-20, wherein administering comprises administering intravenously.

Embodiment 24 is the method of any one of embodiments 1-20, wherein administering comprises administering intramuscularly.

Embodiment 25 is the method of any one of embodiments 1-20, wherein administering comprises administering intrathecally.

Embodiment 26 is the method of any one of embodiments 1-20, wherein administering comprises administering subcutaneously.

Embodiment 27 is the method of any one of embodiments 1-20, wherein administering comprises administering intraperitoneally.

Embodiment 28 is the method of any one of embodiments 1-27, wherein the composition is dried prior to the administration step.

Embodiment 29 is the method of embodiment 28, wherein the composition is rehydrated following the drying step.

Embodiment 30 is the method of any one of embodiments 1-28, wherein the composition is freeze-dried prior to the administration step.

Embodiment 31 is the method of embodiment 30, wherein the composition is rehydrated following the freeze-drying step.

Embodiment 32 is the method of any one of embodiments 1-31, wherein the incubating agent comprises one or more salts selected from phosphate salts, sodium salts, potassium salts, calcium salts, magnesium salts, and a combination of two or more thereof.

Embodiment 33 is the method of any one of embodiments 1-32, wherein the incubating agent comprises a carrier protein.

Embodiment 34 is the method of any one of embodiments 1-33, wherein the buffer comprises HEPES, sodium bicarbonate ($NaHCO_3$), or a combination thereof.

Embodiment 35 is the method of any one of embodiments 1-34, wherein the composition comprises one or more saccharides.

Embodiment 36 is the method of embodiment 35, wherein the one or more saccharides comprise trehalose.

Embodiment 37 is the method of embodiment 35 or embodiment 36, wherein the one or more saccharides comprise polysucrose.

Embodiment 38 is the method of any one of embodiments 35-37, wherein the one or more saccharides comprise dextrose.

Embodiment 39 is the method of any one of embodiments 1-38, wherein the composition comprises an organic solvent.

Embodiment 40 is the method of any of embodiments 1-39, wherein the platelets or platelet derivatives comprise thrombosomes.

EXAMPLES

The results that follow demonstrate the impact of the thrombosomes product in an in vitro model of a patient taking antiplatelet drugs. Thrombosomes and other lyophilized platelet products are designed for infusion into a patient's bloodstream following diagnosis of trauma or hemostatic failure. These drugs utilize multiple forms of platelet inhibition mechanisms which inhibit platelet response to adenosine diphosphate (ADP), arachidonic acid, fibrinogen and von Willebrand factor binding to name a few. These include drugs like aspirin, clopidogrel, ticagrelor, effient, cangrelor and eptifibatide.

Example 1

$P2Y_{12}$ Inhibitors

Cangrelor, like clopidogrel, ticagrelor, and prasugurel, blocks the $P2Y_{12}$ (ADP) receptor on platelets. Cangrelor is used here as a representative of this class of drug.

Thrombosomes were prepared consistent with the procedure in Example 4. Transmission light aggregometry and T-TAS® experiments were carried out according to Example 4.

The effect of cangrelor on the aggregation of platelets in platelet-rich plasma (PRP; taken from humans as whole blood and processed to isolate platelets in plasma without white blood cells (WBC) or red blood cells (rbc) was evaluated by transmission light aggregometry. Aggregation of platelets (platelet rich plasma) in response to agonist-induced activation showed complete inhibition of 10 μM adenosine diphosphate (ADP)-induced aggregation by cangrelor at therapeutic concentration of 0.5 μM-3.5 μM (FIG. 1). All doses of cangrelor investigated completely eliminated ADP-induced platelet aggregation in PRP.

Figure 2:
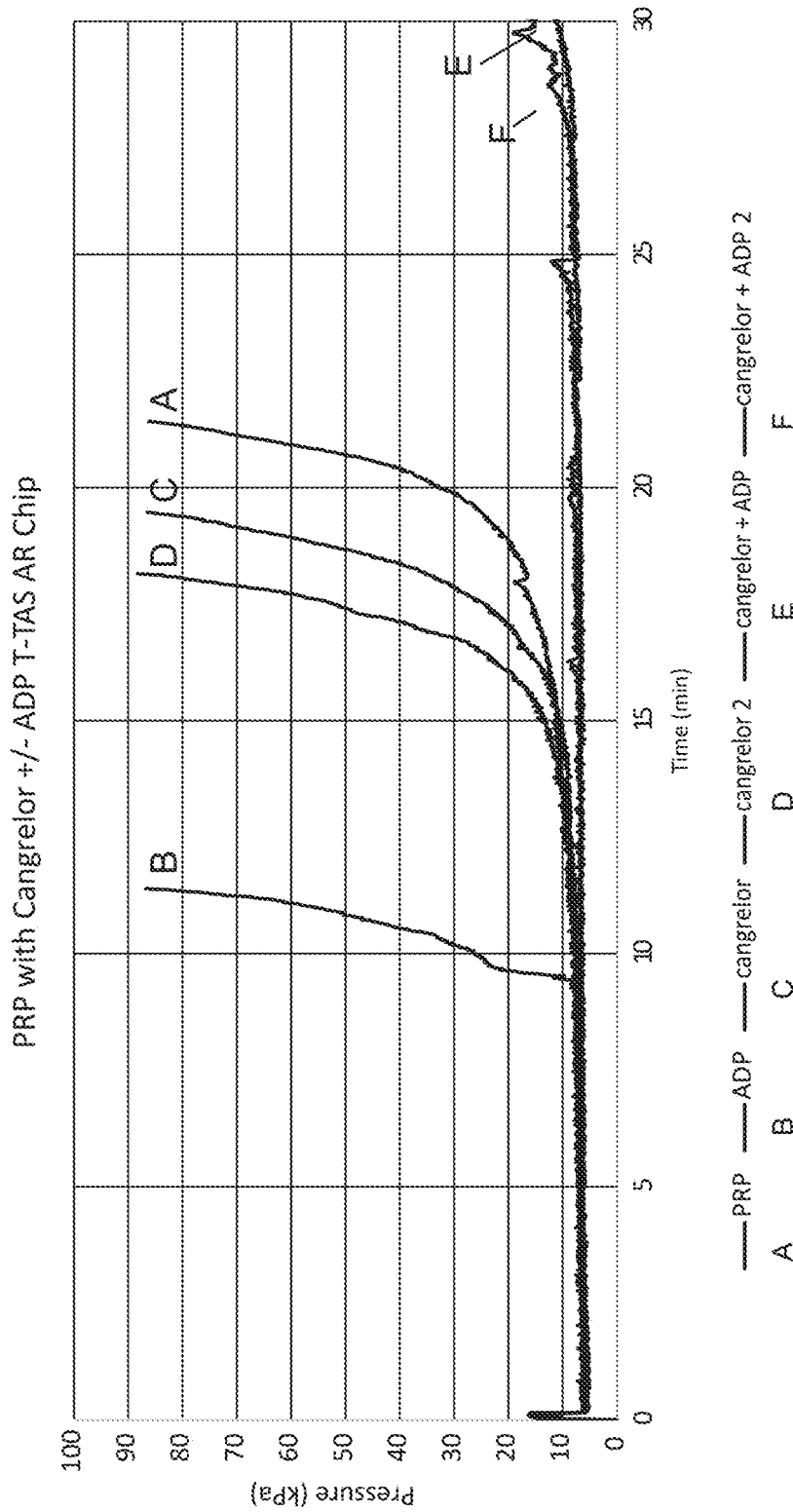
FIG. 2 shows the effect of cangrelor, ADP, or a combination thereof on platelet occlusion using T-TAS® technology.

The effect of cangrelor on platelet occlusion under shear was evaluated by T-TAS®. Fresh platelet rich plasma (platelet concentration 278,000/µL; PRP generally has a platelet concentration of about 200,000/µL, to about 300,000/µL) stimulated in vitro with 10 µM ADP occluded earlier under high shear than unstimulated platelets (PRP) as determined by AR chip (collagen and tissue thromboplastin) using T-TAS® technology (FIG. 2). Cangrelor alone (1 µM) did not exhibit inhibition on occlusion, but when combined with ADP (10 µM), platelet adhesion and occlusion was essentially eliminated. These results are further illustrated in FIGS. 3 and 4. Without being bound by any particular theory, it is believed that this pattern is observed because platelets have other ADP receptors not blocked by cangrelor that respond to ADP and cause shape change and aggregation where the ADP receptor $P2Y_{12}$ blocking inhibits collagen binding, and, accordingly, the platelets may bind each other due to ADP stimulation but may be prevented from binding collagen on the coated chip.

Figure 3:
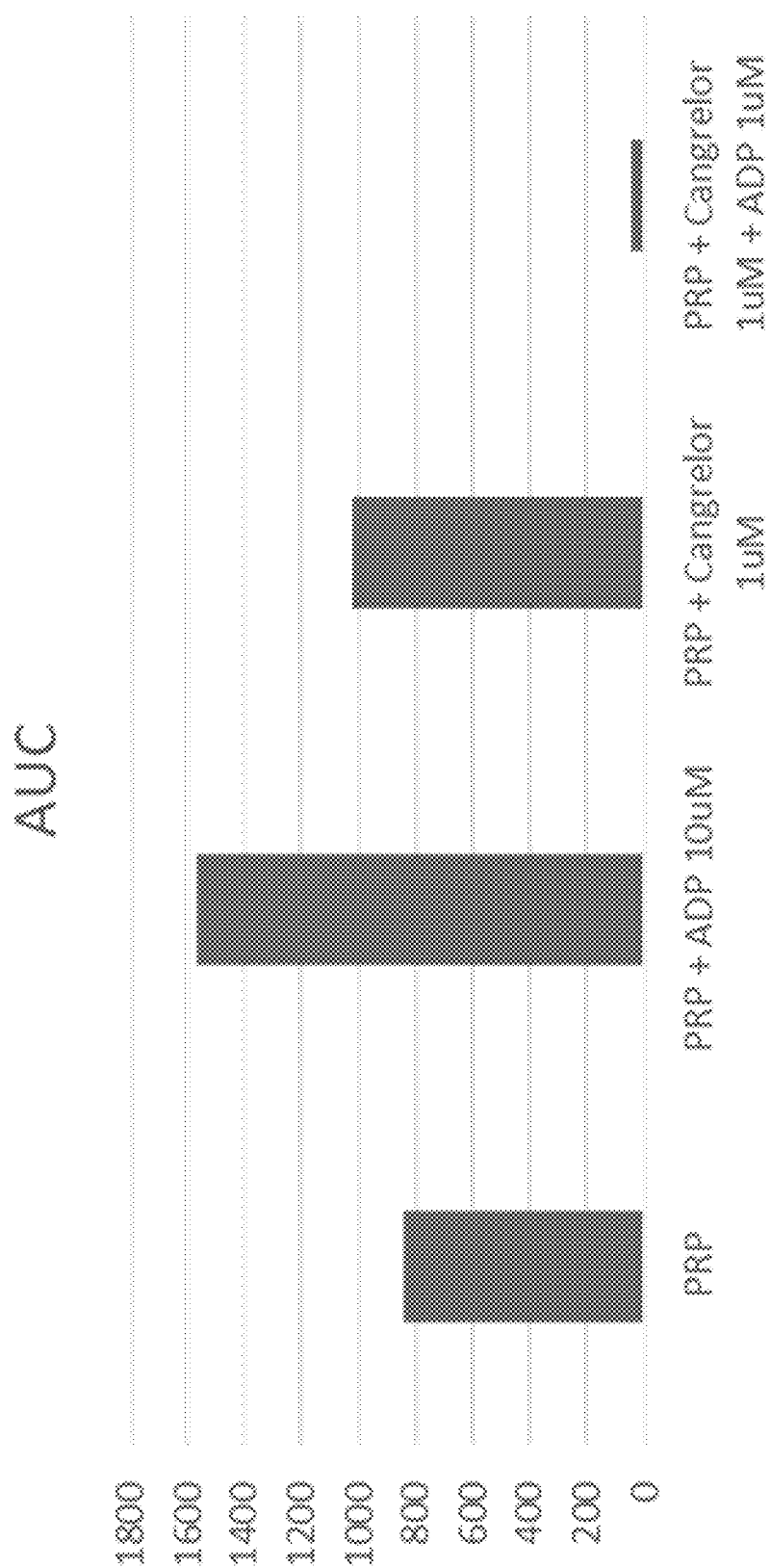
FIG. 3 is a bar plot of the area under the curve (AUC) for data sets from FIG. 2. Replicate data sets from FIG. 2 are presented as averages.

In FIG. 3, the area under the curve (AUC) values (derived from data in FIG. 2; replicates are averaged and plotted once) are indicative of a combined value of how quickly the thrombus happened in time and how substantial the thrombus is when it does happen. PRP AUC was increased with ADP stimulation. Cangrelor had little effect on AUC value, but when combined with ADP stimulation, the AUC dropped close to zero.

Figure 4:
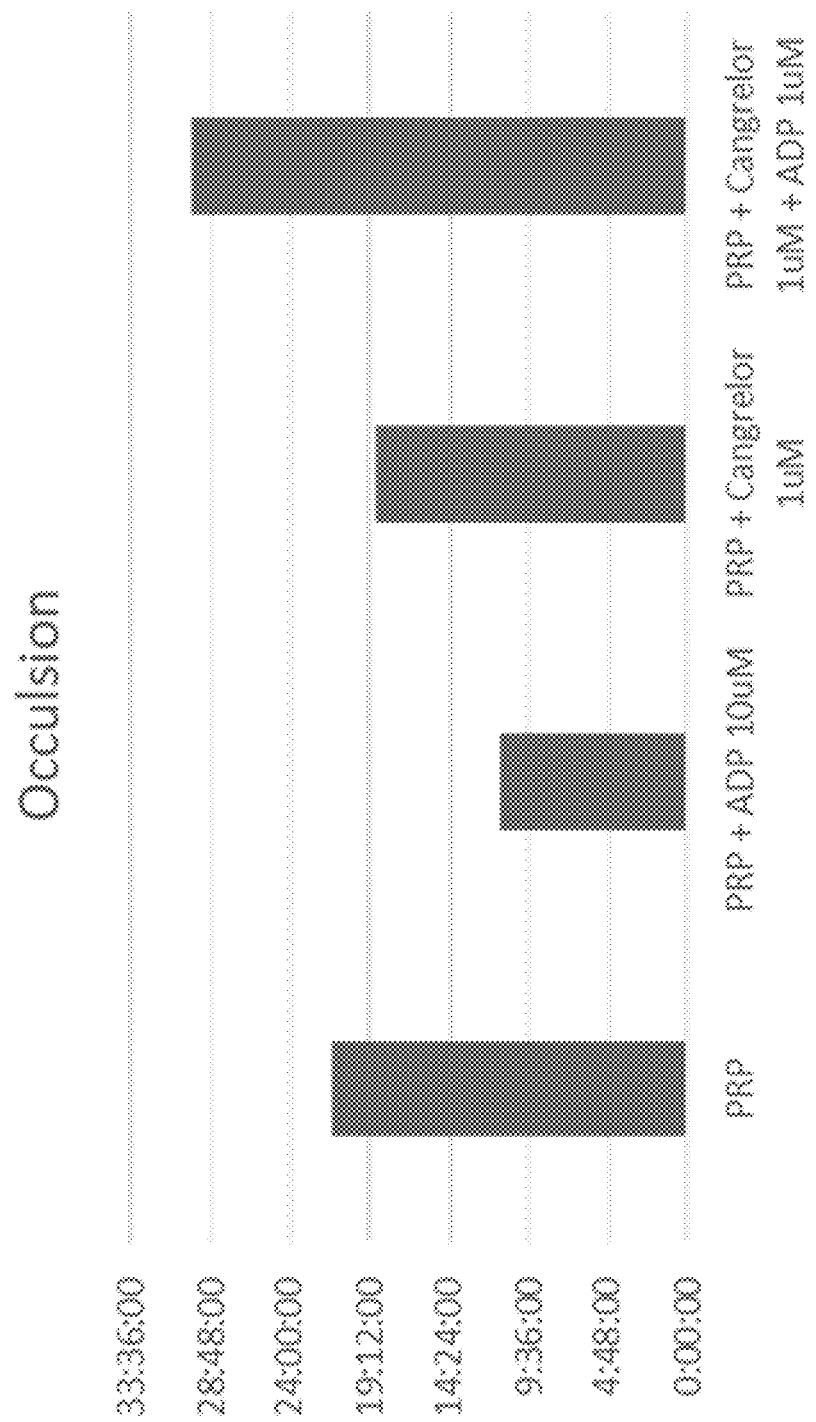
FIG. 4 is a bar plot of the occlusion time for data sets from FIG. 2. Replicate data sets from FIG. 2 are presented as averages.

In FIG. 4, the time to occlusion of the AR T-TAS® chip with drug treatment was evaluated. PRP occluded the chip channel at approximately 20 minutes, and stimulation of platelets with ADP decreased that time. Cangrelor had little effect on occlusion times, but addition of ADP stimulation to PRP sample inhibited occlusion essentially completely.

In the presence of cangrelor with ADP stimulation at the concentrations shown to be inhibitory of platelets, thrombosomes ("thromb" in FIGS. 5-7) were not inhibited, indicating that thrombosomes can aid in a clot formation even in the presence of cangrelor at therapeutic levels.

Figure 5:
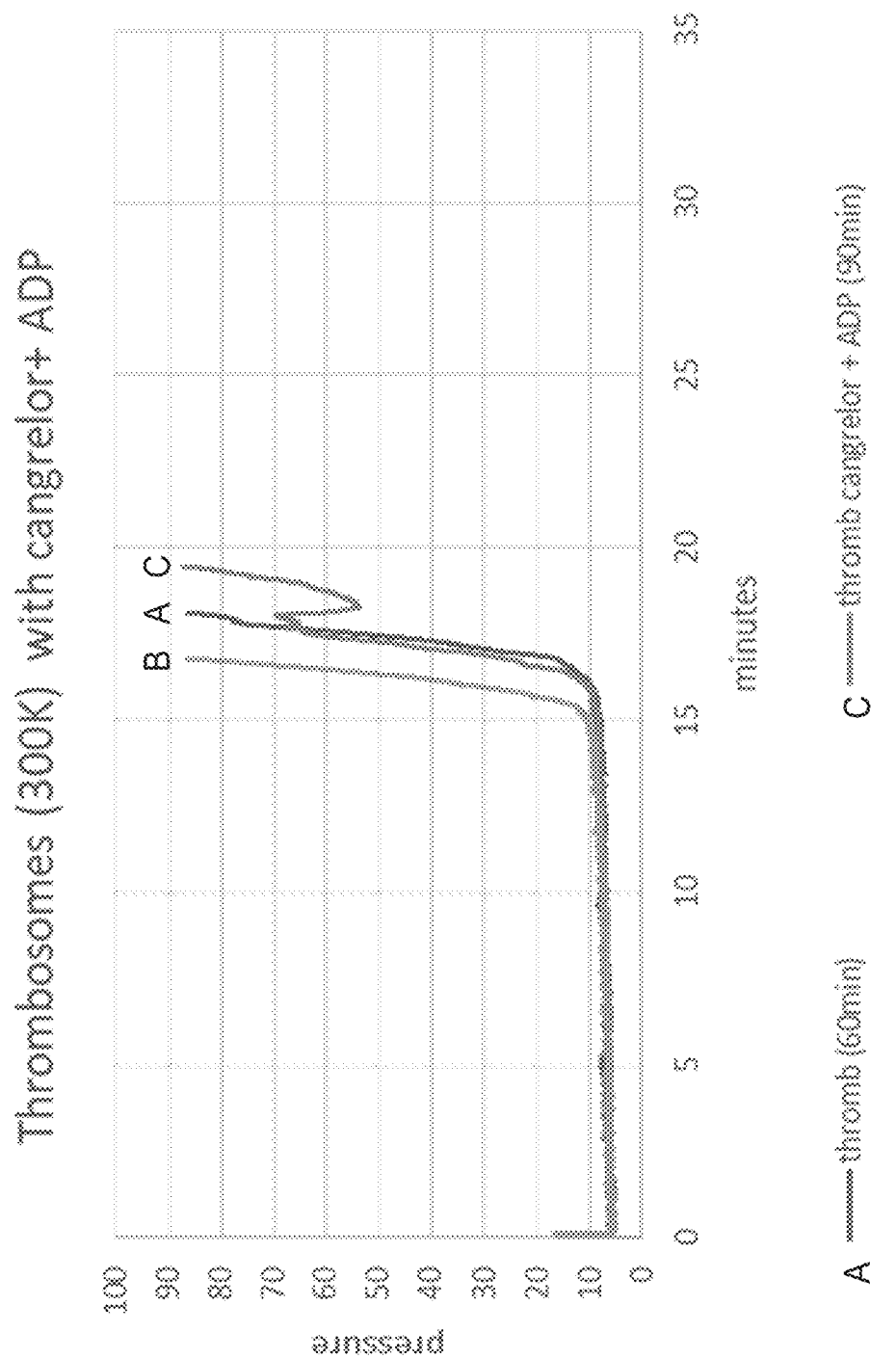
FIG. 5 shows the effect of thrombosomes ("thromb"; 300,000/μL) supplemented to platelet rich plasma in the presence and absence of ADP and cangrelor, at 60, 90, or 115 minutes post-rehydration on platelet occlusion using T-TAS® technology.

The effect of cangrelor on thrombosomes under shear was evaluated by T-TAS®. FIG. 5 shows that thrombosomes (after 60, 90, or 115 minutes of rehydration, as indicated) retain hemostatic function in the absence or presence of cangrelor (1 uM), with ADP (10 uM) present. Unlike platelets, thrombosomes occlusion of the T-TAS® AR Chip is unaffected by the antiplatelet effect of cangrelor+ADP. This suggests thrombosomes will maintain expected function when infused into patients receiving cangrelor and similar agents. These results are further illustrated in FIGS. 6 and 7.

Figure 6:
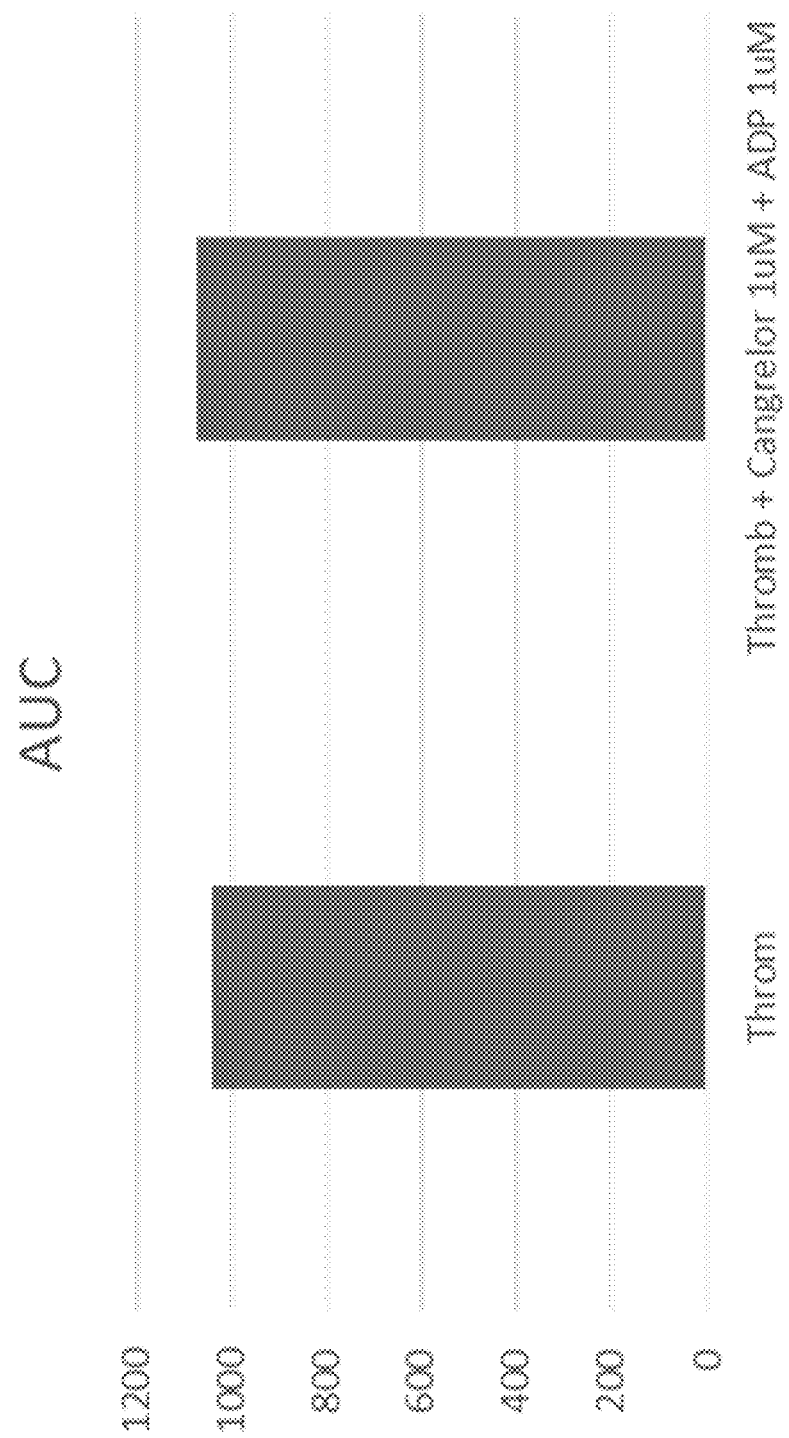
FIG. 6 is a bar plot of the AUC for data sets from FIG. 5. Replicate data sets from FIG. 5 are shown as averages.

In FIG. 6, the AUC values (derived from the data in FIG. 5) are indicative of thrombus formation. There was no effect of cangrelor+ADP on thrombosome adhesion and occlusion of the T-TAS® AR Chip in plasma; thrombosomes caused a thrombus formation regardless of cangrelor and ADP. The same dose of cangrelor and ADP completely inhibited freshly harvested platelets.

Figure 7:
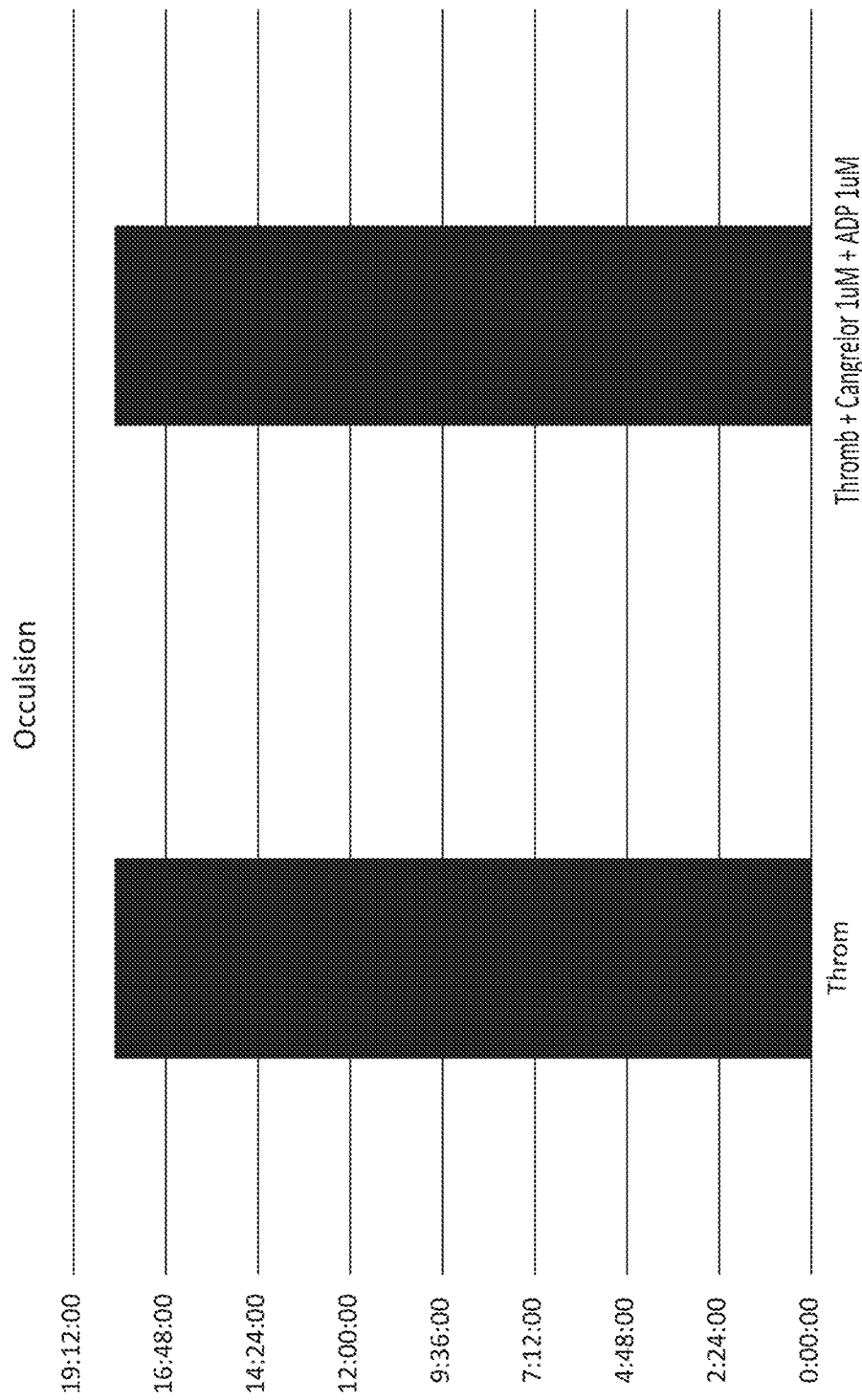
FIG. 7 is a bar plot of the occlusion time for data sets from FIG. 5. Replicate data sets from FIG. 5 are shown as averages.

In FIG. 7, the time to occlusion (derived from the data in FIG. 5) of the thrombosomes on AR T-TAS® chip with drug treatment was evaluated. There was no effect from cangrelor+ADP on thrombosome time to occlusion using the T-TAS® AR Chip in plasma. The same dose of cangrelor and ADP completely inhibited freshly harvested platelets.

Example 2

GPIIb-IIIa Inhibitors

The results that follow demonstrate the impact of thrombosomes in an in vitro model of a patient taking a GPIIb-IIIa inhibitor. Eptifibatide, a common antiplatelet drug, competitively inhibits the GPIIb-IIIa receptor on platelets which interact with fibrinogen and von Willebrand factor.

Eptifibatide is a peptide therapeutic that blocks the fibrin binding role of GPIIb-IIIa receptor on platelets. The drug is typically administered via IV as a 180 µg/kg bolus followed by 2 µg/kg/min continuous infusion. The blood concentration of eptifibatide is typically about 1-2 µM. Bleeding time generally returns to normal within about 1 hour of drug stoppage.

Thrombosomes were prepared consistent with the procedure in Example 4. Transmission light aggregometry and T-TAS® experiments were carried out according to Example 4.

Figure 8:
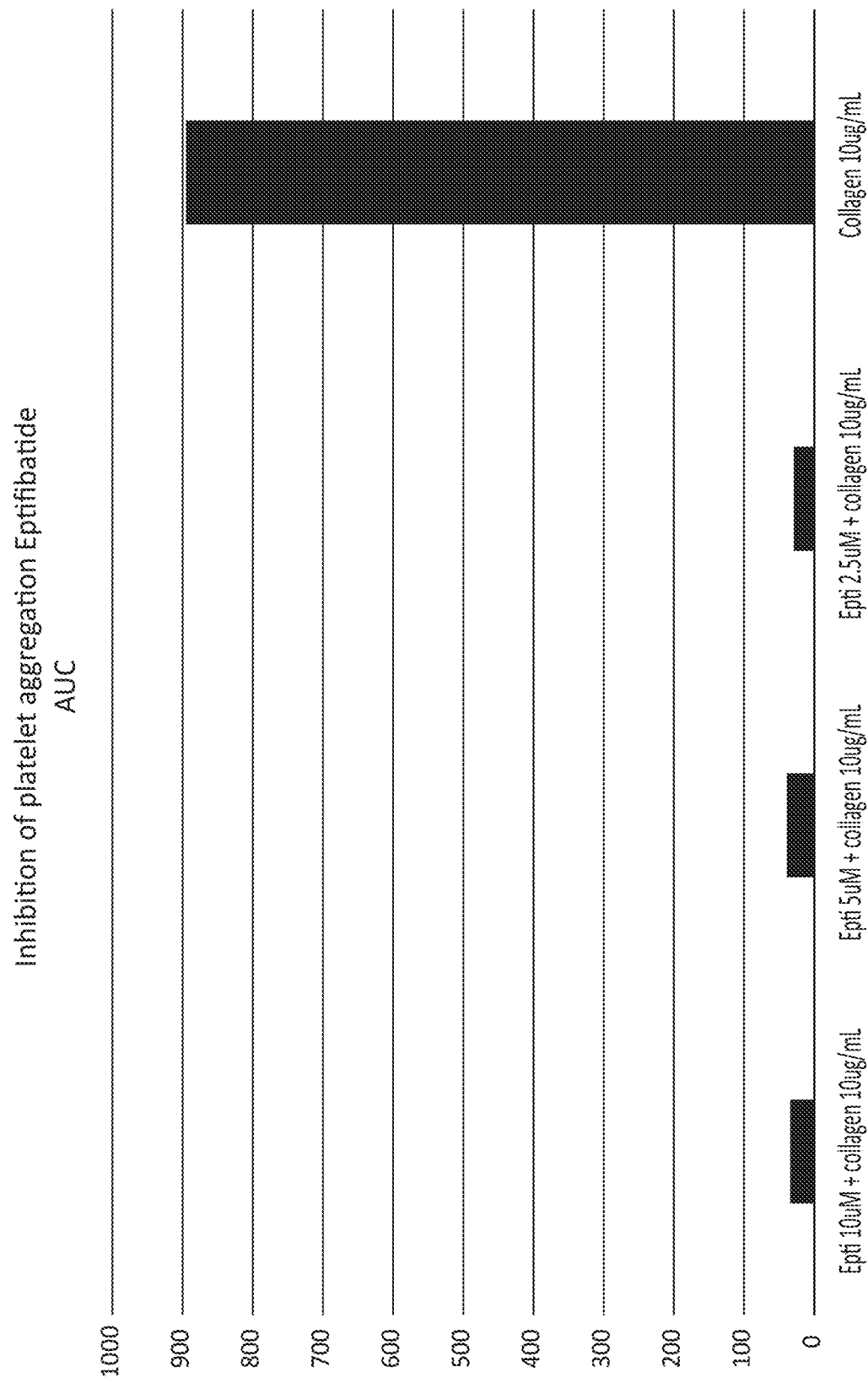
FIG. 8 is a bar plot of the AUC from aggregation experiments for platelets (at a concentration of 250,000 platelets per μL) treated with collagen (10 μg/mL) and various concentrations of eptifibatide ("Epti").

The aggregation of platelets (in platelet rich plasma) was evaluated using transmission light aggregrometry. Eptifibatide completely inhibited collagen-induced (10 µg/mL) platelet aggregation in PRP at all concentrations tested, as detected by light transmission aggregometry in PRP. (FIG. 8).

Figure 9:
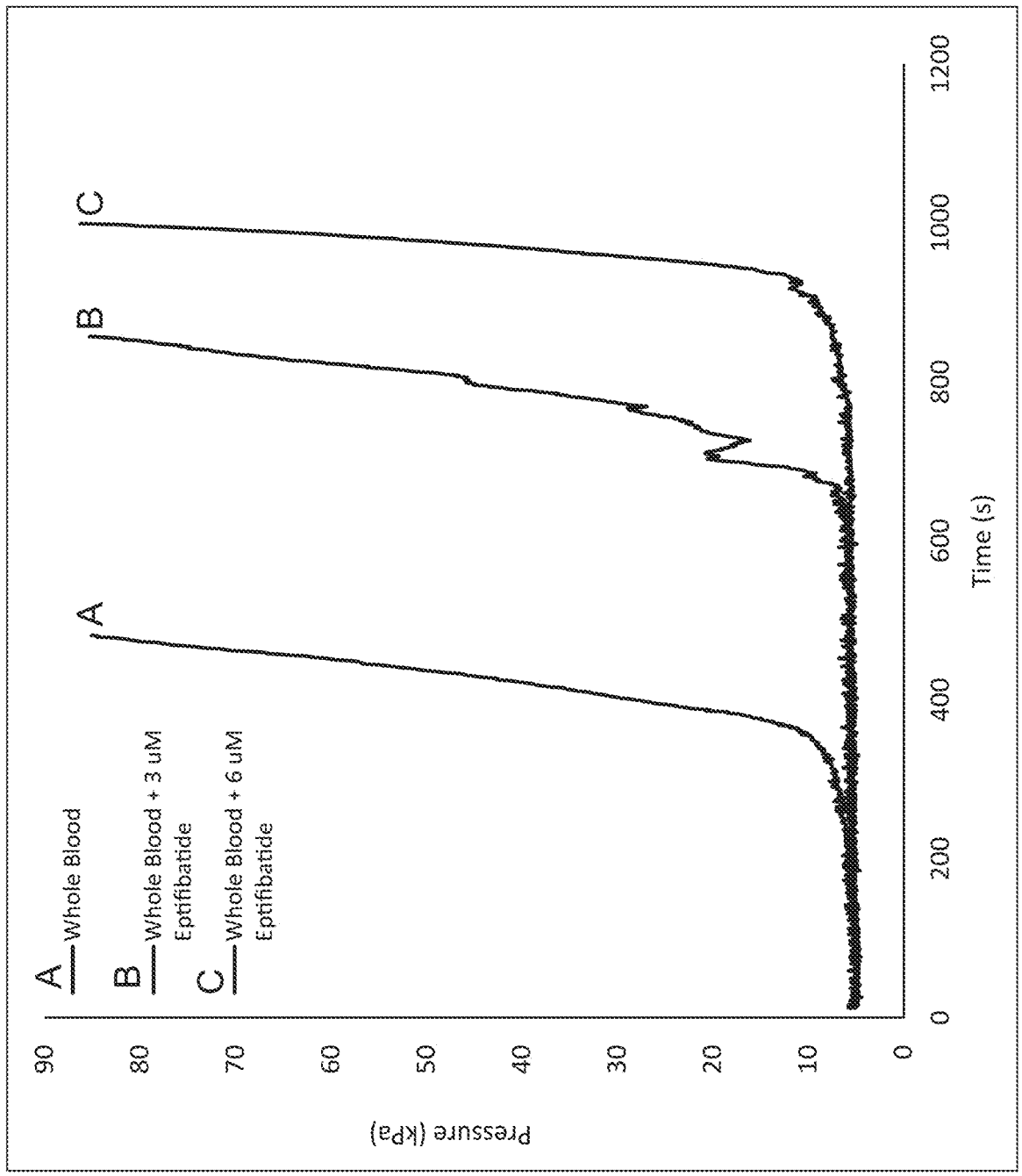
FIG. 9 shows the effect of eptifibatide at various concentrations on whole blood using T-TAS® technology.
Figure 10:
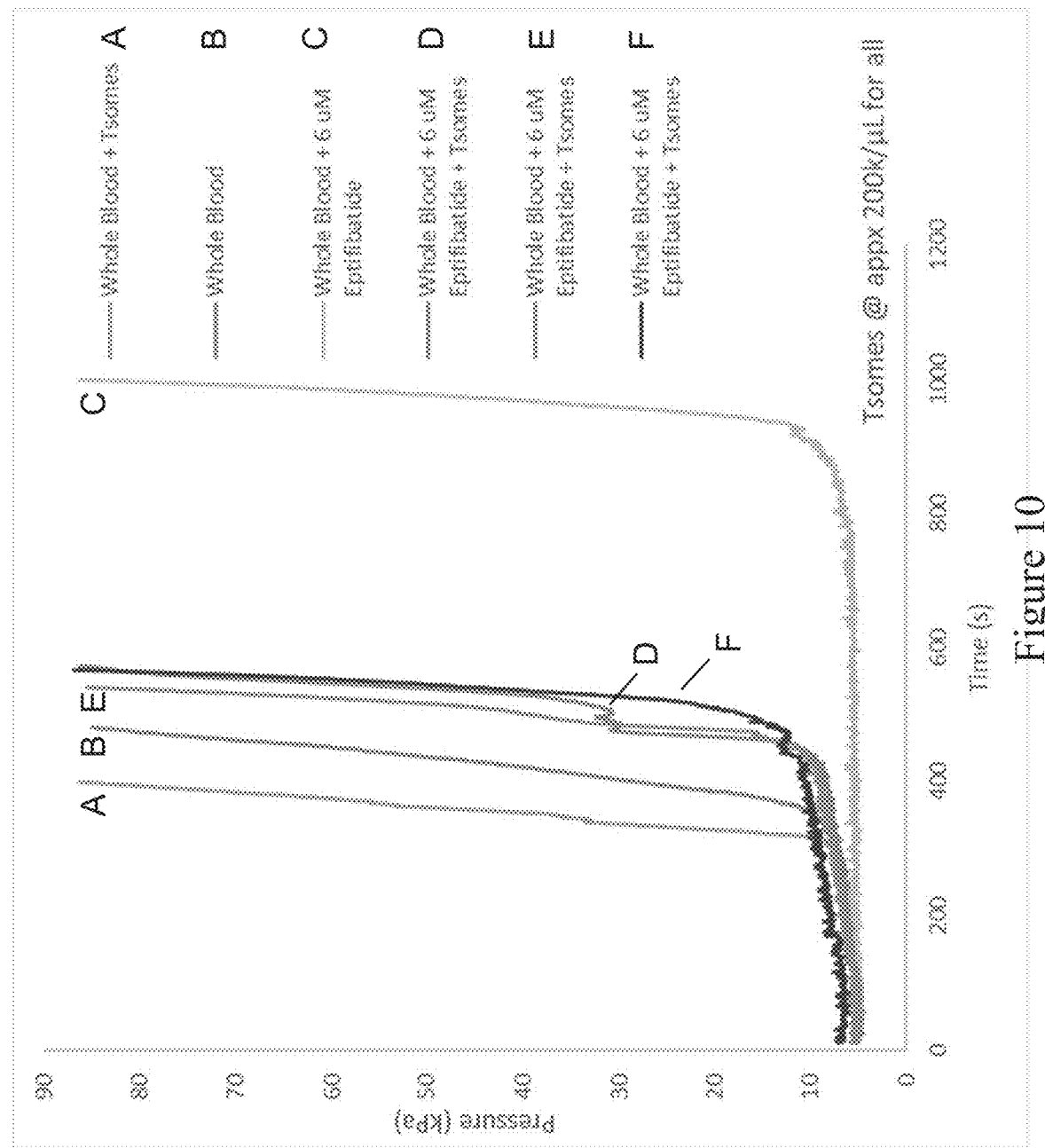
FIG. 10 shows the effect of thrombosome ("Tsomes") supplementation (approximately 200,000/μL) on whole blood with and without various concentrations of eptifibatide using T-TAS® technology.

The effect of thrombosomes on shortening clotting times while in the presence of eptifibatide was also studied. The ability of thrombosomes to recover occlusion times was studied on the T-TAS® system. The T-TAS® system measures occlusion time under shear forces with collagen and thromboplastin stimulation. The whole blood profile of occlusion and AUC on the AR T-TAS® chip lengthened and decreased, respectively, with eptifibatide. Eptifibatide extended the occlusion time of whole blood on the T-TAS® AR Chip in a dose-dependent manner. In this experiment, whole blood occluded at 8 minutes, and the occlusion time was extended to 16 minutes with 6 µM eptifibatide (FIG. 9). Thrombosomes reversed the inhibitory effect of eptifibatide on thrombus formation. Eptifibatide inhibition of whole blood occlusion on the T-TAS® AR Chip was reversed by the addition of thrombosomes at approximately 200,000/µL (N=3). When thrombosomes (approximately 200 k/µL) were added to the sample of whole blood inhibited with eptifibatide, the time to occlusion decreased to 'normal' at 9 minutes (FIG. 10).

Figure 11:
FIG. 11 is a bar plot of the occlusion time for the data sets from FIG. 10.
Figure 12:
FIG. 12 is a bar plot of the AUC for the data sets from FIG. 10.

The area under the curve values with thrombosome treatment also increased with thrombosomes compared to that of normal whole blood samples. FIG. 11 demonstrates the time to of occlusion of the thrombosomes on AR T-TAS® chip with drug treatment; eptifibatide inhibition of T-TAS® AR Chip occlusion was nearly entirely reversed by the addition of thrombosomes (200,000/µL; N=3). In FIG. 12, the area under the curve values were indicative of thrombus formation, where thrombosomes returned inhibition by eptifibatide to normal levels; eptifibatide inhibition of platelet adhesion to and occlusion of the T-TAS® AR Chip is overcome by addition of thrombosomes (200,000/µL; N=3).

Figure 13:
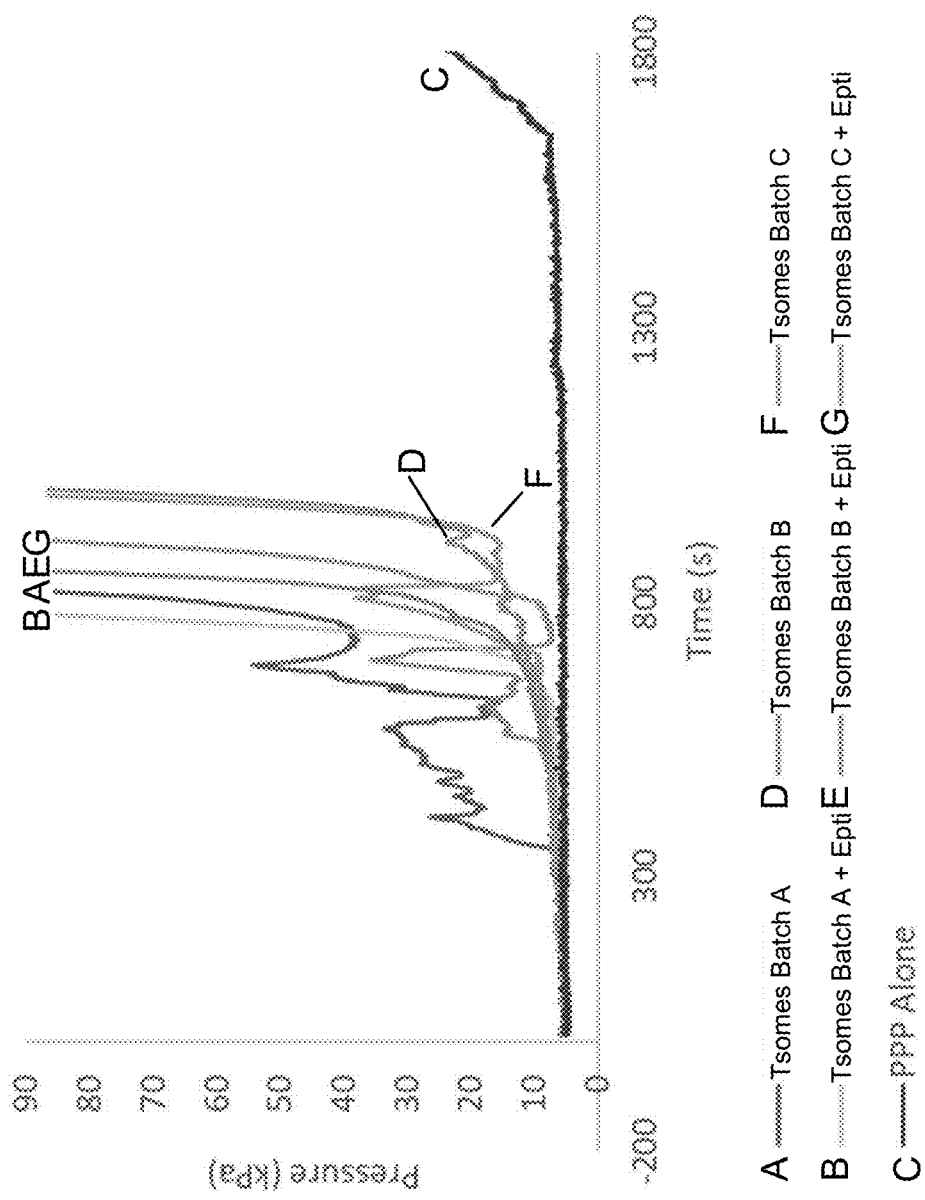
FIG. 13 shows that thrombosomes (various lots) occlude in the presence of eptifibatide in platelet-poor plasma (PPP).

Thrombosomes, unlike platelets, are not inhibited in their ability to occlude under shear in the presence of eptifibatide (FIG. 13). FIG. 13 shows profiles of thrombus formation of various lots of thrombosomes on AR T-TAS® system were unchanged with eptifibatide treatment. Thrombosomes in platelet poor plasma (PPP) were flowed through the T-TAS® AR Chip with and without 6 uM eptifibatide. There was no effect of eptifibatide on thrombosome adhesion and occlusion. All thrombosome concentrations were approximately 300,000/µL.

Figure 14:
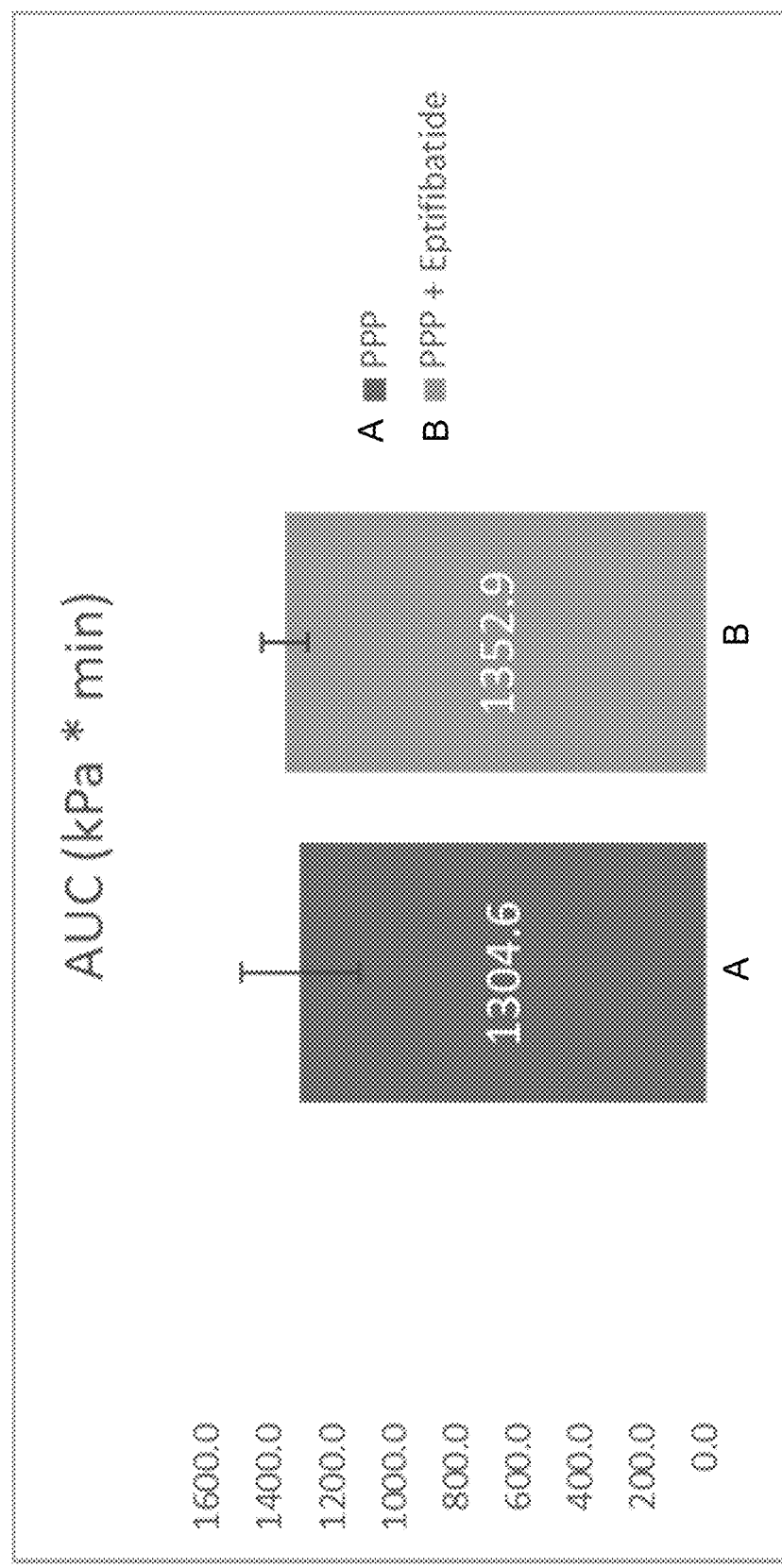
FIG. 14 is a bar plot of the AUC for data sets from FIG. 13. Replicate data sets from FIG. 13 are shown as averages.
Figure 15:
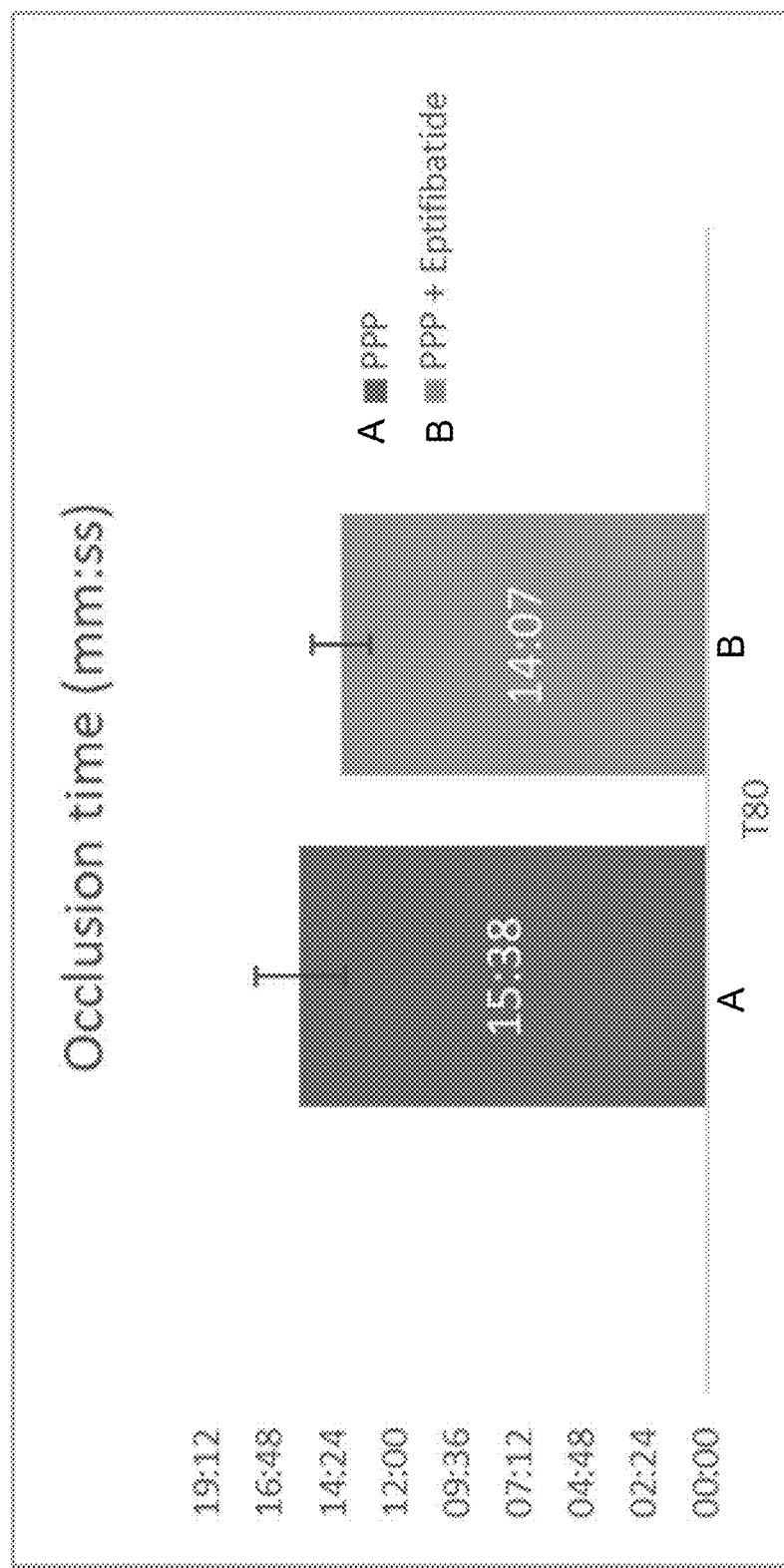
FIG. 15 is a bar plot of the occlusion time for the data sets from FIG. 13. Replicate data sets from FIG. 13 are shown as averages.

The AUC and occlusion values by T-TAS for thrombosomes (approximately 300,000/µL) in plasma was the same with and without eptifibatide (FIG. 14-15). FIG. 14 shows the area under the curve values were indicative of thrombus formation, and no changes were observed with eptifibatide in platelet-poor plasma. There was no effect of 6 uM eptifibatide on AUC of thrombosomes T-TAS® AR Chip occlusion. FIG. 15 shows the time to occlusion of the thrombosomes on AR T-TAS® chip was unchanged with eptifibatide. There was no significant influence from 6 µM eptifibatide on thrombosomes occlusion time of the T-TAS® AR Chip in platelet-poor plasma.

Example 3

COX Inhibitors

The results that follow demonstrate the impact of thrombosomes in an in vitro model of a patient taking a COX inhibitor. Aspirin, a common antiplatelet drug, blocks the COX1 enzyme in platelets. COX1 is responsible for converting arachidonic acid to prostaglandin.

Aspirin is an irreversible cyclooxygenase (COX) inhibitor. The COX enzyme in platelets is responsible for synthesis of thromboxane A2, prostaglandin E2, and prostacyclin (PGI2). Aspirin permanently inactivates the COX enzyme within platelets, and since platelets do not have the nuclear material to synthesize new enzyme, new platelets must be produced to overcome the aspirin effect. Without thromboxane A2, prostaglandin E2 and prostacyclin (PGI2) platelets are limited in their pro-aggregation activity. Many people are maintained on a low dose of aspirin to prevent unwanted clotting events. Aspirin bioavailability largely varies with administration route, with a single 500 mg dose IV at peaks of 500 µM and the same dose orally at 44 µM.

Thrombosomes were prepared consistent with the procedure in Example 4. Transmission light aggregometry and T-TAS® experiments were carried out according to Example 4.

Figure 16:
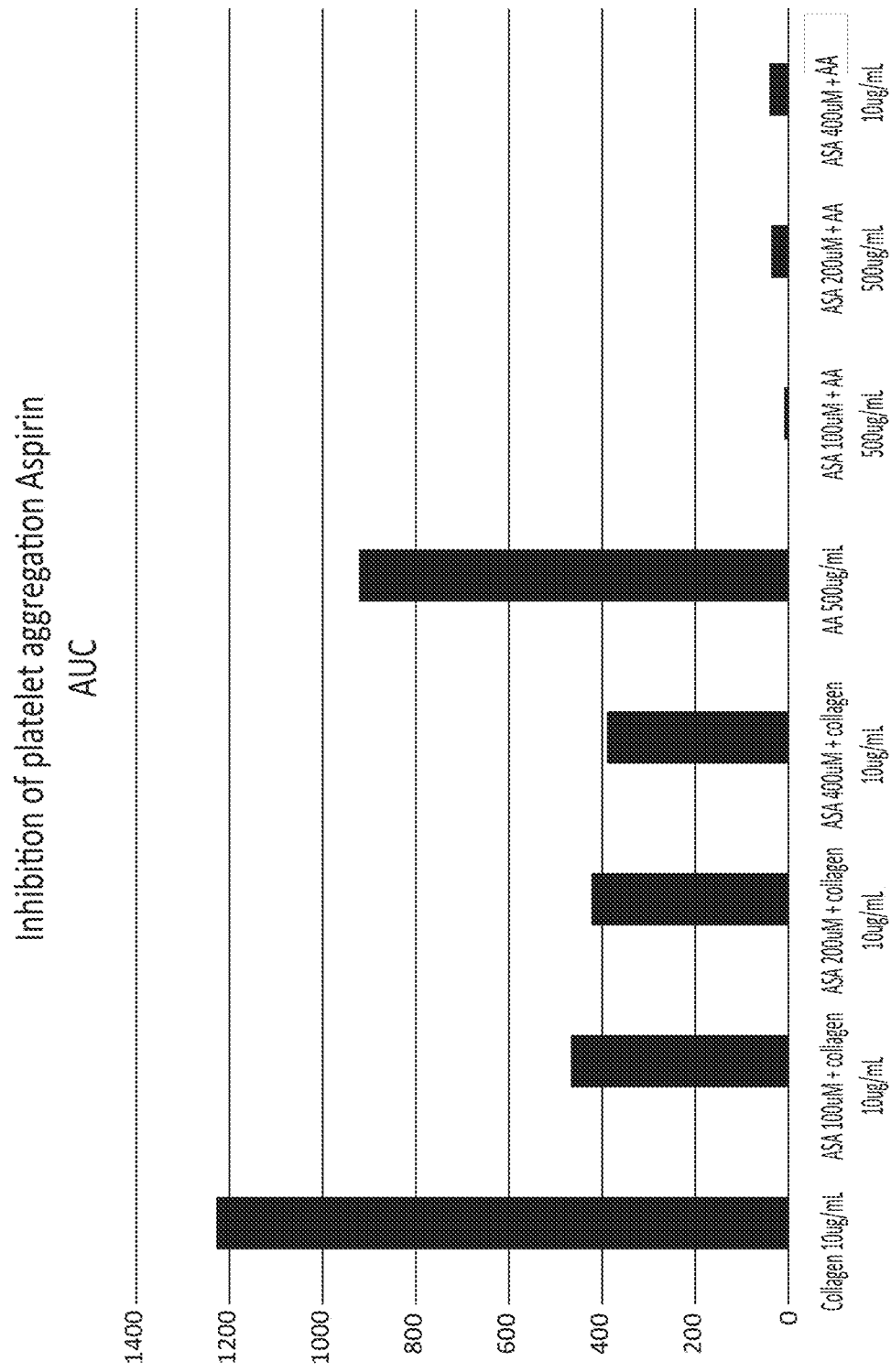
FIG. 16 is a bar plot of the AUC from aggregation experiments for platelets treated with collagen (10 μg/mL) or arachidonic acid ("AA"; 500 μg/mL) with and without various concentrations of aspirin ("ASA").
Figure 17:
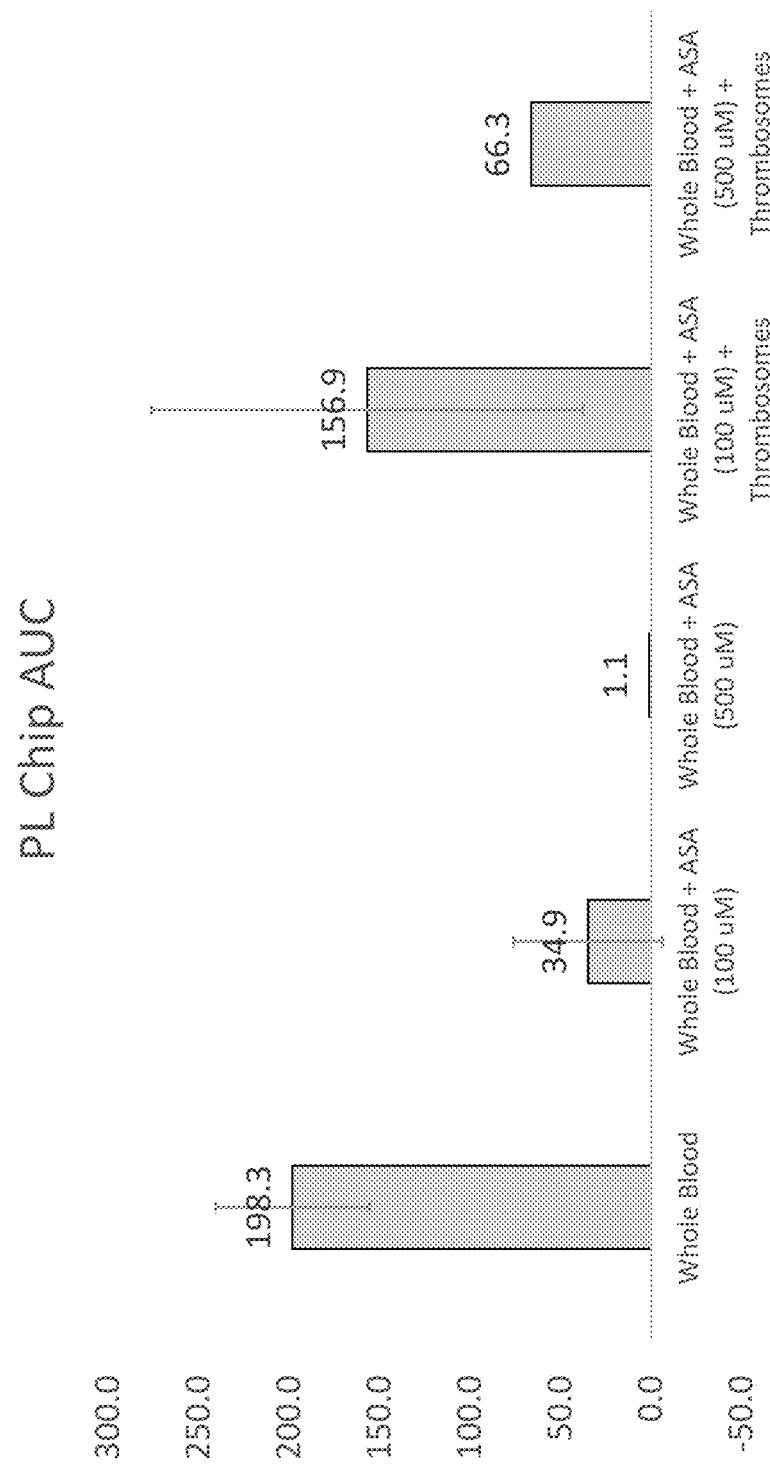
FIG. 17 is a bar plot of the occlusion time for whole blood, whole blood treated with various concentrations of aspirin (ASA), and whole blood treated with various concentrations of aspirin and supplemented with thrombosomes (approximately 200,000-400,000/μL) as measured by response to collagen coated plastic under shear using T-TAS® technology.

Platelets will aggregate with collagen and arachidonic acid stimulation. Stimulation by arachidonic acid can be completely inhibited whereas collagen stimulation aggregation can only be partially inhibited at concentrations of 100-400 µM aspirin (FIG. 16). FIG. 16 shows light transmission aggregometry in PRP with collagen (10 ug/mL) and arachidonic acid (AA; 500 ug/mL), which induced platelet aggregation, and that aggregation was inhibited by all doses of aspirin (ASA) tested. Aspirin eliminated arachidonic acid induced platelet aggregation entirely. The PL chip system on the T-TAS® was used to emulate in vitro platelet binding and aggregation due to the exposure of collagen in the vasculature under shear conditions. This action of platelets was largely limited in the presence of 100 and 500 µM of aspirin but can be at least partially returned in the presence of thrombosomes (approximately 200,000 to 400,000/µL; FIG. 17). FIG. 17 shows via area under the curve measurement of whole blood that thrombus formation on the PL T-TAS® chip was inhibited by aspirin with partial return of thrombus formation with thrombosomes.

Example 4

Protocols

Generation of thrombosomes. Thrombosomes were prepared consistent with the procedures described in U.S. Pat. No. 8,486,617 (such as, e.g., Examples 1-5) and U.S. Pat. No. 8,097,403 (such as, e.g., Examples 1-3), incorporated herein by reference in their entirety.

Transmission Light Aggregometry

Plasma samples with platelet or thrombosomes or combination of both are loaded into cuvettes and placed into the aggregometry chambers. The chambers warm the sample and provide constant stirring. The initiation of aggregation can be done by multiple types of inhibitor agents not limited to thrombin, ADP, collagen and any agent known to stimulate platelet aggregation. The samples can also have been taken as ex-vivo, or in-vitro supplemented with inhibitors. The instrument begins the assay by first recording the light transmission previous to stimulation for 2 minutes. The stimulant of interest is then introduced by the technician and the change in light transmission is recorded over time. The increase in light transmission corresponds to increase in platelet aggregation.

Evaluation by T-TAS® using an AR chip. AR chips are characterized by a single channel containing collagen and tissue factor; they can be used to analyze clotting and platelet function.

The T-TAS® instrument was prepared for use according to the manufacturer's instructions. AR Chips (Diapharma Cat. #TC0101) and AR Chip Calcium Corn Trypsin Inhibitor (CaCTI; Diapharma Cat. #TR0101) were warmed to room temperature. 300 uL of rehydrated thrombosomes were transferred to a 1.7 mL microcentrifuge tube and centrifuged at 3900 g×10 minutes to pellet. The thrombosomes pellet was resuspended in George King (GK) pooled normal human plasma or autologous plasma with or without autologous platelets to a concentration of approximately 100,000-450,000/uL, as determined by AcT counts (Beckman Coulter AcT Diff 2 Cell Counter). 20 uL of CaCTI with 480 uL of thrombosomes sample in GK plasma were mixed with gentle pipetting. The sample was loaded and run on the T-TAS® according to the manufacturer's instructions.

Evaluation by T-TAS® Using a PL Chip

PL chips are run similarly to AR chips, but this chip is only coated with collagen alone.

Thrombin Generation

Reagent Preparation. For thrombin generation, the following materials were used from manufacturers, as follows: FluCa Kit (Diagnostica Stago, Cat. No. 86197), Thrombin calibrator (Diagnostica Stago, Cat. No. 86197), PRP Reagent (Diagnostica Stago, Cat. No. 86196), OCTOPLAS®, a solvent detergent treated human pooled plasma (Octapharma, Cat. No. 8-68209-952-04). All frozen reagents were thawed in a 37° C. water bath before use. All reagents were rehydrated with sterile water using the volume printed on the reagent labels. Approximately 2 min after rehydration, the reagents were mixed by inverting vials 5 times, so no chunks or powder left; vortexing was not used. This procedure was repeated approximately 10 minutes after rehydration. All reagents were incubated at room temperature for another approximately 10 minutes (total of approximately 20 min after rehydration). A 30% solution of OCTOPLAS® was prepared by mixing 4.66 ml of thrombosomes control buffer (Table B) with 2 ml of OCTOPLAS®.

TABLE B

Thrombosomes Control Buffer

| Component | Concentration (mg/mL, except where otherwise indicated) |
|---|---|
| NaCl | 6.08 |
| KCl | 0.28 |
| HEPES | 2.47 |
| NaHCO$_3$ | 0.77 |

TABLE B-continued

Thrombosomes Control Buffer

| Component | Concentration (mg/mL, except where otherwise indicated) |
|---|---|
| Dextrose | 0.41 |
| Trehalose | 28.83 |
| Ethanol | 0.76% (v/v) |

Sample Analysis—Plate preparation and testing. For experiments containing thrombosomes, a thrombosomes dilution series was generated (dilutions of 194.4K, 64.8K, 21.6K, and 7.2K per µL were typically used; cell counts are determined by flow cytometry) for each the experimental thrombosomes and the reference thrombosomes. Thrombosomes were rehydrated unless indicated otherwise. The highest-concentration dilution (e.g., 194.4 k thrombosomes) was prepared by combining thrombosomes, OCTAPLAS®, and thrombosomes Control Buffer. The rest of the dilution series was prepared by serial 1:3 dilutions in OCTAPLAS®. For each test sample, 20 uL of PRP reagent was added to each sample well (of Immulon 2HB Clear, round-bottom 96-well plate (VWR, Cat. No. 62402-954)) and 20 uL of Thrombin Calibrator was added to each calibrator well. To each sample well and calibrator well, 80 uL of each of the thrombosomes dilution series was added. Continue until the last dilution. The plate was then incubated in the Fluoroskan Ascent 96 well fluorescent plate reader (Thrombinoscope) (ThermoFisher Scientific) for 10 minutes. During this incubation phase, the FluCa solution was prepared by adding 40 µL of FluCa substrate to the 1.6 ml of thawed Fluo-Buffer, vortexing, and returning the solution to the water bath. When incubation was complete, the FluCa solution was added to the Fluroskan instrument according to the manufacturer's instructions. The plate fluorescence was monitored for 75 minutes at an interval of 20 seconds and a temperature of 40-41° C.

Example 5

Additional experiments were carried out with cangrelor and aspirin. Thrombosomes were prepared consistent with the procedure in Example 4. Transmission light aggregometry, T-TAS®, and thrombin generation experiments were carried out according to Example 4.

Figure 18:
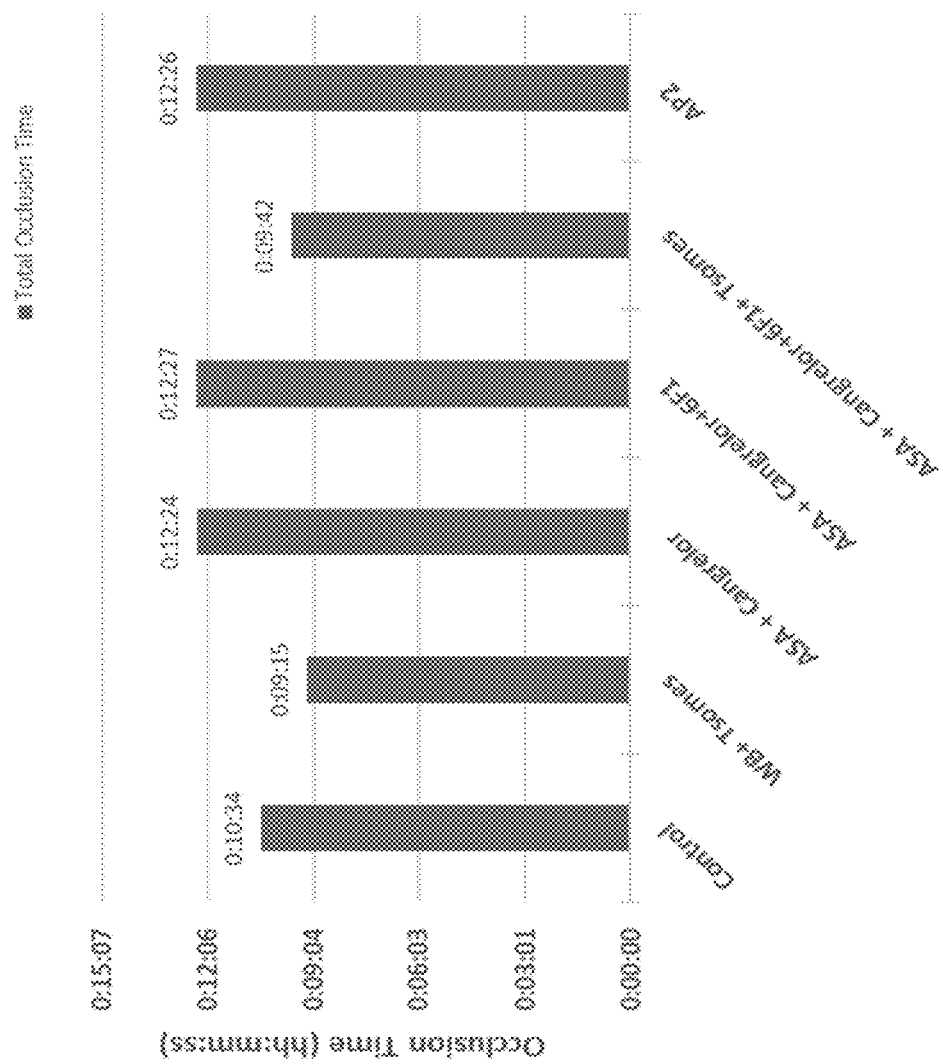
FIG. 18 shows the recovery of thrombus formation promoted by thrombosomes in whole blood in the presence of ASA (200 micromolar), cangrelor (1 micromolar), AP2 6F1 (40 micrograms), as measured by occlusion time on the T-TAS AR chip coated with thromboplastin and collagen.
Figure 19:
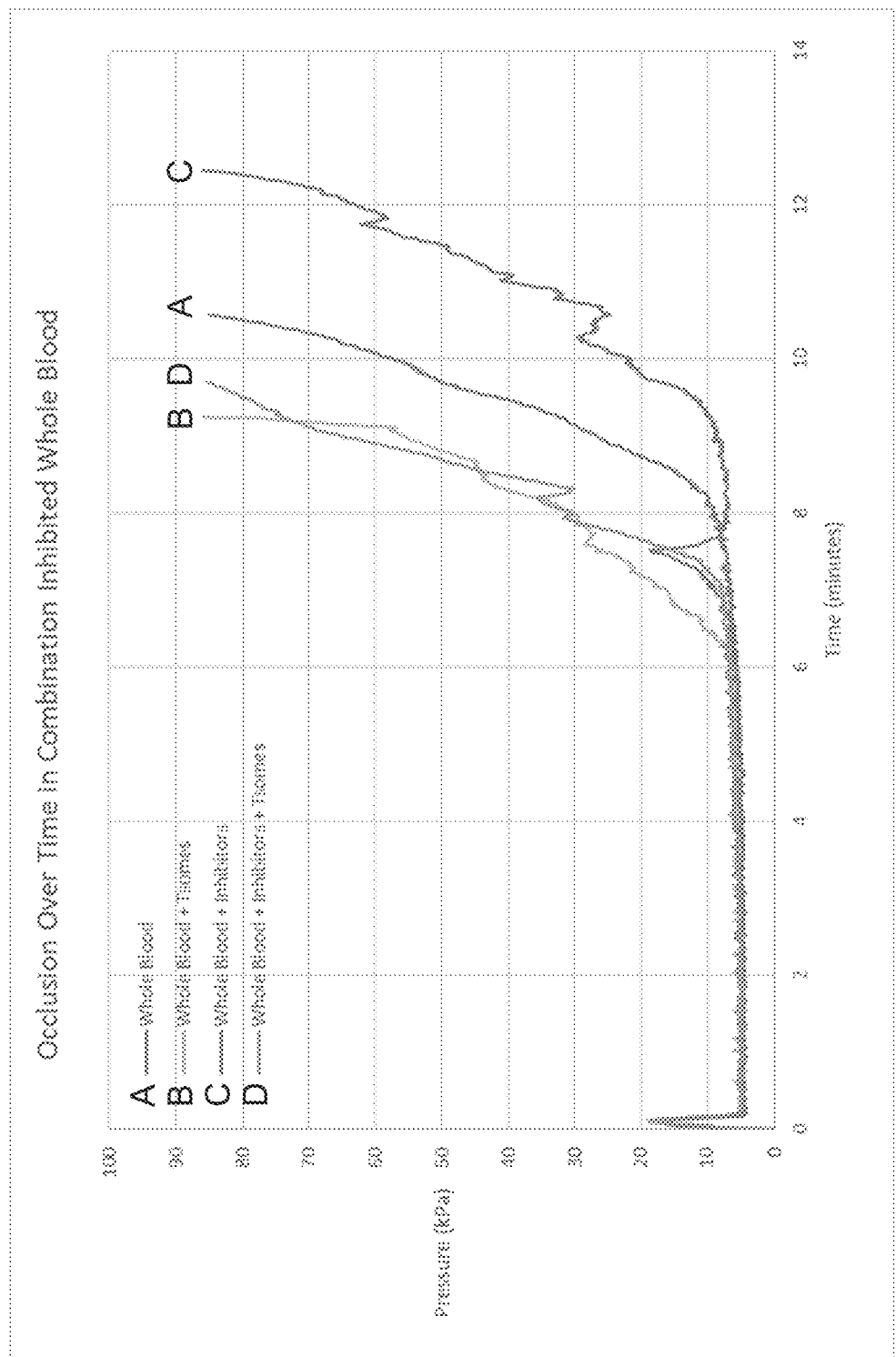
FIG. 19 shows the recovery of thrombus formation promoted by thrombosomes in whole blood in the presence of ASA (200 micromolar), cangrelor (1 micromolar) and 6F1 (40 micrograms/mL), as measured by occlusion (pressure) over time.

The effect of thrombosomes on the recovery of thrombus formation was evaluated using T-TAS® technology and an AR chip. FIG. 18 shows the occlusion time of whole blood treated with various combinations of thrombosomes (at a concentration of 250,000 thrombosomes per µL), aspirin (200 µM), cangrelor (1 µM), anti-Integrin alpha-2 (CD49B) antibody 6F1 (40 µg; see dshb.biology.uiowa.edu/integrin-alpha-2-alpha2beta1?sc=7&category=-107 for product/manufacturer information), and anti-GPIIb/IIIa receptor antibody AP2 (20 ug/mL; see kerafast.com/product/2010/anti-glycoprotein-gpiiiagpiib-complex-ap-2-antibody for product/manufacturer information). FIG. 19 shows the occlusion over time of untreated whole blood and whole blood treated with thrombosomes (at a concentration of 250,000 thrombosomes per a mixture containing 6F1 (40 ug/mL; anti-CD49b), ASA (aspirin; 200 uM), and cangrelor (1 uM); or a combination thereof.

Figure 20:
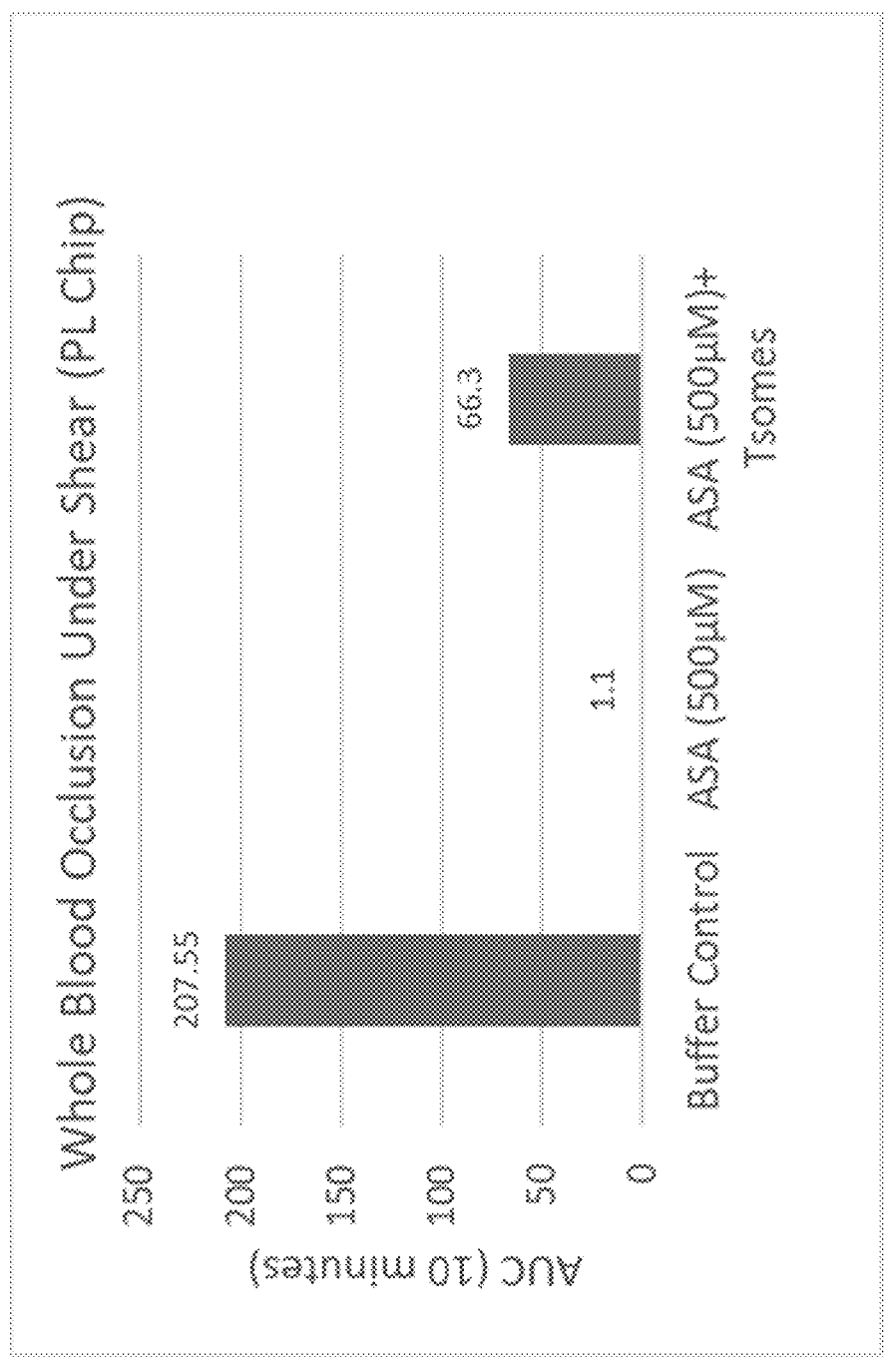
FIG. 20 shows the effect of thrombosomes supplementation to aspirin-(ASA-)inhibited whole blood (500 micromolar) on the interaction with plastic immobilized porcine collagen under high shear, as measured by AUC.
Figure 21:
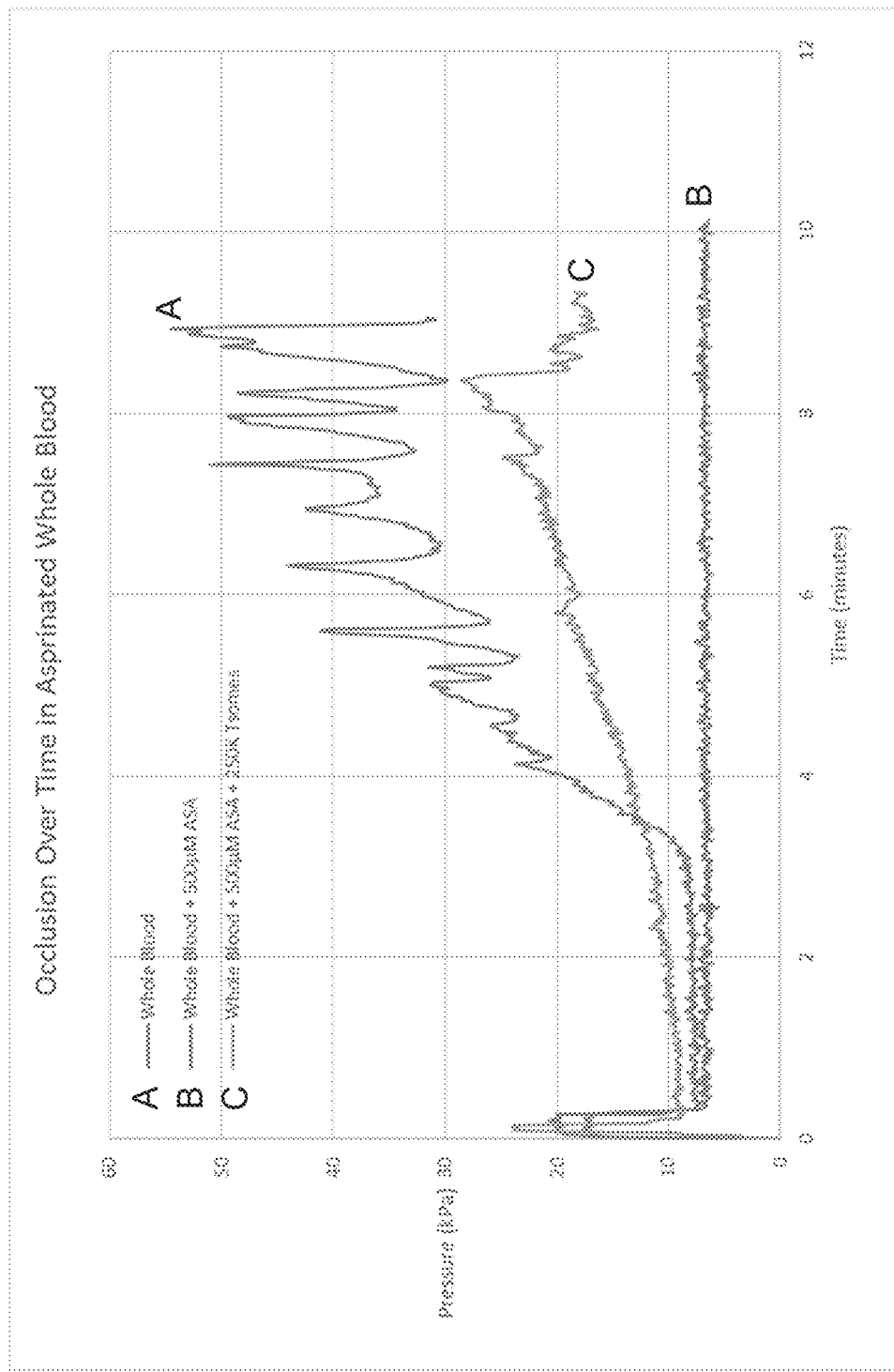
FIG. 21 shows the effect of thrombosomes supplementation to aspirin-(ASA-)inhibited whole blood (500 micromolar) on the interaction with plastic immobilized porcine collage under high shear, as measured by occlusion (pressure) over time.
Figure 22:
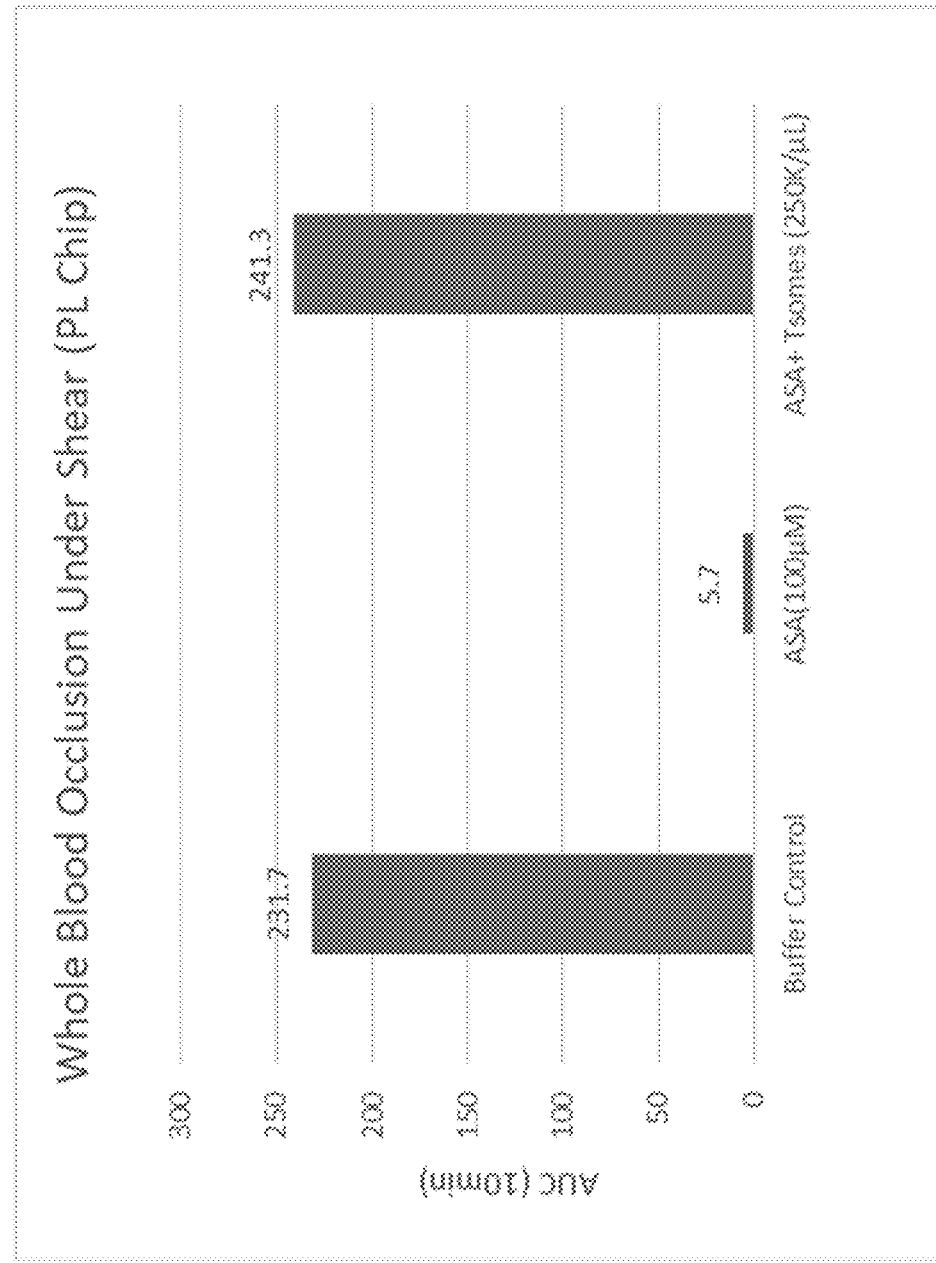
FIG. 22 shows the effect of thrombosomes supplementation to aspirin-(ASA-)inhibited whole blood (100 micromolar) on the interaction with plastic immobilized porcine collage under high shear, as measured by AUC.
Figure 23:
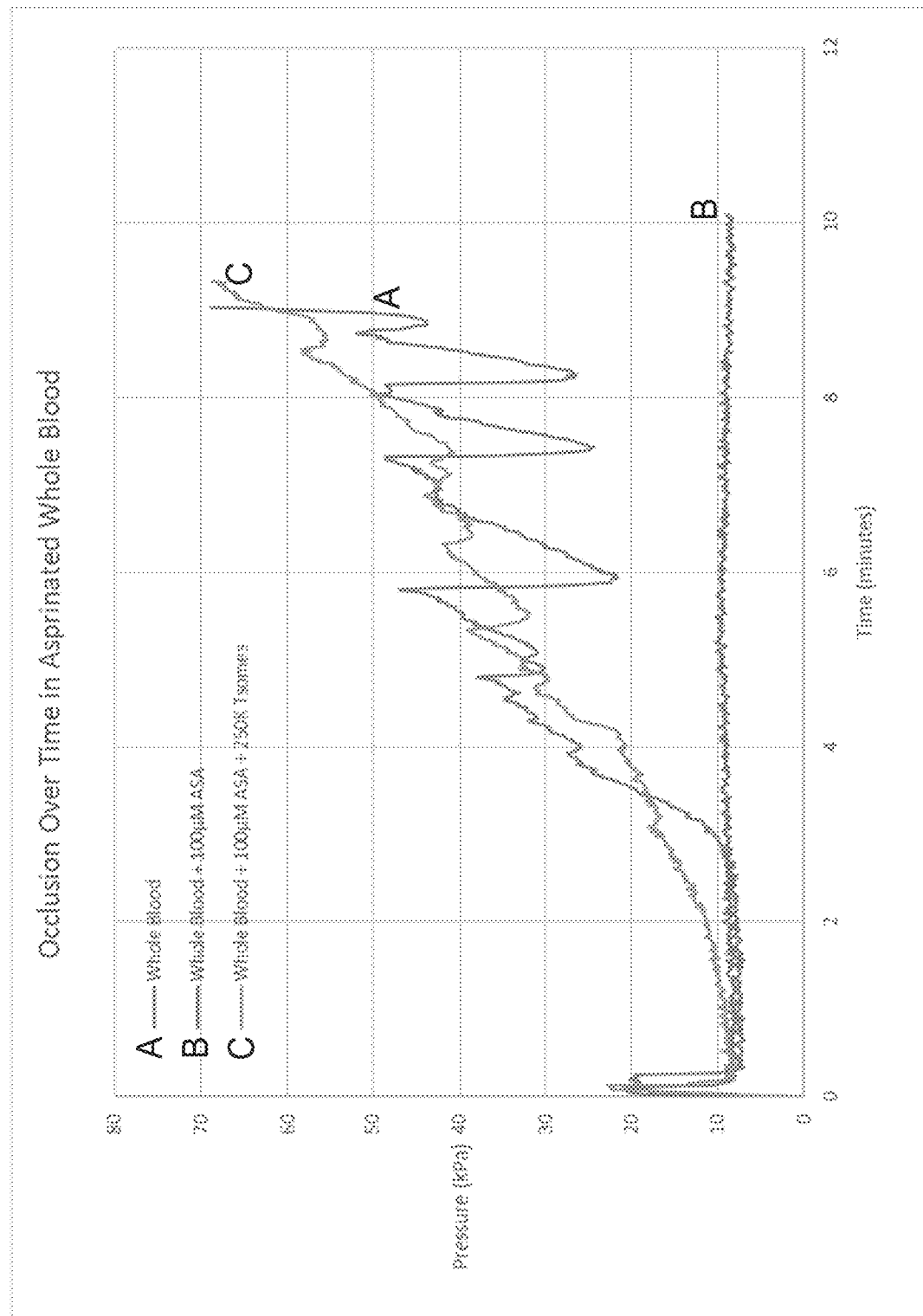
FIG. 23 shows the effect of thrombosomes supplementation to aspirin-(ASA-)inhibited whole blood (100 micromolar) on the interaction with plastic immobilized porcine collage under high shear, as measured by occlusion (pressure) over time.

The effect of thrombosomes on the recovery of thrombus formation was also evaluated using T-TAS® technology and a PL chip. FIG. 20 shows the occlusion time of whole blood treated only with buffer, aspirin (500 or aspirin (500 µM) and thrombosomes (at a concentration of 250,000 thrombosomes per µL). FIG. 21 shows the occlusion over time of whole blood, whole blood treated with aspirin (500 µM), or aspirin (500 µM) and thrombosomes (250,000/µL). FIGS. 22 and 23 show similar experimental data using 100 µM aspirin instead of 500 µM aspirin.

Figure 24:
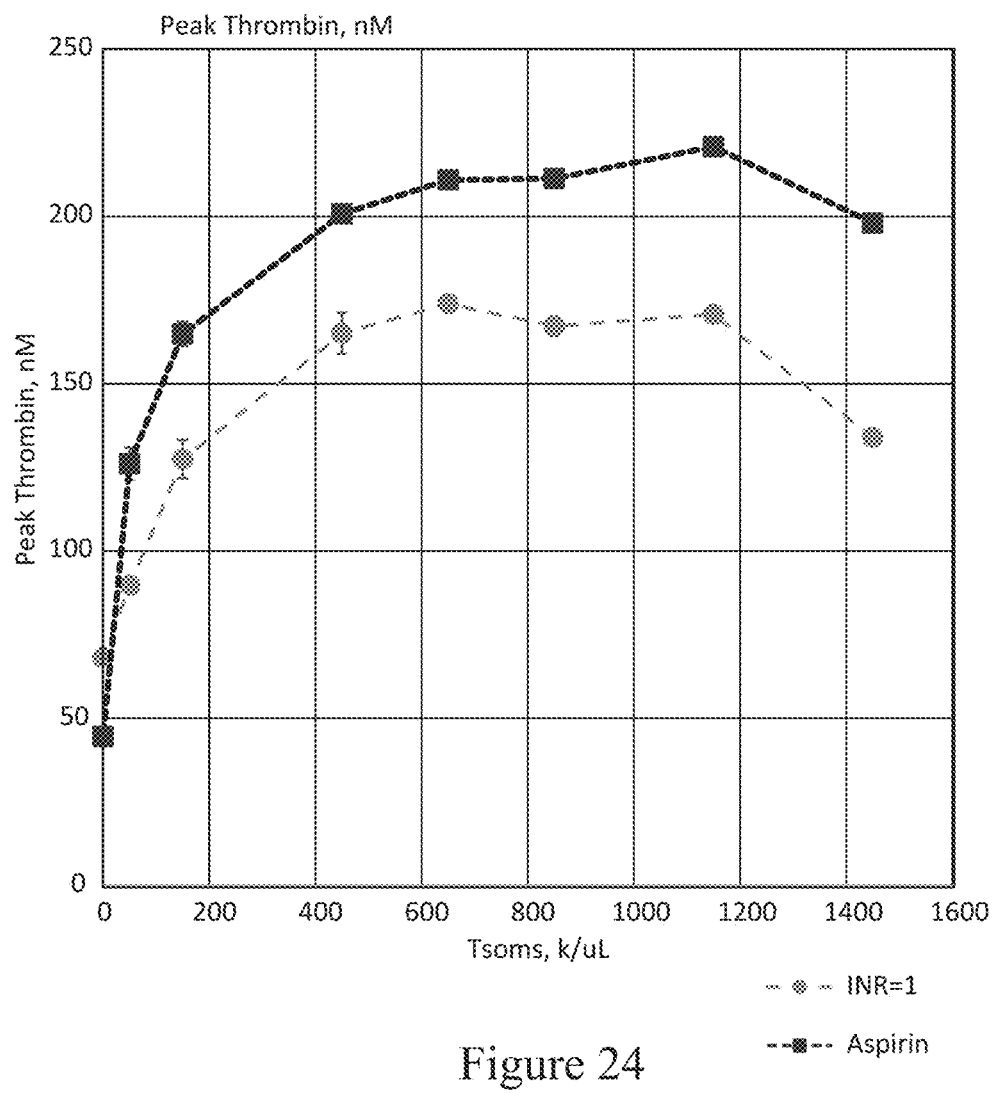
FIG. 24 shows the effect on peak thrombin of thrombosome supplementation to normal and aspirin-inhibited plasma.

The effect of aspirin treatment (concentration) on thrombin generation was measured. Thrombosomes were evaluated at concentrations 1450, 1150, 850, 650, 450, 150, 50, and 0 k/uL in PPP from patients taking baby aspirin daily and standard plasma (INR=1). FIG. 24 shows that the peak thrombin value of the aspirin plasma in absence of thrombosomes was below the normal range (about 45 nM; normal range is about 66-166 nM), but with thrombosomes addition, it came back to being within the normal range at even the lowest thrombosomes concentration used (50 k/µL). The values again were saturated at about 800 k thrombosomes and went up to 220 nM—5 times the value of this plasma in absence of thrombosomes (increase from 45 to 220 nM).

Example 6

Thrombosomes Reversed Prolonged PRP Occlusion Times Induced by Cangrelor

Additional experiments were carried out with cangrelor. Thrombosomes were prepared consistent with the procedure in Example 4. T-TAS® was carried out according to Example 4.

Figure 25A:
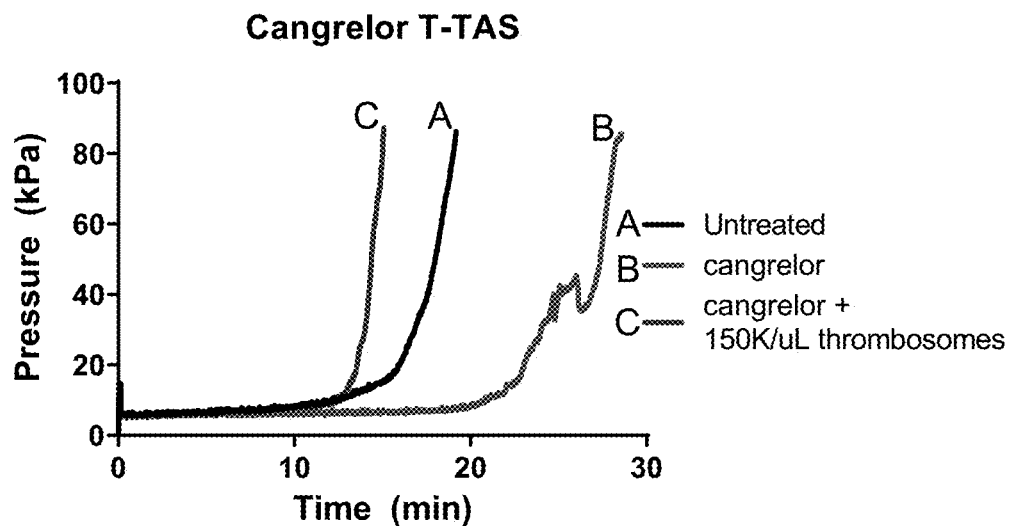
FIG. 25A shows the effect of cangrelor alone or cangrelor plus thrombosomes on platelet occlusion using T-TAS® technology.
Figure 25B:
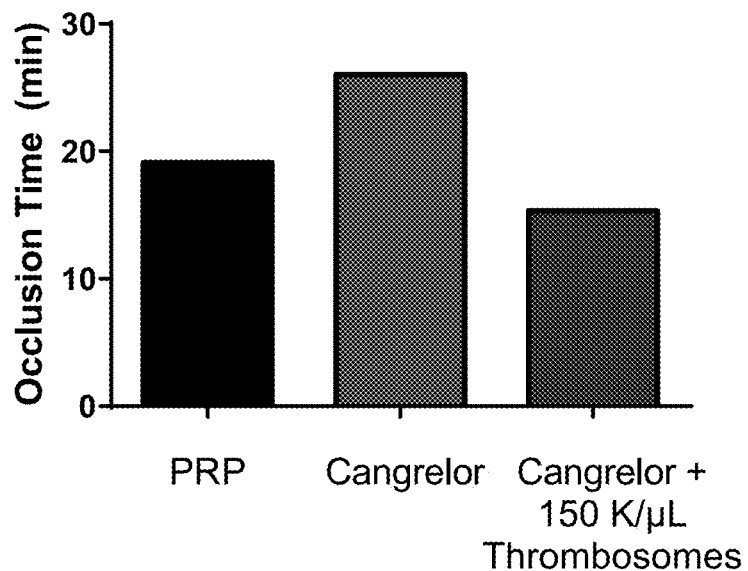
FIG. 25B is a bar plot of the occlusion time for data sets from FIG. 25A.

FIGS. 25A and 25B show that platelet rich plasma treated with 100 ng/mL cangrelor and ADP extended occlusion times from 19 to 26 minutes on the T-TAS® flow system (collagen and tissue factor coated channel). The addition of 150 k/µL thrombosomes decreased the time back to 15.3 minutes.

Example 7

Thrombosomes But Not Random Donor Platelets (RDP) Reversed Extended Occlusion Times Induced by Tirofiban in PRP Additional experiments were carried out with tirofiban. Thrombosomes were prepared consistent with the procedure in Example 4. T-TAS® was carried out according to Example 4. Random donor platelets were prepared from whole blood.

Figure 26A:
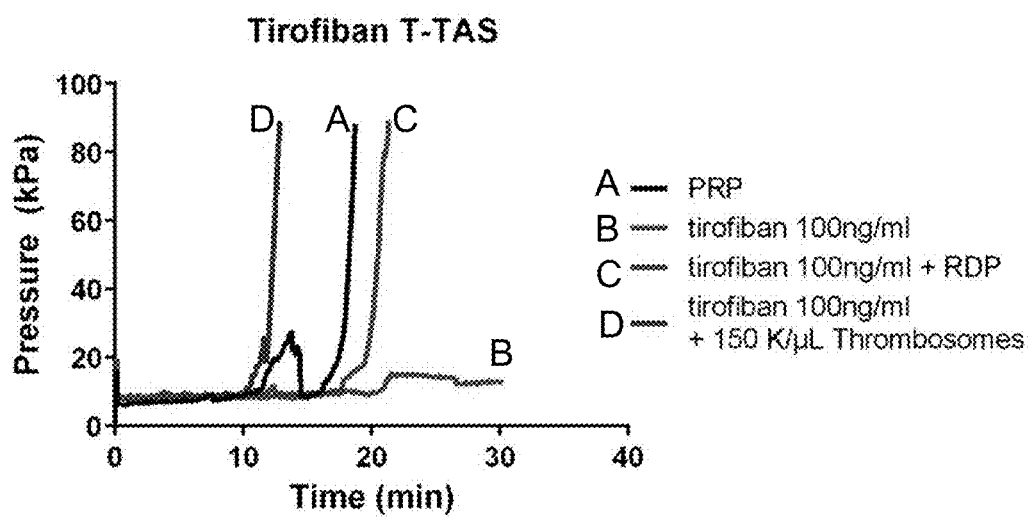
FIG. 26A shows the effect of tirofiban alone, or with random donor platelets (RDP) or thrombosomes on platelet occlusion using T-TAS® technology.
Figure 26B:
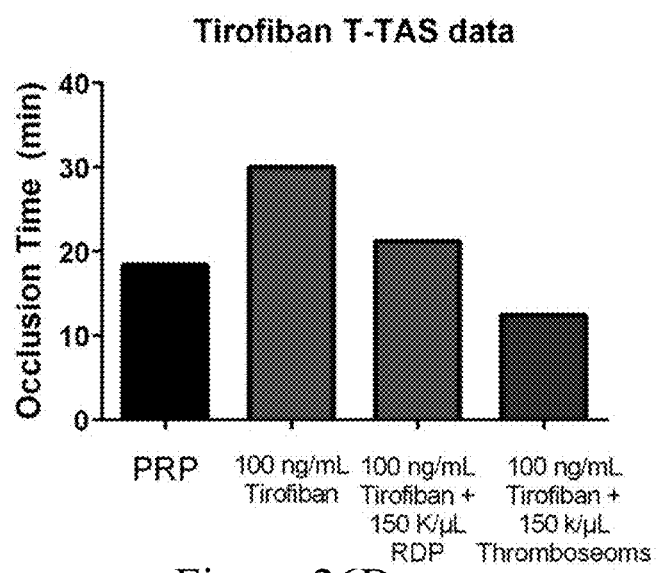
FIG. 26B is a bar plot of the occlusion time for data sets from FIG. 26A.

FIGS. 26A and 26B show that platelet rich plasma treated with 100 ng/mL tirofiban extended occlusion times from 18.43 to no occlusion on the T-TAS® flow system (collagen and tissue factor coated channel). The addition of 150 k/µL of thrombosomes decreased the time back to 12.94 minutes but RDP only partially recovered at the same count.

Example 8

Thrombosomes But Not Random Donor Platelets Reversed Extended Occlusion Times Induced by Eptifibatide in PRP Additional experiments were carried out with eptifibatide. Thrombosomes were prepared consistent with the procedure in Example 4. T-TAS® was carried out according to Example 4. Random donor platelets were prepared from whole blood.

Figure 27A:
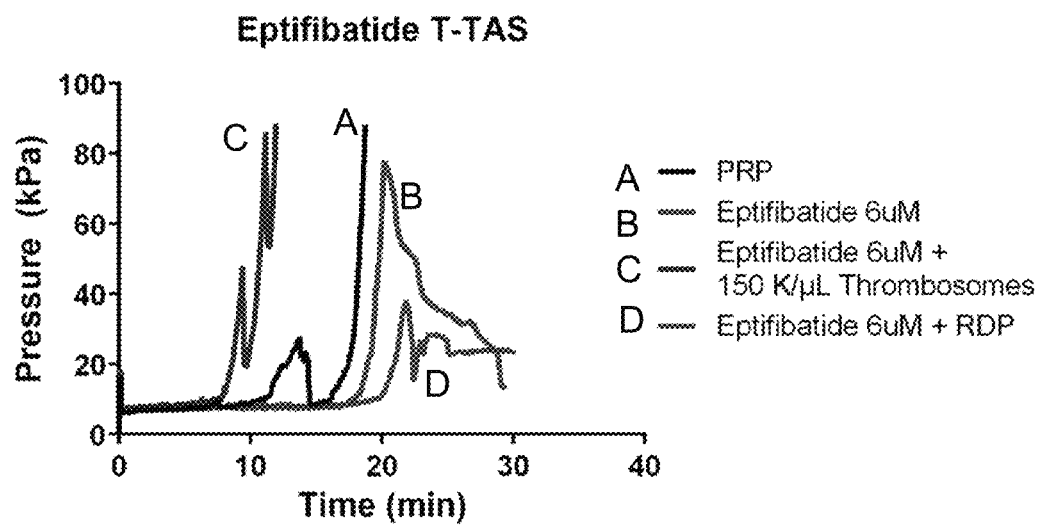
FIG. 27A shows the effect of eptifibatide alone, or with RDP or thrombosomes on platelet occlusion using T-TAS® technology.
Figure 27B:
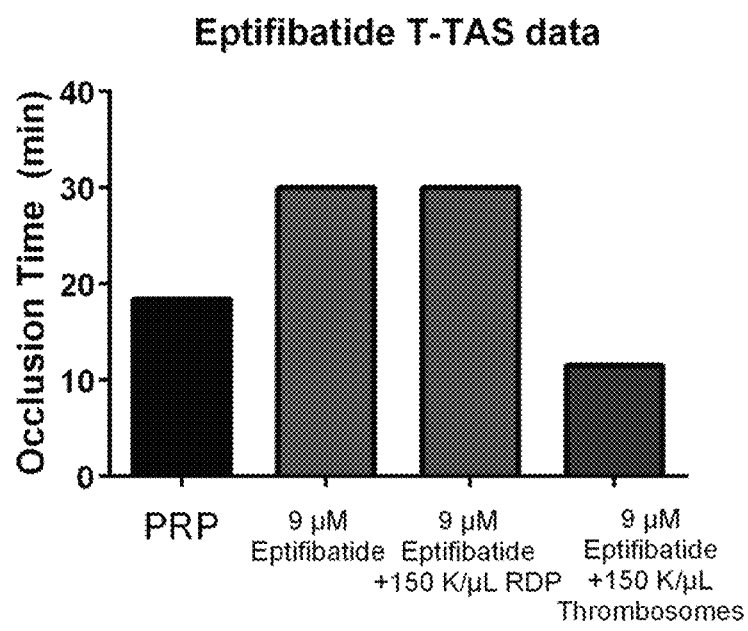
FIG. 27B is a bar plot of the occlusion time for data sets from FIG. 27A.

FIGS. 27A and 27B show that platelet rich plasma treated with 9 µM eptifibatide extended occlusion times from 18.43 to over 30 minutes on the T-TAS® flow system (collagen and tissue factor coated channel). The addition of 150 k/μL of thrombosomes decreased the time back to 11.56 minutes but not occlusion seen with same number of RDP.

Example 9

Thrombosomes Reversed Extended Occlusion Times Induced by AP2 (Anti-GpIIb/IIIa) in PRP Additional experiments were carried out with AP2. Thrombosomes were prepared consistent with the procedure in Example 4. T-TAS® was carried out according to Example 4. Random donor platelets were prepared from whole blood.

Figure 28A:
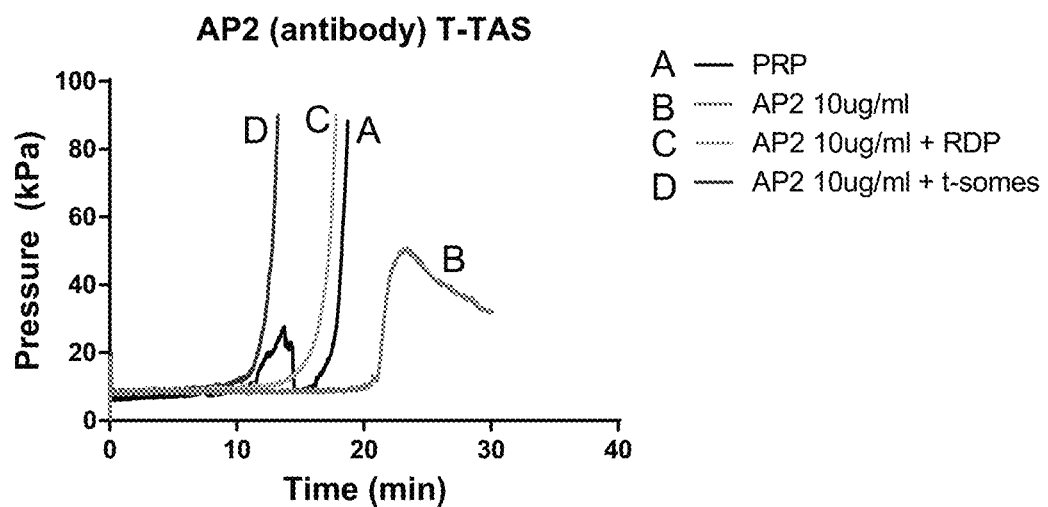
FIG. 28A shows the effect of AP2 alone, or with RDP or thrombosomes on platelet occlusion using T-TAS® technology.
Figure 28B:
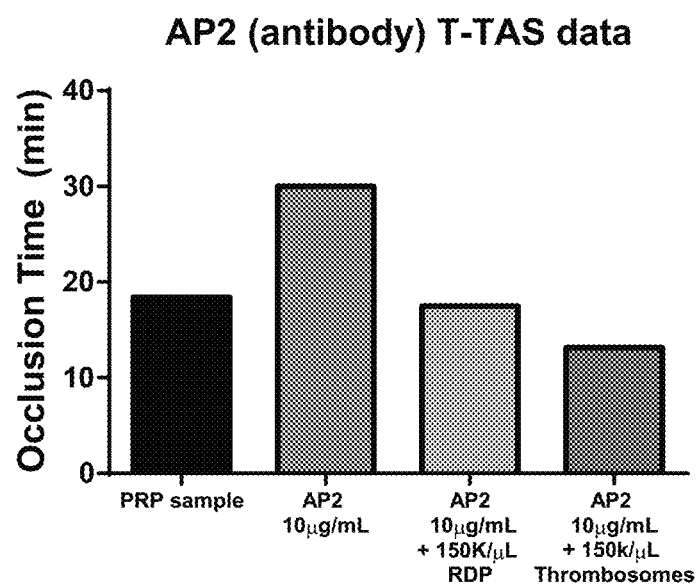
FIG. 28B is a bar plot of the occlusion time for data sets from FIG. 28A.

FIGS. 28A and 28B show that platelet rich plasma treated with 10 μg/mL AP-2 extended occlusion times from 18.43 to over 30 minutes on the T-TAS® flow system (collagen and tissue factor coated channel). The addition of 150 k/μL of thrombosomes decreased the time back to 13.14 minutes and occlusion was seen at 17.43 minutes same number of RDP.

Example 10

Thrombosomes Reversed Prolonged Occlusion in PRP from Subjects on Aspirin Therapy Additional experiments were carried out with aspirin. Thrombosomes were prepared consistent with the procedure in Example 4. T-TAS® was carried out according to Example 4. Random donor platelets were prepared from whole blood. The subject was on a standard dose of 81 mg/day of aspirin.

Figure 29A:
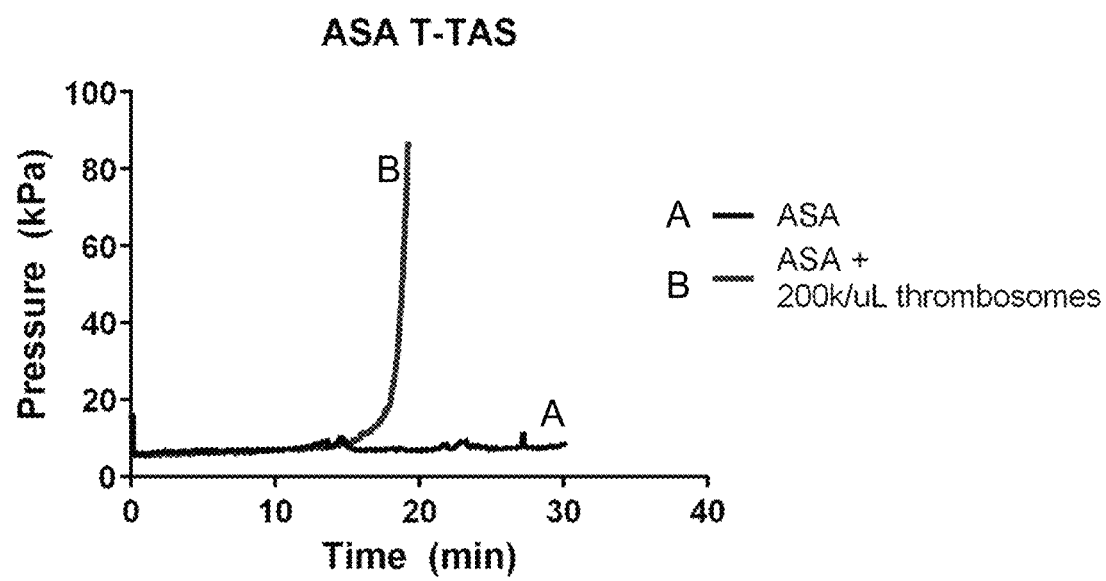
FIG. 29A shows the effect of thrombosomes on PRP taken from a subject on aspirin therapy using T-TAS® technology.
Figure 29B:
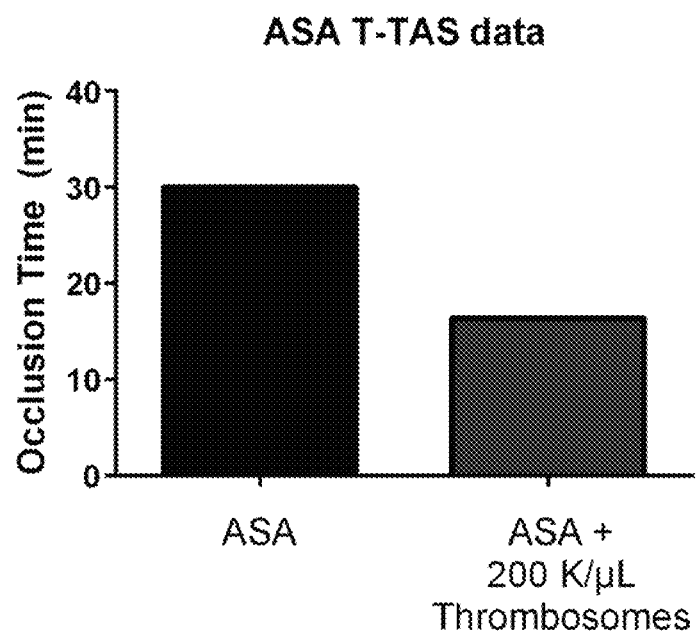
FIG. 29B is a bar plot of the occlusion time for data sets from FIG. 29A.

FIGS. 29A and 29B show that platelet rich plasma taken from an aspirin patient failed to occlude on the T-TAS® flow system (collagen and tissue factor coated channel). The addition of 200 k/μL of thrombosomes returned to normal occlusion time to 16 minutes.

Example 11

Thrombosomes Restore Thrombin Generation in Ex-Vivo Aspirin Platelet Rich Plasma Additional experiments were carried out with aspirin. Thrombosomes were prepared consistent with the procedure in Example 4. Thrombin generation was carried out according to Example 4.

Figure 30A:
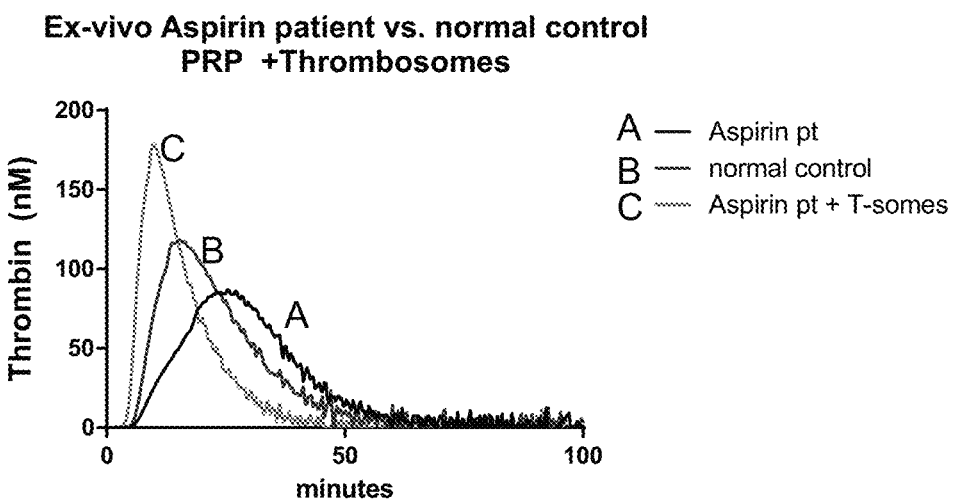
FIG. 30A shows the effect of thrombosomes on PRP taken from a subject on aspirin therapy on thrombin generation.
Figure 30B:
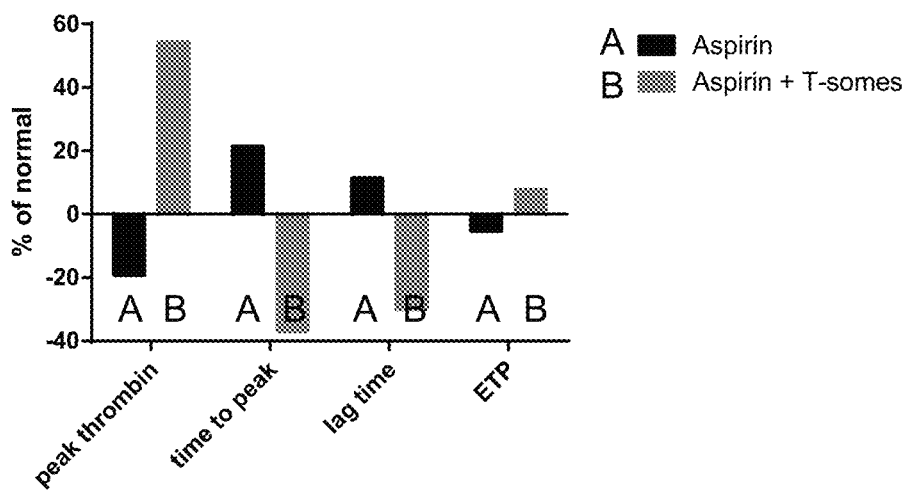
FIG. 30B is a bar plot of thrombin generation parameters for PRP taken from a subject on aspirin therapy, with or without added thrombosomes.

FIG. 30A shows Thrombin generation of platelet rich plasma from aspirin patient verses normal stimulated with PRP reagent was reversed with 50 k/μL of thrombosomes. FIG. 30B shows the change from and return to normal thrombin production, time to peak production, and lag time in three repeat aspirin ex-vivo samplings with thrombosomes (50 k/μL). (n=3 thrombosome lots, n=2 individuals).

Example 12

Thrombosomes Restore Hemostasis in PRP from Subject on NSAID Ibuprofen Therapy

Additional experiments were carried out with ibuprofen, an NSAID. Thrombosomes were prepared consistent with the procedure in Example 4. Aggregometry and T-TAS® were carried out according to Example 4.

Figure 31A:
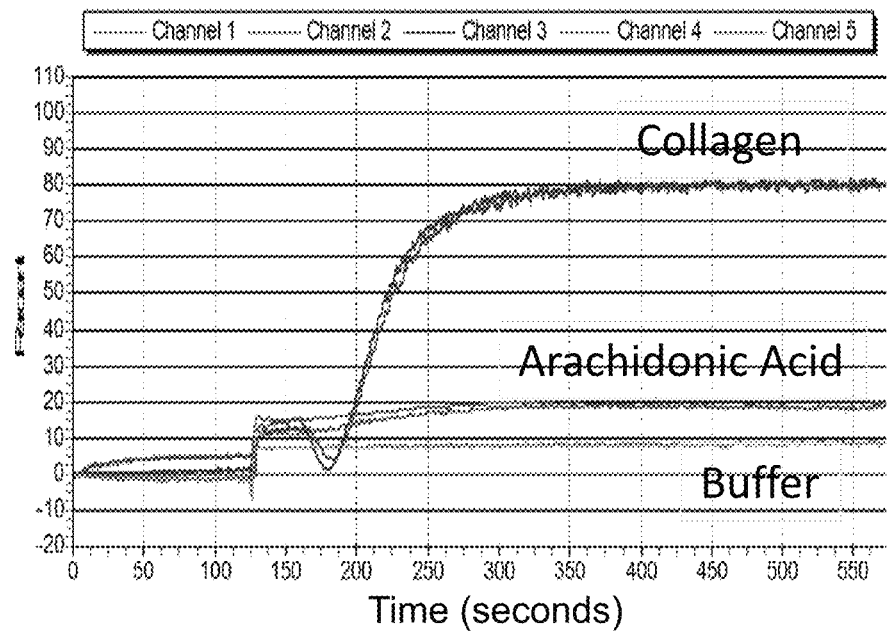
FIG. 31A shows aggregometry of PRP taken from a subject on ibuprofen therapy, with added buffer, arachidonic acid, or collagen.
Figure 31B:
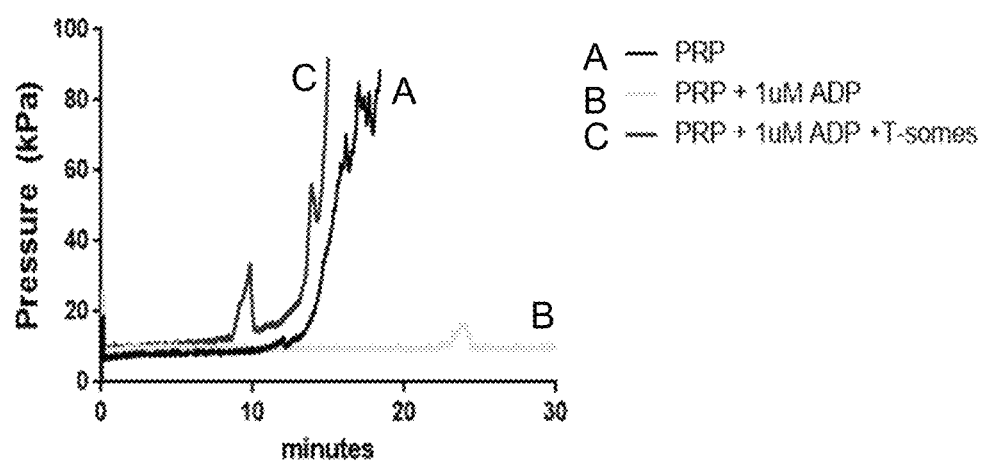
FIG. 31B shows the effect of ADP on PRP taken from a subject on ibuprofen therapy, with or without thrombosomes.

Platelet rich plasma was taken from subject on 800 mg ibuprofen. FIG. 31A shows that a lack of aggregation in response to arachidonic acid confirms NSAID presence in the PRP. FIG. 31B shows occlusion on the T-TAS® flow system (collagen and tissue factor coated channel); PRP from the ibuprofen patient demonstrated occlusion, while addition of ADP abolished occlusion. The addition of 150 k/μL thrombosomes restored occlusion.

Example 13

Thrombosomes® Restore Bleeding Time in NOD-SCID Mice Treated with Supra-Pharmacologic Clopidogrel Additional experiments were carried out with clopidogrel. Thrombosomes were prepared consistent with the procedure in Example 4.

The mouse was treated with clopidogrel for 5 days. The mouse was anesthetized, the tail end was snipped off followed by thrombosomes being immediately administered. The time from tail snip to tail stop bleeding was recorded by visual inspection.

Figure 32:
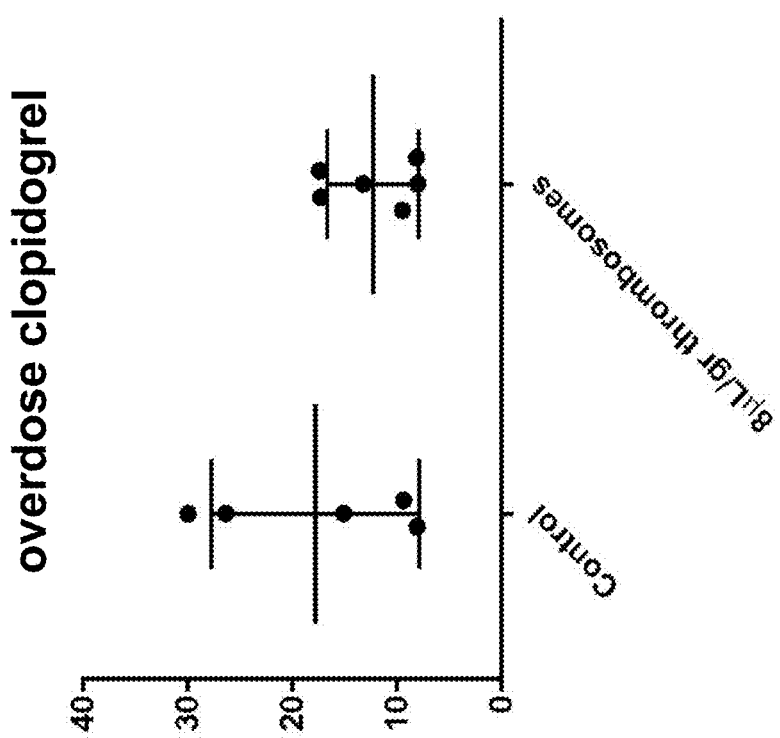
FIG. 32 shows the effect of dosing thrombosomes on the bleeding time of mice treated with a superpharmacologic dose of clopidogrel.

NOD/SCID mice were treated with ~3 times the clinical dose of clopidogrel for 5 days then assessed in the tail-snip bleed model. The bleed time (min) was extended to 17.8 minutes with clopidogrel treatment verses untreated at 9 minutes (data not shown). Treatment with 8 μL/gram of thrombosomes ($1.8 \times 10^9$ particles/mL at 200 μL) decreased bleeding to 12.31 minutes (FIG. 32).

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above. Furthermore, one having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. Embodiments of the invention so claimed are inherently or expressly described and enabled herein. In order to determine the metes and bounds of the invention, therefore, reference should be made to the appended claims.

What is claimed is:

1. A method of treating a coagulopathy in a subject, the method comprising administering to a human subject in need thereof, an effective amount of a rehydrated composition comprising freeze-dried platelet derivatives (FDPDs) and an incubating agent comprising one or more salts and a buffer, wherein the human subject is being treated with an antiplatelet agent selected from the group consisting of cangrelor, ticagrelor, prasugrel, abciximab, terutroban, picotamide, elinogrel, vorapaxar, atopaxar, cilostazol, epoprostenol, dipyridamole, treprostinil sodium, sarpogrelate, clopidogrel, eptifibatide, tirofiban, and ticlopidine, such that treatment with the antiplatelet agent is continued before and after the administering without stopping the treatment;

wherein the administering comprises administering parenterally, intravenously, intramuscularly, intrathecally, subcutaneously, or intraperitoneally; and wherein the effective amount of the composition is at least $1.0 \times 10^8$ FDPDs/kg of the human subject.

2. The method of claim 1, wherein the administering comprises administering intravenously.

3. The method of claim 1, wherein the one or more salts are selected from the group consisting of phosphate salts, sodium salts, potassium salts, calcium salts, magnesium salts, and a combination of two or more thereof.

4. The method of claim 1, wherein the buffer comprises HEPES, sodium bicarbonate ($NaHCO_3$), or a combination thereof.

5. The method of claim 1, wherein the composition further comprises one or more saccharides, and wherein the one or more saccharides comprise trehalose in the range of 10 mM to 500 mM.

6. The method of claim 5, wherein the composition further comprises polysucrose in the range of 3% to 7%.

7. The method of claim 6, wherein the composition further comprises an organic solvent.

8. The method of claim 1, wherein the composition further comprises an organic solvent.

9. The method of claim 1, wherein the effective amount of the composition is between $1.0 \times 10^8$ to $1.4 \times 10^{10}$ FDPDs/kg of the subject.

10. The method of claim 1, wherein the effective amount of the composition is between $1.0 \times 10^8$ to $1.0 \times 10^{10}$ FDPDs/kg of the subject.

11. The method of claim 1, wherein the effective amount of the composition is between $5.0 \times 10^8$ to $1.0 \times 10^{10}$ FDPDs/kg of the subject.

12. The method of claim 1, wherein the effective amount of the composition is between $1.0 \times 10^9$ to $1.0 \times 10^{10}$ FDPDs/kg of the subject.

13. The method of claim 1, wherein the effective amount of the composition is between $5.0 \times 10^9$ to $1.0 \times 10^{10}$ FDPDs/kg of the subject.

14. The method of claim 1, wherein the effective amount of the composition is at least $1.0 \times 10^9$ FDPDs/kg of the subject.

15. The method of claim 1, wherein the effective amount of the composition is at least $5.0 \times 10^9$ FDPDs/kg of the subject.

16. The method of claim 15, wherein the human subject is in need thereof because the subject is being treated with two antiplatelet agents.

17. The method of claim 1, wherein the human subject is being treated with aspirin in addition to the antiplatelet agent.

18. The method of claim 1, wherein the method is a method for preparing the human subject for surgery, and wherein the dose of the antiplatelet agent is not reduced before the surgery.

19. The method of claim 1, wherein the antiplatelet agent is selected from the group consisting of cangrelor, ticagrelor, prasugrel, abciximab, terutroban, picotamide, elinogrel vorapaxar, atopaxar, cilostazol, epoprostenol, dipyridamole, treprostinil sodium, and sarpogrelate.

20. The method of claim 1, wherein at least 90% of the FDPDs have a particle size between 0.5 μm and 2.5 μm.

21. The method of claim 1, wherein the human subject is being treated with a single anti-platelet agent.

22. The method of claim 1, wherein the human subject is being treated with two antiplatelet agents.

* * * * *